US010653790B2

(12) United States Patent
Dodgson et al.

(10) Patent No.: US 10,653,790 B2
(45) Date of Patent: May 19, 2020

(54) COMPOSITIONS AND METHODS RELATED TO SCAVENGER PARTICLES

(71) Applicant: NANOTICS, LLC, Mill Valley, CA (US)

(72) Inventors: John Dodgson, London (GB); Louis Hawthorne, Mill Valley, CA (US)

(73) Assignee: NaNotics, LLC, Mill Valley, CA (US)

( * ) Notice: Subject to any disclaimer, the term of this patent is extended or adjusted under 35 U.S.C. 154(b) by 0 days.

(21) Appl. No.: 15/748,335

(22) PCT Filed: Jul. 29, 2016

(86) PCT No.: PCT/US2016/044674
§ 371 (c)(1),
(2) Date: Jan. 29, 2018

(87) PCT Pub. No.: WO2017/019949
PCT Pub. Date: Feb. 2, 2017

(65) Prior Publication Data
US 2018/0214566 A1  Aug. 2, 2018

Related U.S. Application Data

(60) Provisional application No. 62/319,092, filed on Apr. 6, 2016, provisional application No. 62/236,507, filed (Continued)

(51) Int. Cl.
*A61K 47/64* (2017.01)
*A61K 9/00* (2006.01)
(Continued)

(52) U.S. Cl.
CPC .......... *A61K 47/642* (2017.08); *A61K 9/0092* (2013.01); *A61K 9/51* (2013.01);
(Continued)

(58) Field of Classification Search
CPC .. A61K 47/642; A61K 47/557; A61K 47/665; A61K 47/6923; A61K 9/51; A61K 9/1676
See application file for complete search history.

(56) References Cited

U.S. PATENT DOCUMENTS 7,727,528 B2   6/2010  Adcock
7,854,717 B1  12/2010  Lentz
(Continued)

FOREIGN PATENT DOCUMENTS

DE   10144251 A1   3/2003
EP    1174129 A1   1/2002
(Continued)

OTHER PUBLICATIONS

Cauda et al, Multiple core shell functionalized colloidal mesoporous silica nanoparticles, Journal of American Chemical Society, 2009, 131:32: 11361-11370 (Year: 2009).*

(Continued)

*Primary Examiner* — Carlos A Azpuru
(74) *Attorney, Agent, or Firm* — David Halstead; Lucas Watkins; Foley Hoag LLP

(57) ABSTRACT

The disclosure provides, among other things, compositions that bind to and inhibit the biological activity of soluble biomolecules, as well as pharmaceutical compositions thereof. The compositions may comprise a plurality of particles that specifically bind a target, such as a soluble biomolecule or a biomolecule on the surface of a pathogen, to inhibit the target (or pathogen) from interacting with other molecules or cells.

20 Claims, 7 Drawing Sheets

Sponge impregnated w/TNF (yellow)

sTNF-Rs (brown) binding to TNF

CU of sTNF-Rs bound to TNF in sponge pores

Related U.S. Application Data on Oct. 2, 2015, provisional application No. 62/198,531, filed on Jul. 29, 2015, provisional application No. 62/198,541, filed on Jul. 29, 2015, provisional application No. 62/198,519, filed on Jul. 29, 2015.

(51) Int. Cl.

| | | |
|---|---|---|
| *A61K 47/66* | (2017.01) | |
| *A61K 47/69* | (2017.01) | |
| *A61K 47/54* | (2017.01) | |
| *A61K 9/51* | (2006.01) | |
| *A61K 9/16* | (2006.01) | |

(52) U.S. Cl.
CPC .......... *A61K 47/557* (2017.08); *A61K 47/665* (2017.08); *A61K 47/6923* (2017.08); *A61K 9/1676* (2013.01)

(56) References Cited

U.S. PATENT DOCUMENTS

| | | | |
|---|---|---|---|
| 7,932,311 B2 | 4/2011 | Aymonier et al. | |
| 8,133,490 B2 | 3/2012 | Lentz | |
| 8,586,096 B2 | 11/2013 | Katti et al. | |
| 8,685,538 B2 | 4/2014 | Torchilin et al. | |
| 8,926,994 B2 | 1/2015 | Serda et al. | |
| 9,623,081 B2 | 4/2017 | Hawthorne | |
| 9,907,831 B2 | 3/2018 | Hawthorne | |
| 2004/0105821 A1 | 6/2004 | Bernstein et al. | |
| 2004/0166166 A1 | 8/2004 | Matsunami et al. | |
| 2004/0170626 A1 | 9/2004 | Schuurman et al. | |
| 2004/0265392 A1* | 12/2004 | Tovar .................. | B82Y 5/00 424/492 |
| 2006/0199820 A1 | 9/2006 | Bannen et al. | |
| 2008/0075690 A1 | 3/2008 | Howell | |
| 2008/0277346 A1 | 11/2008 | Kirkland et al. | |
| 2012/0108787 A1 | 5/2012 | Lue | |
| 2012/0141797 A1 | 6/2012 | Sherman et al. | |
| 2013/0195972 A1 | 8/2013 | Manku et al. | |
| 2013/0196450 A1 | 8/2013 | Van Hoonacker et al. | |
| 2013/0337070 A1 | 12/2013 | Brenneisen et al. | |
| 2014/0010879 A1 | 1/2014 | Shen et al. | |
| 2014/0235803 A1 | 8/2014 | Jiang et al. | |
| 2014/0296836 A1 | 10/2014 | Shen et al. | |
| 2014/0341975 A1 | 11/2014 | Livneh | |
| 2015/0112842 A1 | 4/2015 | Sieger et al. | |
| 2015/0231233 A1 | 8/2015 | Lentz | |
| 2017/0038382 A1 | 2/2017 | Hawthorne | |
| 2017/0056327 A1 | 3/2017 | Ml et al. | |
| 2018/0256747 A1 | 9/2018 | Hawthorne et al. | |

FOREIGN PATENT DOCUMENTS

| | | |
|---|---|---|
| EP | 1227843 A2 | 8/2002 |
| EP | 1949915 A2 | 7/2008 |
| WO | WO-2004/071641 A2 | 8/2004 |
| WO | WO-2005/107802 A2 | 11/2005 |
| WO | WO-2006/086428 A2 | 8/2006 |
| WO | WO-2008/127515 A1 | 10/2008 |
| WO | WO-2009/030492 A2 | 3/2009 |
| WO | WO-2009061853 A2 | 5/2009 |
| WO | WO-2010/042555 A2 | 4/2010 |
| WO | WO-2012/163544 A1 | 12/2012 |
| WO | WO-2013/029278 A1 | 3/2013 |
| WO | WO-2013/179143 A2 | 12/2013 |
| WO | WO-2014/041544 A1 | 3/2014 |
| WO | 2014109842 * | 7/2014 |
| WO | WO-2014/109842 A2 | 7/2014 |
| WO | WO-2015/112842 A1 | 7/2015 |
| WO | WO-2016/054522 A1 | 4/2016 |
| WO | 2016/054522 A1 * | 7/2016 |
| WO | WO-2017/004159 A1 | 1/2017 |
| WO | WO-2017/019949 A1 | 2/2017 |
| WO | 2014109842 * | 7/2017 |
| WO | WO-2017/176762 A1 | 10/2017 |
| WO | WO-2018/129188 A1 | 7/2018 |
| WO | WO-2018/129207 A1 | 7/2018 |

OTHER PUBLICATIONS

Aderka, et al., "Increased serum levels of soluble receptors for tumor necrosis factor in cancer patients," Cancer Res, 51(20): 5602-5607 (1991).

Cauda, et al., "Multiple core shell functionalized colloidal mesoporous silica nanoparticles," J American Chem Society, 131(32): 11361-11370 (2009).

Charych et al., "NKTR-214, an engineered cytokine with biased IL2 receptor binding, increased tumor exposure, and marked efficacy in mouse tumor models," Clin Cancer Res, 22(3):680-690 (2016).

Douglas et al., "Self-assembly of DNA into nanoscale three-dimensional shapes," Nature, 459(7245):414-418 (2009).

Duffy et al., "The ADAMs: New Therapeutic Targets for Cancer?" Cancer Targeted Drug Delivery. Springer New York, 273-287 (2013).

Extended European Search Report issued by the European Patent Office in corresponding Application No. 15740254.6, dated Dec. 20, 2017.

Giai, Constanza et al. "Shedding of Tumor Necrosis Factor Receptor 1 Induced by Protein A Decreases Tumor Necrosis Factor Alpha Availability and Inflammation during Systemic *Staphylococcus aureus* Infection," Infection & Immunity, 81(11):4200 (2013).

Holtan, Shernan G. et al. "Cancer and Pregnancy: Parallels in Growth, Invasion, and Immune Modulation and Implications for Cancer Therapeutic Agents", Mayo Clinical Protocols, 84(11):985-1000 (2008).

International Search Report and Written Opinion for International Application No. PCT/US2016/04474 dated Oct. 13, 2016.

International Search Report and Written Opinion for International Application No. PCT/US2018/012386, dated Mar. 28, 2018.

International Search Report and Written Opinion for International Application No. PCT/US2018/012414, dated Mar. 28, 2018.

Li et al., "Engineered interleukin-2 antagonists for the inhibition of regulatory T cells," J Immunother, 32(9):887-894 (2009).

Li et al., PEGylated recombinant human tumor necrosis factor alpha: preparation and anti-tumor potency, Acta Pharmacol Sin, 22(6):549-555 (2001).

Mullberg et al., "A Metalloprotease Inhibitor Blocks Shedding of the IL-6 Receptor and the p60 TNF Receptor," J Immunol, 155: 5198-5205 (1995).

Parker Annual Report 2014.

Partial Supplementary European Search Report issued by the European Patent Office in corresponding Application No. EP 15740254.6, dated Sep. 25, 2017.

Sheu et al., "A Novel Role of Metalloproteinase in Cancer-mediated Immunosuppression," Cancer Res, 61: 237-242 (2001).

Waldmann et al.,"Anti-Tac (daclizumab, Zenapax) in the treatment of leukemia, autoimmune diseases, and in the prevention of allograft rejection: a 25-year personal odyssey," J Clin Immunol, 27(1):1-18 (2007).

Yang et al., "The use of polyethylene glycol☐ modified interleukin ☐ 2 (PEG☐ IL☐ 2) in the treatment of patients with metastatic renal cell carcinoma and melanoma," Cancer, 76(4):687-694 (1995).

Yousef, Hanadie et al. "Systemic Attenuation of the TGFß Pathway by a Single Drug Simultaneously Rejuvenates Hippocampal Neurogenesis and Myogenesis in the same old Mammal," Oncotarget, 6(14):11959 (2015).

Extended European Search Report for EP Application No. 16818651.8 dated Jan. 31, 2019.

Extended European Search Report received for EP Patent Application No. EP16831405, dated Feb. 5, 2019.

International Preliminary Report on Patentability for International Application No. PCT/US2017/025954 dated Oct. 9, 2018.

Bork, "Powers and Pitfalls in Sequence Analysis: The 70% Hurdle," Genome Research, 10:398-400 (2000).

(56) References Cited

OTHER PUBLICATIONS

Bowie et al., "Deciphering the Message in Protein Sequences: Tolerance to Amino Acid Substitutions," Science, 247:1306-1310 (1990).
Brown et al., "Tolerance to Single, but Not Multiple, Amino Acid Replacements in Antibody VH CDR2," J Immunol, 156(9):3285-3291 (1996).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol, 111:2129-2138 (1990).
Clark et al., "Discovery and Development of Janus Kinase (JAK) Inhibitors for Inflammatory Diseases," J Med Chem, 57(12):5023-5038 (2014).
Guido et al., "Virtual Screening and Its Integration with Modern Drug Design Technologies," Curr Med Chem, 15(1):37-46 (2008).
International Preliminary Report on Patentability for International Application No. PCT/US2018/012414 dated Jul. 9, 2019.
International Search Report and Written Opinion for International Application No. PCT/US2017/025954, dated Sep. 8, 2017.
Lazar et al., "Transforming Growth Factor alpha: Mutation of Aspartic Acid 47 and Leucine 48 Results in Different Biological Activities," Mol Cell Biol, 8:1247-1252 (1988).
Vajdos et al., "Comprehensive Functional Maps of the Antigen Binding Site of an Anti-ErbB2 Antibody Obtained with Shotgun Scanning Mutagenesis," J Mol Biol, 320(2):415-428 (2002).

* cited by examiner

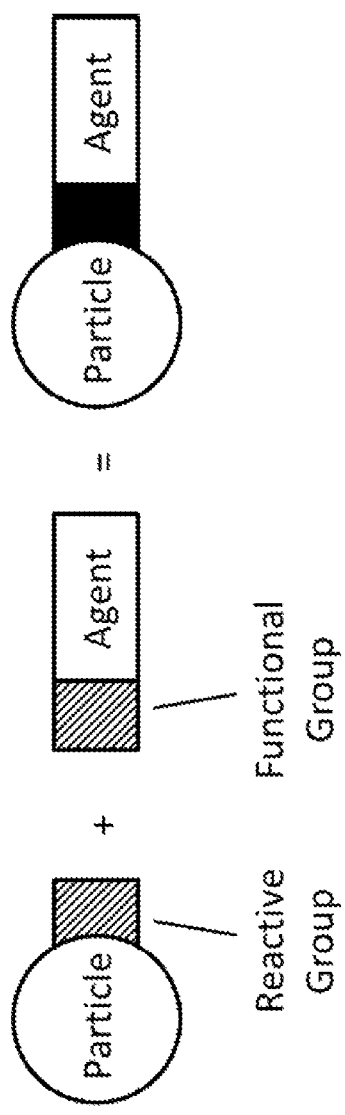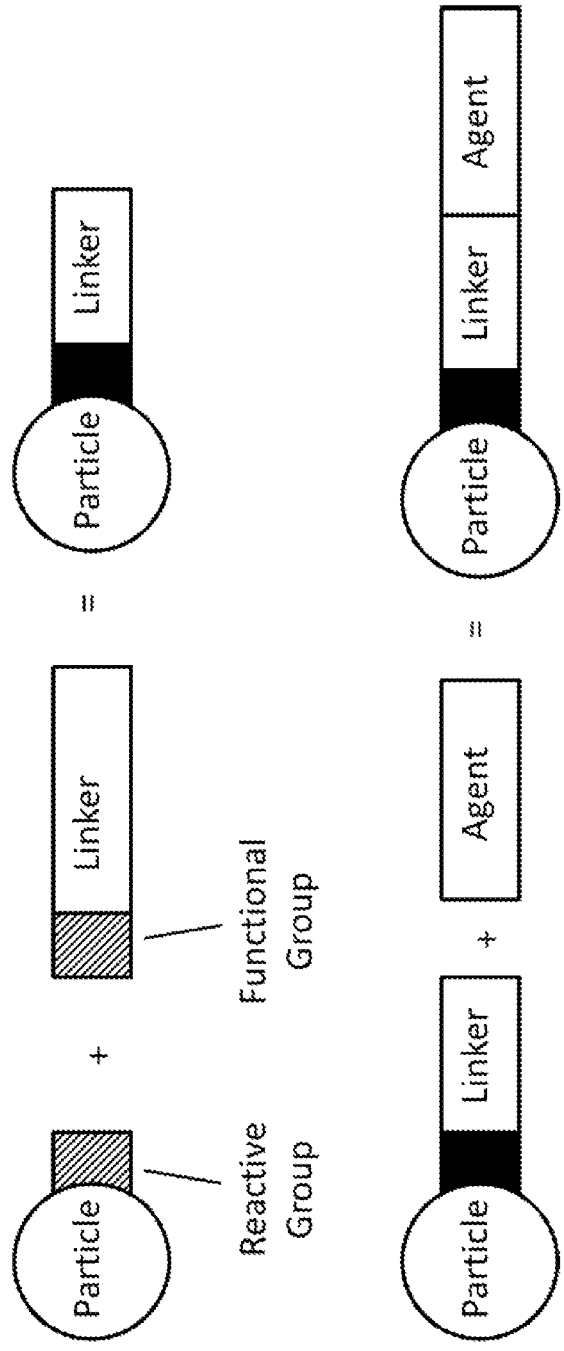

COMPOSITIONS AND METHODS RELATED TO SCAVENGER PARTICLES

REFERENCE TO RELATED APPLICATIONS

This application is a U.S. National Stage of International Patent Application No. PCT/US2016/044674, filed Jul. 29, 2016, which claims priority to U.S. Provisional Patent Application No. 62/198,531, filed Jul. 29, 2015; U.S. Provisional Patent Application No. 62/198,519, filed Jul. 29, 2015; U.S. Provisional Patent Application No. 62/198,541, filed Jul. 29, 2015; U.S. Provisional Patent Application No. 62/236,507, filed Oct. 2, 2015; and U.S. Provisional Patent Application No. 62/319,092, filed Apr. 6, 2016; the contents of each of which are hereby incorporated by reference herein in their entirety.

BACKGROUND

Dozens of anti-cancer therapies available clinically or under development involve stimulation of the immune system's ability either to recognize or destroy cancer, or both. Three of the most prominent are the anti-checkpoint inhibitors Yervoy® (ipilimumab) from Bristol-Myers Squibb, Keytruda® (pembrolizumab, formerly lambrolizumab) from Merck. However, these and other approaches involve net up-regulation of a subject's immune system, inducing potentially serious symptoms akin to autoimmune disorders and/or other significant side effects.

There is a need in the art for more effective pharmacological approaches for addressing cancer, particularly metastatic cancer, without disturbing a subject's capacity for avoiding auto-immunity. Among other things, the present disclosure provides methods and compositions based on alternative approaches for harnessing a subject's own immune system against cancer, including dis-inhibiting the tumor microenvironment, i.e., weakening the tumor's defensive system, versus stimulating immune cells.

SUMMARY

The disclosure provides, among other things, compositions that bind to and inhibit the biological activity of biomolecules, especially soluble molecules, as well as pharmaceutical compositions thereof. Also provided herein are a number of applications in which the compositions are useful. For example, compositions described herein are useful for inhibiting proliferation, growth, and/or survival of a cell, such as a cancer cell. Additionally, compositions described herein are useful for preventing and/or treating aging, metabolic disorders, and neurodegenerative diseases. In another example, compositions described herein can be useful to bind to and neutralize toxins (e.g., zootoxins, bacterial toxins, and/or plant toxins), viruses, or other foreign compounds in the circulation of a subject.

BRIEF DESCRIPTION OF THE DRAWINGS

In FIG. 5, each core subparticle and protecting subparticle is substantially spherical and approximately the same size; however, the subparticles within a particle may vary in shape and/or size. Additionally, the subparticles of FIG. 5 are shown as packing in a hexagonal pattern; however, the subparticles of a particle may pack with other geometries or they may pack randomly. The relative sizes of the subparticles, capture ligands, targets, and void space in FIG. 5 are not necessarily shown to scale.

Figure 1:
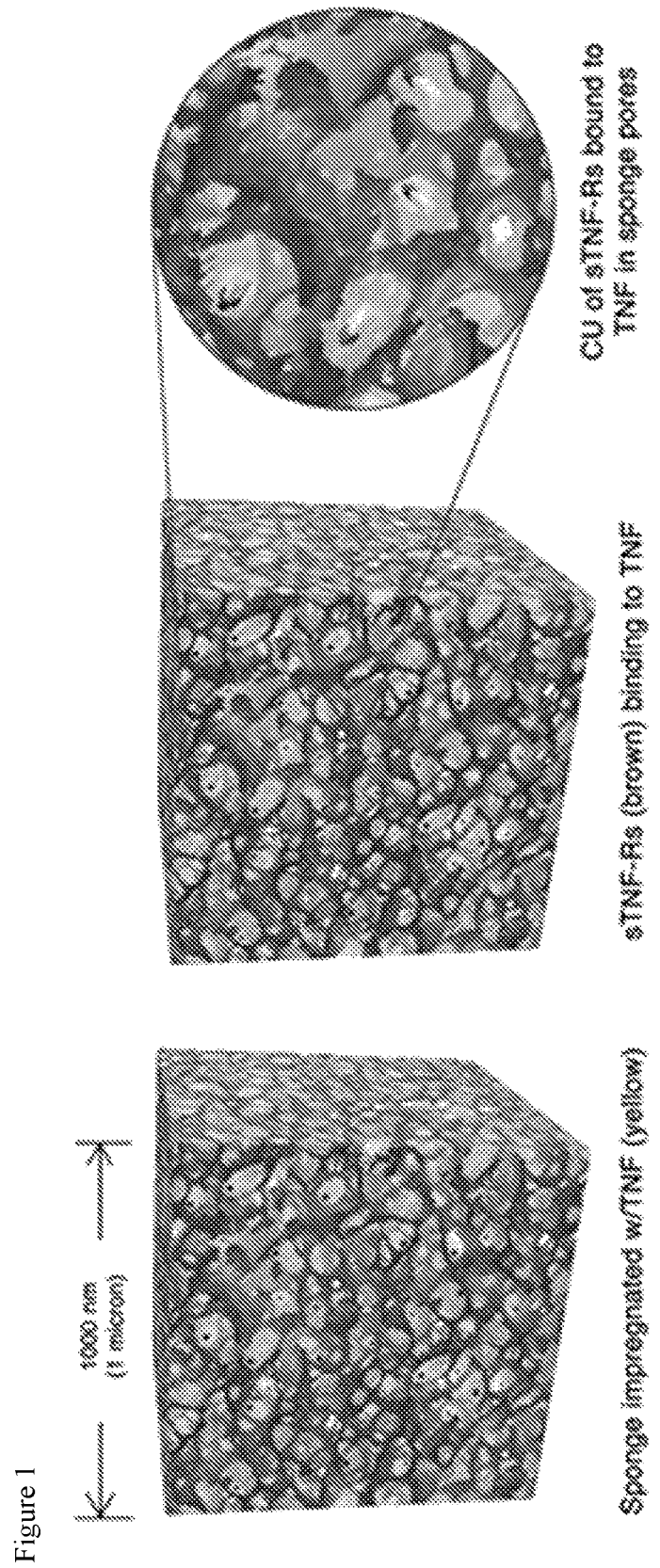
FIG. 1 depicts an exemplary embodiment of a particle that binds to soluble forms of TNF receptor (sTNF-R). The particle is approximately one cubic micron. The inner surfaces of the particle comprise an immobilized TNF agent, which is capable of binding to the sTNF-R target and sequestering (scavenging) it away from its natural ligands, thereby inhibiting interactions between the sTNF-R target and other proteins and cells. The inner surfaces of the particle define boundaries comprising void space.
Figure 2:
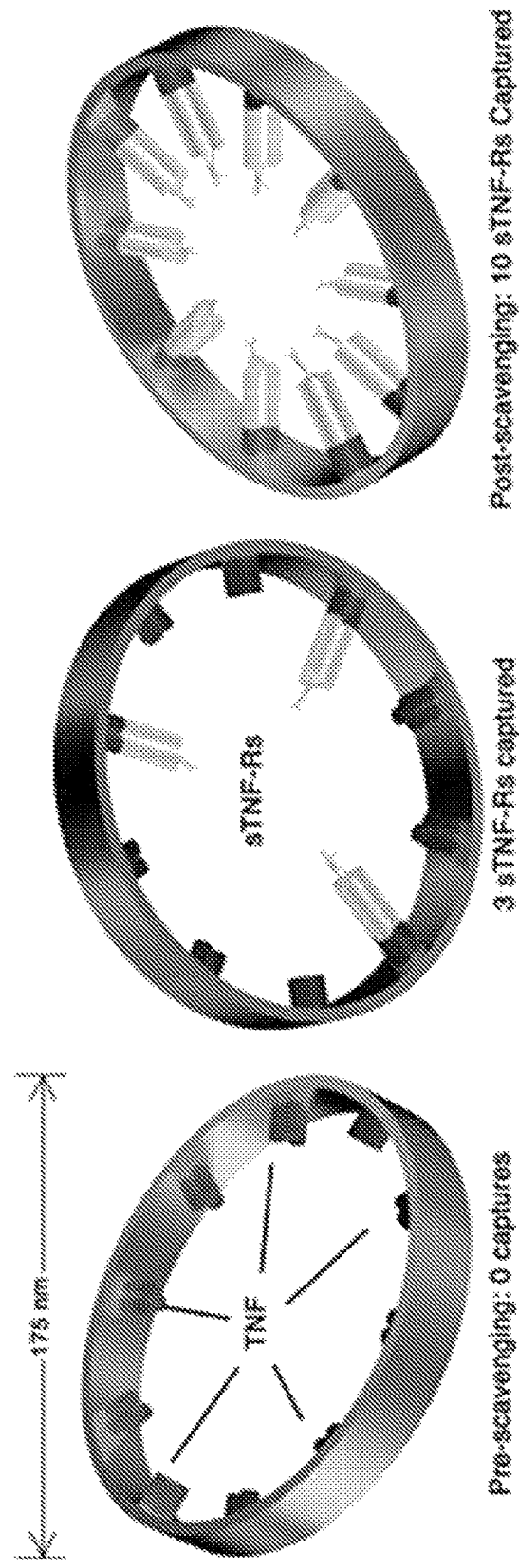
FIG. 2 depicts an exemplary embodiment of a particle comprising a TNF agent that binds to soluble forms of a TNF receptor (sTNF-R) target. The three particles shown in FIG. 2 are depicted as having bound 0, 3, or 10 molecules of the sTNF-R target. The ring-shaped particle has a diameter of approximately 175 nm, although the TNF agent and sTNF-R target are not shown to scale. The inner surfaces of the particle contain immobilized TNF agent, which is capable of binding to the sTNF-R target and sequestering (scavenging) it away from its natural ligands, thereby inhibiting interactions between the sTNF-R target and other proteins and cells. The interior of the ring-shaped particle comprises void space.
Figure 3:
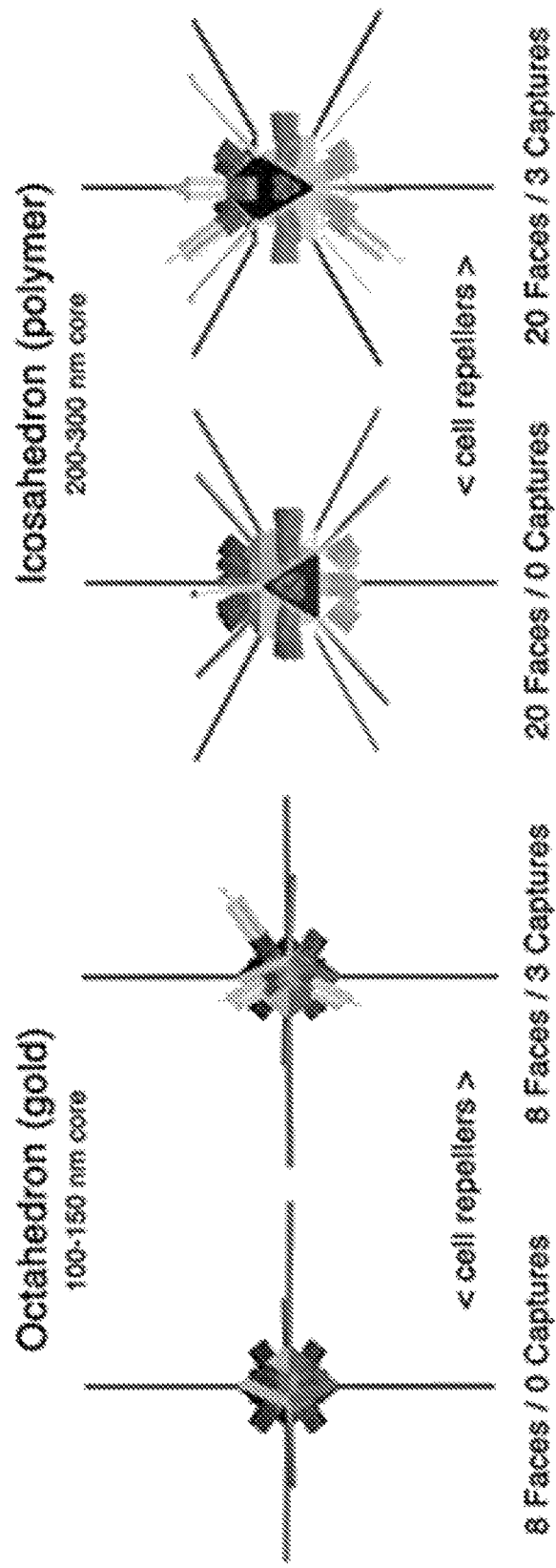
FIG. 3 depicts exemplary embodiments of particles comprising protrusions. The particle at the left of the figure is an octahedron with a core having a longest dimension of 100 to 150 nm. The particle at the right of the figure is an icosahedron with a core having a longest dimension of 200 to 300 nm. Each particle further comprises molecular protrusions pointing outward from the vertices of the core polyhedral structure. The particles are depicted as comprising an agent, shown in dark gray, and some particles are depicted as having bound a target (e.g., a biomolecule), shown in light gray and identified as 0 or 3 "captures." The protrusions serve as "cell repellers," which inhibit interactions between the target bound to the agent of the particle and cell surfaces. The representations of the particles, protrusions, agent, and bound target in FIG. 3 are not necessarily shown to scale.

Particles comprising a plurality of reactive groups may thus be linked to an agent (e.g., an antibody, Fab, scFv, or ligand of a cell-surface receptor) to engineer particles that selectively bind soluble forms of a target (e.g., an antigen and/or soluble form of a cell-surface receptor) but that do not appreciably bind membrane-bound forms of the target. Such particles may be utilized in vivo or in vitro, for example, to reduce the concentration of a soluble target in a fluid without exposing the agent to membrane-bound forms of the target.

1. Biomolecule

The soluble biomolecule is, generally, a first member of a specific binding pair. As used herein, a "binding partner," "specific binding partner," or a "member of a specific binding pair," generally comprises any member of a pair of binding members that bind to each other with substantial affinity and specificity. A pair of binding partners may bind to one another to the substantial exclusion of at least most or at least substantially all other components of a sample, and/or may have a dissociation constant of less than about $10^{-4}$, $10^{-5}$, $10^{-6}$, $10^{-7}$, or $10^{-8}$M, among others. A pair of binding partners may "fit" together in a predefined manner that relies on a plurality of atomic interactions to cooperatively increase specificity and affinity. Binding partners may be derived from biological systems (e.g., receptor-ligand interactions), chemical interactions, and/or by molecular imprinting technology, among others. Exemplary corresponding pairs of binding partners, also termed specific binding pairs, are presented in Table 1, with the designations "first" and "second" being arbitrary and interchangeable.

The term "biomolecule" as used herein, refers to any molecule that may exert an effect on a living organism. In some embodiments, the biomolecule is an atom, such as lithium or lead (e.g., the biomolecule may be a metal cation). In some embodiments, the biomolecule is not an atom or metal ion. For example, the biomolecule may be a molecule, such as an organic compound or inorganic compound. In some embodiments, the biomolecule is a drug, such as warfarin or dabigatran. The biomolecule may be a psychoactive drug, such as diacetylmorphine. The biomolecule may be a poison, toxin, or venom. The biomolecule may be an allergen. The biomolecule may be a carcinogen. The biomolecule may be the agent of a chemical weapon, such as a nerve agent. The biomolecule may be a molecule that is endogenous to the organism, such as a hormone, cytokine, neurotransmitter, soluble extracellular receptor, antibody, or soluble matrix protein. The biomolecule may be a peptide, polypeptide, protein, nucleic acid, carbohydrate, or sugar. The biomolecule may comprise a peptide, polypeptide, protein, nucleic acid, carbohydrate, or sugar. The biomolecule may be a misfolded protein. The biomolecule may be an amyloid or the soluble precursor of an amyloid. "Polypeptide," "peptide," and "protein" are used interchangeably and mean any peptide-linked chain of amino acids, regardless of length or post-translational modification. The biomolecule may be a lipid, a steroid, or cholesterol. The biomolecule may comprise a lipid, a steroid, or cholesterol. The biomolecule may be a circulating, cell-free nucleic acid, such as a circulating, cell-free RNA. The biomolecule may be a micro RNA (miRNA).

The biomolecule may be a biomolecule that is secreted by a cell (e.g., a mammalian cell). The biomolecule may be an extracellular region of a membrane protein that is susceptible to cleavage into a soluble form. The biomolecule may be a cytosolic biomolecule. For example, the biomolecule may be a cytosolic biomolecule that is released in vivo following apoptosis, or a particle may be used in an in vitro method in which the cytosolic biomolecule is free in solution.

In certain preferred embodiments, the biomolecule is a soluble biomolecule. In certain preferred embodiments, the target is a soluble biomolecule. Nevertheless, a particle may target biomolecules that are not solutes in aqueous solution, and/or that do not interact with binding partners on a cell surface. For example, a particle may specifically bind a biomolecule that is associated with a protein aggregate, such as amyloid or a prion aggregate. Such particles may provide a therapeutic benefit by disassembling the aggregate (e.g., by shifting a thermodynamic equilibrium away from aggregated states) and/or by sequestering the aggregate (e.g., to inhibit further aggregation and/or to allow for clearance of the bound aggregate). Similarly, a particle may specifically bind to crystalline calcium or hydroxyapatite. Similarly, a particle may specifically bind to a biomolecule that is associated with a virus or cell, such as a bacterial, protozoan, fungal, or yeast cell, e.g., wherein the biomolecule is not a solute in aqueous solution, but the biomolecule is partitioned into a membrane, cell wall, or capsid. Thus, a particle may sequester a pathogenic virus or cell, thereby attenuating the pathogenicity of the virus or cell. A particle may specifically bind to a biomolecule that is associated with an extracellular vesicle, such as an ectosome, exosome, shedding vesicle, or apoptotic body. A particle may specifically bind to a low-density lipoprotein, e.g., to sequester low-density lipoprotein particles.

The biomolecule may be a ligand of a cell surface receptor. The ligand may be a naturally-occurring ligand or a synthetic ligand. The ligand may be a native ligand of the receptor (e.g., a ligand that is produced by a subject in vivo) or a non-native ligand (e.g., a ligand that is introduced into the subject, such as a virus or drug). The biomolecule may be a ligand for a cytosolic receptor or a nuclear receptor.

TABLE 1

Examples of specific binding pairs.

| First Binding Partner | Second Binding Partner |
|---|---|
| Cell Surface Receptor (e.g., TNF receptor) | Natural Ligand (e.g., TNFα) |

TABLE 1-continued

Examples of specific binding pairs.

| First Binding Partner | Second Binding Partner |
| --- | --- |
| Viral Coat or Envelope Protein (e.g., HIV-1 gp120) | Corresponding Cellular Receptor (e.g., CD4) |
| Botulinum Toxin | Synaptotagmin II Cell Surface Receptor |
| Soluble Receptor (e.g., soluble TNFR or soluble IL-2 receptor) | Natural Ligand (e.g., TNFα or IL-2) |

Tumor cells are known to protect themselves from host immune surveillance by shedding soluble forms of cytokine receptors, which soluble receptors bind to the cytokines produced by immune cells in the tumor microenvironment. For example, cancer cells shed soluble forms of TNF receptor and other cytokine receptors, such as IL-2 receptor and TRAIL receptor. These soluble receptors confer a growth advantage to cancer cells by relieving the cells of the pro-apoptotic effects of the TNFα, IL-2, and TRAIL. Karpatova et al. report the shedding of the 67 kD laminin receptor by human cancer cells, which may augment tumor invasion and metastasis (J. Cell Biochem 60(2):226-234 (1996)). Thus, the particles described herein can be engineered for scavenging soluble forms of cell surface receptor proteins, e.g., for use in the treatment of cancer.

Accordingly, in some embodiments, the cell surface receptor protein is expressed by a cancer cell and/or the cell surface receptor protein is a protein shed by the cancer cell as a soluble form of the cell surface receptor protein. In some embodiments, the cell surface receptor protein, when activated, induces apoptosis (e.g., a death receptor). In some embodiments, the cell surface receptor protein is a tumor necrosis factor receptor (TNFR) protein (e.g., TNFR-1 or TNFR-2). In some embodiments, the cell surface receptor protein is a Fas receptor protein. In some embodiments, the cell surface receptor protein is a TNF-related apoptosis-inducing ligand receptor (TRAILR) protein, 4-1BB receptor protein, CD30 protein, EDA receptor protein, HVEM protein, lymphotoxin beta receptor protein, DR3 protein, or TWEAK receptor protein. In some embodiments, the cell surface receptor protein is an interleukin receptor protein, e.g., an IL-2 receptor protein. It is understood that in such embodiments, the target soluble biomolecule can be a soluble form of the cell surface receptor, e.g., shed from a cancer cell.

In some embodiments, the biomolecule is soluble Tim3 ("T-Cell Ig Mucin 3"). Soluble Tim3 (sTim3) has been implicated in autoimmune disease and cancer, and elevated sTim3 is associated with HIV infection. The association of Galectin 9 ("Gal9") and potentially other ligands with Tim3 in heterodimeric association with CEACAM1 leads to inhibition of T-cell responses, and co-blockade of Tim3 and CEACAM1 leads to anti-tumor immune response. Accordingly, the biomolecule may be sTim3 or a natural ligand for sTim3, such as Tim3L, or Gal9. A biomolecule may be a soluble isoform of CEACAM1. In this way, the particles may be adapted to scavenge sTim3 while not inhibiting interaction between Gal9 and membrane-bound Tim3 (mTim3). Similarly an agent may be sTim3, an antibody selective for sTim3 (or an antigen binding portion thereof), or a ligand for Tim3. An agent may be a natural ligand for CEACAM1 (such as Gal9 or variant thereof) or an antibody selective for either CEACAM1 or its soluble isoform. Any of the foregoing particles may be used, for example, in methods of treating cancer, methods of treating HIV infection, and methods of treating an autoimmune disease, such as graft-versus-host disease.

In some embodiments, the biomolecule may be Gal9 (Galectin 9). A particle may comprise an agent selective for Gal9, such as a natural ligand for Gal9, such as Tim3, or a variant thereof, or an antibody selective for Gal9. In this way, the particles may be adapted to scavenge Gal9 while not inhibiting interactions of membrane-bound Gal9 (mGal9) with membrane-bound Tim3 (mTim3). In some embodiments, the biomolecule may be a soluble isoform of CEACAM1 ("sCEACAM1"). An agent may be a natural ligand for sCEACAM1, such as Gal9, or a variant thereof, or an antibody selective for either CEACAM1 or a soluble isoform of CEACAM1.

In some embodiments, the biomolecule is soluble CTLA4. Soluble CTLA4 ("sCTLA4") has been implicated in cancer, and antibodies active against sCTLA4, but not against membrane bound CTLA4 ("mCTLA4"), are efficacious in animal models of cancer. In some embodiments, the biomolecule is sCTLA4. An agent may be a natural ligand for CTLA4, such as soluble B7-1 or soluble B7-2, or a variant thereof, or an antibody selective for CTLA4, such as ipilimumab or ticilimumab. In this way, particles may be adapted to scavenge sCTLA4 without inhibiting interaction between ligands and mCTLA4. Thus, sCTLA4 may be removed from the tumor microenvironment ("TME") and/or the circulation outside of the TME while leaving mCTLA4 free for interaction as part of a normal immune response. Particles that target sCTLA4 may be used, for example, in methods of treating with cancer.

Soluble PD-1 ("sPD1") is implicated in autoimmune diseases such as rheumatoid arthritis. Excess sPD1 may disturb the balance between PD1 and its ligands PD-L1 and PD-L2, leading to autoimmunity. Thus, the biomolecule may be sPD1. An agent may be a natural ligand for sPD1, such as PD-L1, PD-L2, or a variant thereof, or an antibody selective for PD1, such as a PD1 blockade drug, for example, nivolumab, pidilizumab, or pembrolizumab (Keytruda®). Thus, a particle may be adapted to scavenge sPD1 without inhibiting an interaction of PD-L1 or PD-L2 with membrane-bound PD1. Such particles may be used, for example, in methods of treating autoimmune diseases, such as arthritis.

LAG3 is a T-cell surface receptor that, when bound by its ligand, results in inhibition. Soluble forms of LAG3 ("sLAG3") correlate with autoimmunity, for example, in Type I diabetes and in other autoimmune diseases. The biomolecule may be sLAG3. An agent may be a natural ligand for sLAG3, or a variant thereof, or an antibody selective for sLAG3. Thus, a particle may adapted to scavenge sLAG3 without inhibiting interactions between ligands and membrane-bound LAG3. Such particles may be used, for example, in methods of treating an autoimmune disease, such as type I diabetes.

The biomolecule may be TNFα. The agent may comprise an anti-TNFα antibody, such as infliximab, adalimumab, cerolizumab, afelimomab, nerelimomab, ozoralizumab, or golimumab, or an the agent may comprise the antigen-binding portion of an anti-TNFα antibody. The agent may be etanercept. The agent may be a soluble receptor for TNFα (sTNF-R or a variant thereof). Particles targeting TNFα may be particularly useful for treating or preventing various autoimmune diseases, such as ankylosing spondylitis, Crohn's disease, hidradenitis suppurativa, psoriasis, plaque psoriasis, psoriatic arthritis, refractory asthma, juvenile idiopathic arthritis, ulcerative colitis, and rheumatoid arthritis.

Particles targeting TNFα may also be useful for treating or preventing Alzheimer's disease, cardiovascular disease, type II diabetes, muscular dystrophy, and obesity, in addition to other diseases and conditions.

The biomolecule may be β2 microglobulin (B2M). The agent may be an anti-B2M antibody. Particles targeting B2M may be useful for treating or preventing memory loss, cognitive decline, peripheral arterial disease, dialysis-related amyloidosis, chronic lymphocytic leukaemia, multiple myeloma, and lymphoma, in addition to other diseases and conditions.

The biomolecule may be CCL2 (chemokine (C—C motif) ligand 2). The agent may be an anti-CCL2 antibody. Particles targeting CCL2 may be useful for treating or preventing Alzheimer's disease, atherosclerosis, ischemia (e.g., ischemic stroke), epilepsy, multiple sclerosis, psoriasis, rheumatoid arthritis, glomerulonephritis, and traumatic brain injury, in addition to other diseases and conditions.

The biomolecule may be CCL11 (C—C motif chemokine 11; eotaxin 1). The agent may be an anti-CCL11 antibody. Particles targeting CCL11 may be useful for treating or preventing memory loss and cognitive decline, in addition to other diseases and conditions.

The biomolecule may be CCL19. The agent may be an anti-CCL19 antibody. Particles targeting either CCL19 may be useful for treating or preventing aging and cognitive decline, in addition to other diseases and conditions.

The biomolecule may be interferon gamma (INFγ). The agent may comprise an anti-INFγ antibody, such as fontolizumab, or a soluble INFγ receptor (sINFγR). The biomolecule may be soluble INFγ receptor. The agent may comprise INFγ or an anti sINFγR antibody. Particles targeting interferon gamma may be particularly useful for treating or preventing autoimmune disease, such as Crohn's disease, rheumatoid arthritis, and psoriasis, in addition to other diseases and conditions.

The biomolecule may be clusterin (e.g., secretory clusterin, isoform 2). The agent may comprise an anti-clusterin antibody, or an antigen-binding portion thereof. Particles targeting clusterin may be useful for treating or preventing cancer (e.g., head and neck cancer, renal cell cancer, colorectal cancer, endometrial cancer, ovarian cancer, breast cancer, prostate cancer, pancreatic cancer, lung cancer, hepatocellular cancer, or melanoma), renal disease (e.g., nephropathic cystinosis), Fanconi syndrome, glomerulonephritis, atherosclerosis, and myocardial infarction, in addition to other diseases and conditions.

The biomolecule may be high mobility group box 1 (HMGB1). The agent may comprise an anti-HMGB1 antibody, or an antigen-binding portion thereof. The biomolecule may be a heat shock protein (e.g., HSP60, HSP70, HSP90). The agent may comprise an anti-HSP antibody, or an antigen-binding portion thereof. The biomolecule may be a peroxiredoxin (e.g., peroxiredoxin 1 or peroxiredoxin 2). The agent may comprise an anti-peroxiredoxin antibody, or an antigen-binding portion thereof.

The agent may be the extracellular portion of a scavenger receptor, such as a class A scavenger receptor (e.g., SCARA1 (Macrophage scavenger receptor 1; MSR1; CD204), SCARA2 (Macrophage receptor; MARCO), SCARA3, SCARA4 (COLEC12), SCARA5), class B scavenger receptor (e.g., SCARB1, SCARB2, SCARB3 (CD36)), CD68, mucin, or lectin-like oxidized LDL receptor-1 (LOX-1).

The biomolecule may be insulin-like growth factor 1 (IGF-1) or an insulin-like growth factor binding protein (e.g., IGFBP-1, IGFBP-2, IGFBP-3, IGFBP-4, IGFBP-5, IGFBP-6). The agent may be insulin-like growth factor 1 (IGF-1) or an insulin-like growth factor binding protein (e.g., IGFBP-1, IGFBP-2, IGFBP-3, IGFBP-4, IGFBP-5, IGFBP-6). The agent may be an antibody, or an antigen-binding portion thereof, that selectively binds insulin-like growth factor 1 (IGF-1) or an insulin-like growth factor binding protein (e.g., IGFBP-1, IGFBP-2, IGFBP-3, IGFBP-4, IGFBP-5, IGFBP-6).

The agent may be an antibody that selectively binds an extracellular epitope of CD63, CD9, or CD81. Particles targeting CD63, CD9, and/or CD81 may be particularly useful for scavenging extracellular vesicles, such as an ectosome, exosome, shedding vesicle, or apoptotic body. Particles that scavenge various extracellular vesicles may be particularly useful for treating or preventing cancer (e.g., cancers having a disease progression that correlates with the shedding of vesicles).

The biomolecule may be CXCL1, CXCL2, CXCL3, CXCL4, CXCL4L1, CXCL5, CXCL6, CXCL7, CXCL8, CXCL9, CXCL10, CXCL11, CXCL12, CXCL13, CXCL14, CXCL16, CXCL17, CCL1, CCL2, CCL3, CCL3L1, CCL3L3, CCL4, CCL4L1, CCL4L2, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, or CX3CL1 (see, e.g., Zlotnik, A. and Yoshie, O., Immunity, 36(5):705 (2012)). The agent may comprise an antibody (or an antigen-binding portion thereof) that specifically binds CXCL1, CXCL2, CXCL3, CXCL4, CXCL4L1, CXCL5, CXCL6, CXCL7, CXCL8, CXCL9, CXCL10, CXCL11, CXCL12, CXCL13, CXCL14, CXCL16, CXCL17, CCL1, CCL2, CCL3, CCL3L1, CCL3L3, CCL4, CCL4L1, CCL4L2, CCL5, CCL7, CCL8, CCL11, CCL13, CCL14, CCL15, CCL16, CCL17, CCL18, CCL19, CCL20, CCL21, CCL22, CCL23, CCL24, CCL25, CCL26, CCL27, CCL28, XCL1, XCL2, or CX3CL1.

The biomolecule may be interleukin 1, interleukin 1 alpha, interleukin 1 beta, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, interleukin 16, interleukin 17, interleukin 18, interleukin 19, interleukin 20, interleukin 21, interleukin 22, interleukin 23, interleukin 24, interleukin 25, interleukin 26, interleukin 27, interleukin 28, interleukin 29, interleukin 30, interleukin 31, interleukin 32, interleukin 33, interleukin 35, or interleukin 36. The agent may comprise an antibody (or an antigen-binding portion thereof) that specifically binds interleukin 1, interleukin 1 alpha, interleukin 1 beta, interleukin 2, interleukin 3, interleukin 4, interleukin 5, interleukin 6, interleukin 7, interleukin 8, interleukin 9, interleukin 10, interleukin 11, interleukin 12, interleukin 13, interleukin 14, interleukin 15, interleukin 16, interleukin 17, interleukin 18, interleukin 19, interleukin 20, interleukin 21, interleukin 22, interleukin 23, interleukin 24, interleukin 25, interleukin 26, interleukin 27, interleukin 28, interleukin 29, interleukin 30, interleukin 31, interleukin 32, interleukin 33, interleukin 35, or interleukin 36. The agent may comprise a soluble interleukin-2 receptor, soluble interleukin-3 receptor, soluble interleukin-4 receptor, soluble interleukin-5 receptor, soluble interleukin-6 receptor, soluble interleukin-7 receptor, soluble interleukin-9 receptor, soluble interleukin-10 receptor, soluble interleukin-11 receptor, soluble interleukin-12 receptor, soluble interleukin-13 receptor, soluble interleukin-15 receptor, soluble interleukin-20 receptor, soluble interleukin-21 receptor, soluble interleukin-22 receptor, soluble interleukin-23 receptor, soluble interleukin-27 receptor, or soluble interleukin-28 receptor. The agent may be soluble ST2, which binds interleukin 33.

The biomolecule may be a soluble interleukin-2 receptor, soluble interleukin-3 receptor, soluble interleukin-4 receptor, soluble interleukin-5 receptor, soluble interleukin-6 receptor, soluble interleukin-7 receptor, soluble interleukin-9 receptor, soluble interleukin-10 receptor, soluble interleukin-11 receptor, soluble interleukin-12 receptor, soluble interleukin-13 receptor, soluble interleukin-15 receptor, soluble interleukin-20 receptor, soluble interleukin-21 receptor, soluble interleukin-22 receptor, soluble interleukin-23 receptor, soluble interleukin-27 receptor, or soluble interleukin-28 receptor. The agent may comprise an antibody (or an antigen-binding portion thereof) that specifically binds soluble interleukin-2 receptor, soluble interleukin-3 receptor, soluble interleukin-4 receptor, soluble interleukin-5 receptor, soluble interleukin-6 receptor, soluble interleukin-7 receptor, soluble interleukin-9 receptor, soluble interleukin-10 receptor, soluble interleukin-11 receptor, soluble interleukin-12 receptor, soluble interleukin-13 receptor, soluble interleukin-15 receptor, soluble interleukin-20 receptor, soluble interleukin-21 receptor, soluble interleukin-22 receptor, soluble interleukin-23 receptor, soluble interleukin-27 receptor, or soluble interleukin-28 receptor. The agent may be interleukin 2, interleukin 3, interleukin 4, interleukin 5, interleukin 6, interleukin 7, interleukin 9, interleukin 10, interleukin 11, interleukin 12, interleukin 13, interleukin 15, interleukin 20, interleukin 21, interleukin 22, interleukin 23, interleukin 27, or interleukin 28.

The biomolecule may be epinephrine, norepinephrine, melatonin, serotonin, triiodothyronine, or thyroxine. The biomolecule may be a prostaglandin (e.g., prostacyclin I2 (PGI2), prostaglandin E2 (PGE2), prostaglandin F2α (PGF2α)), a leukotriene, prostacyclin, or thromboxane. The biomolecule may be testosterone, dehydroepiandrosterone (DHEA), androstenedione, dihydrotestosterone (DHT), aldosterone, estrone, estradiol, estriol, progesterone, cortisol, calcitriol, or calcidiol.

The biomolecule may be amylin, adiponectin, adrenocorticotropic hormone, angiotensinogen, angiotensin I, angiotensin II, antidiuretic hormone (vasopressin), apelin, atrial-natriuretic peptide, brain natriuretic peptide, calcitonin, chemerin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (somatomedin, e.g., IGF-I), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (thyrotropin), thyrotropin-releasing hormone, or vasoactive intestinal peptide. The agent may comprise an antibody (or an antigen-binding portion thereof) that specifically binds amylin, adiponectin, adrenocorticotropic hormone, apelin, angiotensinogen, angiotensin I, angiotensin II, antidiuretic hormone (vasopressin), atrial-natriuretic peptide, brain natriuretic peptide, calcitonin, chemerin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor (somatomedin, e.g., IGF-I), leptin, lipotropin, luteinizing hormone, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone (thyrotropin), thyrotropin-releasing hormone, or vasoactive intestinal peptide.

The biomolecule may be vascular endothelial growth factor-A (VEGF-A). The agent may comprise an antibody that specifically binds VEGF-A, such as bevacizumab or brolucizumab, or an antigen-binding portion thereof, such as ranibizumab. For example, the agent may be aflibercept. Particles that target VEGF-A may be particularly useful for treating or preventing macular degeneration (e.g., wet macular degeneration), proliferative diabetic retinopathy, neovascular glaucoma, macular edema, cancer (e.g., colorectal cancer, lung cancer, prostate cancer, breast cancer, renal cancer, brain cancer), bronchial asthma, diabetes mellitus, ischemic cardiomyopathy, and myocardial ischemia, in addition to other conditions and diseases.

The biomolecule may be a soluble vascular endothelial growth factor receptor, such as soluble vascular endothelial growth factor receptor 1 (soluble VEGFR-1), soluble vascular endothelial growth factor receptor 2 (soluble VEGFR-2), or soluble vascular endothelial growth factor receptor 3 (soluble VEGFR-3). The agent may be an antibody, or antigen-binding portion thereof, that selectively binds a soluble VEGF receptor, such as alacizumab, icrucumab, or ramucirumab. The agent may be a ligand of a VEGF receptor, such as VEGF-A, VEGF-B, VEGF-C, VEGF-D, or placental growth factor (PGF). Particles targeting soluble VEGF receptors may be particularly useful for treating or preventing cancer, in addition to other disease and conditions.

The biomolecule may be a member of the epidermal growth factor family, such as epidermal growth factor (EGF), heparin-binding EGF-like growth factor (HB-EGF), transforming growth factor-α (TGF-α), amphiregulin (AR), epiregulin (EPR), epigen, betacellulin (BTC), neuregulin-1 (NRG1), neuregulin-2 (NRG2), neuregulin-3 (NRG3), or neuregulin-4 (NRG4). The agent may be an antibody, or antigen-binding portion thereof, that selectively binds EGF, HB-EGF, TGF-α, AR, EPR, epigen, BTC, NRG1, NRG2, NRG3, or NRG4. The agent may comprise a soluble EGF receptor, such as soluble EGF receptor, soluble HER2, or soluble HER3. Particles targeting members of the epidermal growth factor family may be particularly useful for treating or preventing cancer, in addition to other conditions and diseases.

The biomolecule may be a soluble epidermal growth factor receptor (EGF receptor), such as soluble EGF receptor, soluble human epidermal growth factor receptor 2 (soluble HER2) or soluble human epidermal growth factor receptor 3 (soluble HER3). The agent may be an antibody, or antigen-binding portion thereof, that selectively binds a soluble EGF receptor, such as cetuximab, futuximab, imgatuzumab, matuzumab, necitumumab, nimotuzumab, panitumumab, zalutumumab, duligotumab, patritumab, ertumaxomab, pertuzumab, or trastuzumab. The agent may be a ligand of an EGF receptor, such as an EGF family member as described above. Particles targeting soluble EGF receptors may be particularly useful for treating or preventing cancer, in addition to other disease and conditions.

The biomolecule may be an IgE antibody. The agent may comprise an anti-IgE antibody, such as omalizumab or talizumab, or an antigen-binding portion thereof. The agent may be the extracellular portion of FcεRI. Particles that target IgE antibodies may be particularly useful for treating chronic spontaneous urticarial and allergic asthma, in addition to other conditions and diseases.

The biomolecule may be proprotein convertase subtilisin/kexin type 9 (PCSK9). The agent may be an anti-PCSK9 antibody, such as alirocumab, lodelcizumab, ralpancizumab, or evolocumab, or an antigen-binding portion thereof. Particles targeting PCSK9 may be particularly useful for treating or preventing hypercholesterolemia, atherosclerosis, ischemia, and myocardial infarction, in addition to other conditions and diseases.

The biomolecule may be adrenomedullin, brain-derived neurtrophic factor, erythropoietin, fibroblast growth factor, hepatoma-derived growth factor, glucose-6-phosphate isomerase, keratinocyte growth factor, macrophage migration inhibitory factor, neurotrophin (nerve growth factor, brain-derived neurotrophic factor, neurotrophin-3, neurotrophin-4), platelet-derived growth factor, stem cell factor, thrombopoietin, T-cell growth factor, vascular endothelial growth factor (VEGF-A, VEGF-B, VEGF-C, VEGF-D, placental growth factor (PGF)), or renalase. The agent may comprise an antibody, or antigen-binding portion thereof, that selectively binds adrenomedullin, brain-derived neurtrophic factor, erythropoietin, fibroblast growth factor, hepatoma-derived growth factor, glucose-6-phosphate isomerase, keratinocyte growth factor, macrophage migration inhibitory factor, neurotrophin (nerve growth factor, brain-derived neurotrophic factor, neurotrophin-3, neurotrophin-4), platelet-derived growth factor, stem cell factor, thrombopoietin, T-cell growth factor, vascular endothelial growth factor (VEGF-A, VEGF-B, VEGF-C, VEGF-D, placental growth factor (PGF)), or renalase.

The biomolecule may be soluble tropomyosin receptor kinase B (soluble TrkB). The agent may be an anti-TrkB antibody, or an antigen-binding portion thereof. The biomolecule may be soluble tropomyosin receptor kinase A (soluble TrkA). The agent may be an anti-TrkA antibody, or an antigen-binding portion thereof. The agent may be brain-derived neurotrophic factor.

The biomolecule may be angiopoietin (e.g., angiopoietin 1, angiopoietin 2, angiopoietin 3, or angiopoietin 4) or an angiopoietin like protein (e.g., angiopoietin-like 1, angiopoietin-like 2, angiopoietin-like 3, angiopoietin-like 4, angiopoietin-like 5, angiopoietin-like 6, or angiopoietin-like 7). The agent may be an antibody that selectively binds to angiopoietin (e.g., angiopoietin 1, angiopoietin 2, angiopoietin 3, or angiopoietin 4) or an angiopoietin like protein (e.g., angiopoietin-like 1, angiopoietin-like 2, angiopoietin-like 3, angiopoietin-like 4, angiopoietin-like 5, angiopoietin-like 6, or angiopoietin-like 7).

The biomolecule may be a hedgehog protein (e.g., sonic hedgehog). The agent may be an antibody that selectively binds a hedgehog protein. Particles targeting hedgehog proteins may be particularly useful for treating or preventing cancer, such as pancreatic cancer, cerebellar cancer, and medulloblastomas, in addition to other conditions and diseases.

The biomolecule may be a soluble human leukocyte antigen (HLA) protein (e.g., soluble HLA-A, HLA-B, HLA-C, HLA-D, HLA-E, HLA-F, OR HLA-G (see, e.g., Bassani-Sternberg, M. et al., Proceedings National Academy Sciences USA 107(44):18769 (2010))). The agent may be an antibody that selectively binds a soluble human leukocyte antigen (HLA) protein. The agent may be a soluble killer cell immunoglobulin-like receptor. Particles that target a soluble HLA may be particularly useful for treating or preventing cancer, in addition to other diseases and conditions.

The biomolecule may be a soluble UL16-binding protein isoform (e.g., a soluble RAET1 (ULBP1; RAET1E2), soluble RAET1H (ULBP2), soluble RAET1N (ULBP3), soluble RAET1E (ULBP4), soluble RAET1G (ULBP5), or soluble RAET1L (ULBP6)). The agent may be an antibody that specifically binds a soluble UL16-binding protein isoform, or an antigen-binding portion thereof. The agent may be soluble NKG2D receptor (see, e.g., PCT Patent Application Publication No. WO 2006/024367, hereby incorporated by reference in its entirety).

The biomolecule may be soluble MIC-A or soluble MIC-B (see, e.g., Groh, V. et al., Nature 419(6908):734 (2002)). The agent may be an anti-MIC-A antibody or an anti-MIC-B antibody, or an antigen binding portion of either antibody. The agent may be soluble NKG2D receptor (see, e.g., PCT Patent Application Publication No. WO 2006/024367, hereby incorporated by reference in its entirety).

The agent may be a soluble natural cytotoxicity receptor (see, e.g., Jarahian, M. et al. PloS Pathogens 7(8): e1002195 (2011)).

The biomolecule may be soluble C-type lectin domain family 2 member D (soluble CLEC2D; soluble Lectin Like Transcript-1 (LLT1)) (see, e.g., Chalan, P. et al., PloS One 10(7): e0132436 (2015)). The agent may be an antibody that selectively binds soluble LLT1. Particles that target a soluble LLT1 may be particularly useful for treating or preventing autoimmune diseases, such as rheumatoid arthritis, in addition to other diseases and conditions.

The biomolecule may be soluble CD16 (see, e.g., Hoover, R. G., J Clinical Investigation 95:241 (1995)). The agent may be an antibody that selectively binds a soluble CD16. Particles that target soluble CD16 may be particularly useful for treating or preventing cancer, in addition to other diseases and conditions.

The biomolecule may be plasminogen activator inhibitor-1 (PAI-1), plasminogen activator inhibitor-1 (PAI-2), tissue plasminogen activator, urokinase, plasminogen, thrombin, or α2-macroglobulin. The agent may be an antibody that selectively binds plasminogen activator inhibitor-1 (PAI-1), plasminogen activator inhibitor-1 (PAI-2), tissue plasminogen activator, urokinase, plasminogen, thrombin, or α2-macroglobulin.

The biomolecule may be Factor XII, Factor XIIa, Factor XI, Factor XIa, Factor IX, Factor IXa, Factor X, Factor Xa, Factor VII, Factor VIIa, Factor XIII, Factor XIIIa, Factor V, prothrombin, thrombin, von Willebrand factor, thromboxane A2, fibrinogen, or fibrin. The agent may be an antibody that selectively binds to Factor XII, Factor XIIa, Factor XI, Factor XIa, Factor IX, Factor IXa, Factor X, Factor Xa, Factor VII, Factor VIIa, Factor XIII, Factor XIIIa, Factor V, prothrombin, thrombin, von Willebrand factor, thromboxane A2, fibrinogen, or fibrin.

The biomolecule may be a serpin (e.g., al-antitrypsin, antitrypsin-related protein, α1-antichymotrypsin, kallistatin, protein C inhibitor, transcortin, thyroxine-binding globulin, angiotensinogen, centerin (GCET1), protein Z-related protease inhibitor, vaspin, antithrombin, heparin cofactor II, plasminogen activator inhibitor 1, glia derived nexin (protease nexin I), pigment epithelium derived factor, α2-antiplasmin, complement 1-inhibitor, neuroserpin, plasminogen activator inhibitor, 2SERPINA1, or SERPINA2). The agent may comprise an antibody that selectively binds a serpin, or an antigen-binding portion thereof.

The biomolecule may be soluble ST2. The agent may be interleukin 33 or an antibody that specifically binds soluble ST2 (or a fragment thereof). Particles that target soluble ST2 may be particularly useful for treating or preventing heart disease, myocardial infarction, acute coronary syndrome, and heart failure, in addition to other disease and conditions.

The biomolecule may be myostatin (growth differentiation factor 8 (GDF-8)). The agent may be an anti-myostatin antibody, such as stamulumab or trevogrumab. The agent may be an activin receptor or a myostatin-binding portion thereof, e.g., the agent may be soluble activin type IIB receptor. Particles targeting myostatin may be particularly useful for treating muscular dystrophy, cachexia, sarcopenia, and various forms of muscle loss (such as zero-gravity muscle loss), in addition to other diseases and conditions.

The biomolecule may be ghrelin. The agent may be an anti-ghrelin antibody. Particles targeting ghrelin may be particularly useful for treating or preventing obesity, Prader-Willi syndrome, addiction, alcoholism, and leptin resistance (e.g., genetic leptin resistance).

The biomolecule may be sLR11 (soluble SORL1; soluble SORLA; soluble SORLA1). The agent may be an anti-sLR11 antibody. Particles targeting sLR11 may be particularly useful for treating or preventing obesity, in addition to other diseases and conditions.

The biomolecule may be TGF-β (transforming growth factor beta, e.g., TGF-β1, TGF-β2, or TGF-β3). The agent may be an anti-TGF-β antibody, such as fresolimumab, lerdelimumab, or metelimumab. The agent may comprise the TGF-β binding domain of a TGF-β receptor. The agent may be $LTBP_1$ (latent-transforming growth factor beta-binding protein 1), 14-3-3-protein epsilon (tyrosine 3-monooxygenase/tryptophan 5-monooxygenase activation protein, epsilon; YWHAE), or eukaryotic translation initiation factor 3 subunit I (EIF3I), each of which binds to TGF-β. Particles targeting TGF-β may be particularly useful for treating or preventing scleroderma, idiopathic pulmonary fibrosis, renal disease, focal segmental glomerulosclerosis, keratoconus, Marfan syndrome, Alzheimer's disease, cognitive decline, traumatic brain injury, muscle wasting, and cancer (e.g., kidney cancer and melanoma), in addition to other diseases and conditions.

The biomolecule may be Wnt (e.g., Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, or Wnt16). The agent may be an anti-Wnt antibody. Particles targeting Wnt may be particularly useful for treating or preventing obesity, type II diabetes, atherosclerosis, calcific aortic valve stenosis, heart attack, heart failure, stroke, and cancer (e.g., breast cancer, colorectal cancer, esophageal cancer, melanoma, prostate cancer, lung cancer, non-small cell lung cancer, mesothelioma, sarcoma, glioblastoma, or ovarian cancer), in addition to other diseases and conditions.

The biomolecule may be a soluble Notch ligand (e.g., soluble Jagged1, soluble Jagged2, soluble Delta-like ligand 1 (DLL1), soluble Delta-like ligand 3 (DLL3), and Delta-like ligand 4 (DLL4)). The agent may be an anti-Notch ligand antibody, such as demcizumab or enoticumab, or a soluble Notch receptor (e.g., soluble NOTCH1, NOTCH2, NOTCH3, or NOTCH4) or a variant thereof. Particles targeting soluble Notch ligands may be particularly useful for treating or preventing atherosclerosis, calcific aortic valve stenosis, heart attack, heart failure, stroke, and cancer (e.g., breast cancer, pancreatic cancer renal cell carcinoma, non-small cell lung cancer, and solid tumors), in addition to other diseases and conditions.

The biomolecule may be a soluble Notch receptor (e.g., soluble NOTCH1, NOTCH2, NOTCH3, or NOTCH4). The agent may be an anti-Notch receptor antibody, such as tarextumab or brontictuzumab, or a soluble Notch ligand. Particles targeting soluble Notch receptors may be particularly useful for treating or preventing atherosclerosis, calcific aortic valve stenosis, heart attack, heart failure, stroke, and cancer (e.g., breast cancer, pancreatic cancer renal cell carcinoma, non-small cell lung cancer, and solid tumors), in addition to other diseases and conditions.

The target may be hydroxyapatite or calcium (e.g., crystalline calcium). The agent may be a chelating agent such as ethylene diamine tetraacetic acid (EDTA), diethylene triamine pentaacetic acid (DTPA), sodium thiosulfate (STS), inositol hexaphosphate, or citric acid. Particles targeting hydroxyapatite or calcium may be particularly useful for treating or preventing atherosclerosis, calcific aortic valve stenosis, and calcific tendinitis, in addition to other diseases and conditions.

In some embodiments, the biomolecule is an autoantibody. An autoantibody is an antibody produced by a subject that specifically binds an antigen produced by the subject. Autoantibodies are associated with many different disease states, including lupus. Additionally, the induction of new autoantibodies may be associated with a therapeutic intervention, e.g., resulting in drug-induced lupus. Thus, a composition comprising a plurality of particles comprising an agent that selectively binds one or more autoantibodies may be used, for example, in a method of treating or preventing lupus (e.g., drug-induced lupus). The biomolecule may be, for example, a double-stranded DNA autoantibody or an anti-nuclear autoantibody.

A particle that targets an autoantibody may comprise an agent that is the antigen of the autoantibody.

The biomolecule may be an anti-β adrenoceptor autoantibody or an anti-M2 muscarinic receptor autoantibody, e.g., for preventing or treating idiopathic dilated cardiomyopathy. In particular, a particle that targets an anti-β adrenoceptor autoantibody or an anti-M2 muscarinic receptor autoantibody may be administered to a subject with Chagas' disease, which correlates with the induction of such autoantibodies (see, e.g., Herda, L. R. et al., Br J Pharmacol 166(3)847 (2012)). The biomolecule may be an anti-alpha-1-adrenergic receptor autoantibody, e.g., for treating or preventing hypertension (see, e.g., Luther, H. P. et al., Hypertension 29(2): 678 (1997)). The biomolecule may be an anti-muscarinic type 3 receptor autoantibody, e.g., for use in treating or preventing Sjögren's syndrome (see, e.g., Lee, B. H. et al., PloS One 8(1):e53113 (2013)).

Autoantibodies against hormones and cytokines may buffer the concentration of hormones and cytokines, for example by reversibly binding to them to control the concentration of free, active species. Deviations from healthy autoantibody levels may contribute to diseases arising from loss of cytokine or hormonal homeostasis. For example, anti-IFNγ autoantibodies may induce disseminated non-tuberculosis mycobacterial infections, anti-IL-17 autoantibodies are associated with the development of chronic mucosal candidiasis, and anti-IL-6 autoantibodies are associated with severe staphylococcal or streptococcal infections. Autoantibodies to the hunger hormone ghrelin may mediate the effective concentration of ghrelin available to bind to ghrelin receptor GHSR1.

In some embodiments, the biomolecule is an autoantibody. For example, the autoantibody may be an anti-IFNγ, anti-IL-17, anti-IL-6, or anti-ghrelin autoantibody. In some embodiments, the agent is the natural ligand of an autoantibody (e.g., an antigen targeted by the autoantibody). For example, the agent may be IFNγ, IL-17, IL-6, or ghrelin. In some embodiments, the invention relates to a method of treating a patient with a disease of dysregulation of a cytokine, such as an autoimmune disease. In some embodiments, the invention relates to a method of treating a patient with metabolic disorder, such as obesity.

Activin binding to activin type IIB receptor ActRIIB leads to muscle wasting in models of cachexia. Excessive activin levels in serum are associated with muscle wasting and fibrosis in models of cachexia, which may be reversed by antibodies that block activin A and B/ActRIIB signalling, and elevated activin levels are found in serum of cancer patients. Sarcopenia is a progressive condition of loss of muscle mass in aging and has also been associated with excessive activin signalling. The biomolecule may thus be activin (e.g., activin A or activin B). The agent may be a natural ligand for an activin, such as an activin receptor protein such as ActRIIB or a variant thereof, or an antibody against an activin. The agent may be myostatin. In some embodiments, the invention relates to a method of treating a patient a muscle-wasting disease, such as cachexia or sarcopenia.

A skilled artisan will also appreciate that the particles described herein are also useful for scavenging a wider variety of targets whose biological activity may be, e.g., undesirable. For example, the particles can be engineered to bind to components of viral capsids or envelopes to thereby sequester virus from the blood of a subject. The particles may be, in some embodiments, engineered to bind and sequester toxins (e.g., bacterial toxins, plant toxins, and zootoxins, such as one or more components of snake venom) in the circulation of a subject. In some embodiments, the particles can be engineered to bind to and sequester small molecules (e.g., psychoactive drugs or small molecular toxins) from the circulation of a subject. In such embodiments, the particles can be useful to remove toxins from the body, e.g., following a snake or insect bite. In some embodiments, the particles can be used for treating, preventing, delaying the onset, or reducing the severity of, anaphylactic shock in a subject (e.g., by scavenging the antigen giving rise to the anaphylactic immune response).

In some embodiments, the target is associated with a virus, e.g., a viral structural protein (such as a viral capsid or viral envelope protein) that is bound by the agent. In such embodiments, the particles are useful as anti-viral therapies, e.g., for a subject infected with a virus or at risk of being infected with a virus. A virus may be an enveloped or non-enveloped virus.

In some embodiments, the soluble biomolecule is a small molecule or macromolecule. In some embodiments, the longest dimension of the soluble biomolecule is no greater than 600 nm (e.g., less than 550, 500, 450, 400, 350, 300, 250, 200, 150, 100, 50, or 25 nm). For example, the biomolecule may have a molecular radius of about 1 Å to about 1 µm, such as about 1 Å to about 100 nm, about 1 Å to about 20 nm, about 1 nm to about 1 µm, about 1 nm to about 100 nm, or about 1 nm to about 20 nm. The biomolecule may have a molecular weight of about 3 amu to about $10^7$ amu, such as about 100 amu to about $10^7$ amu, about 3 amu to about $10^6$ amu, about 3 amu to about $10^5$ amu, about 100 amu to about $10^6$ amu, or about 400 amu to about $10^6$ amu. The biomolecule may have a molecular weight of about $10^5$ amu to about $10^7$ amu.

The terms "specific binding," "specifically binds," "selective binding," "selectively binds," and like grammatical terms, as used herein, refer to two molecules forming a complex that is relatively stable under physiologic conditions. Typically, binding is considered specific when the association constant ($k_a$) is higher than $10^6 M^{-1} s^{-1}$. Thus, a first member of a specific binding pair can specifically bind to the second member of the binding pair with a $k_a$ of at least (or greater than) $10^6 M^{-1} s^{-1}$ (e.g., at least or greater than $10^7$, $10^8$, $10^9$, $10^{10}$, $10^{11}$, $10^{12}$, $10^{13}$, $10^{14}$, or $10^{15}$ $M^{-1} s^{-1}$ or higher). In some embodiments, a selective interaction has a dissociation constant ($k_d$) of less than or equal to $10^{-3}$ $S^{-1}$ (e.g., $8 \times 10^{-4}$, $5 \times 10^{-4}$, $2 \times 10^{-4}$, $10^{-4}$, or $10^{-5}$ $s^{-1}$).

Specific binding does not refer to an interaction that is primarily driven by a non-specific electrostatic interaction or a non-specific hydrophobic interaction, which may have a favorable association constant. For example, nucleic acids, which are negatively charged, may bind to a cationic particle with a favorable association constant, independent of a specific interaction, and such binding is not "specific binding" as defined herein. Similarly, a lipid may bind to a hydrophobic particle with a favorable association constant, independent of a specific interaction, and such binding is not "specific binding" as defined herein.

In some embodiments, the biomolecule and the particle have the same charge at physiological pH (~7.4). For example, the biomolecule may have a negative charge and the particle may have a negative charge or the biomolecule may have a positive charge and the particle may have a positive charge. In some embodiments, the biomolecule and the particle have opposite charges at physiological pH. For example, the biomolecule may have a positive charge and the particle may have a negative charge or the biomolecule may have a negative charge and the particle may have a positive charge. In some embodiments, the biomolecule has a neutral charge at physiological pH and/or the particle has a neutral charge at physiological pH.

The biomolecule may have an isoelectric point of about 0 to about 14. Nucleic acids have an isoelectric point of about 4 to about 7, and thus, the biomolecule may have an isoelectric point of about 4 to about 7. Proteins generally have an isoelectric point of about 4 to about 10, and thus, the biomolecule may have an isoelectric point of about 4 to about 10. Nevertheless, unmodified peptides and proteins may have isoelectric points ranging from about 2.5 (based on aspartate; pI~2.8) to about 11 (based on arginine; pI~11), although proteins with isoelectric points falling outside of this range are known. Accordingly, the biomolecule may have an isoelectric point ranging from about 2.5 to about 11. Secreted proteins and the soluble, extracellular portions of membrane proteins typically have a slight negative charge at physiological pH, and thus, the biomolecule may have an isoelectric point of about 4 to about 7, such as about 4 to about 6. The biomolecule may have an isoelectric point of about 0 to about 4, about 2 to about 6, about 4 to about 8, about 6 to about 10, about 8 to about 12, or about 10 to about 14. The biomolecule may have an isoelectric point of about 0 to about 2, about 1 to about 3, about 2 to about 4, about 3 to about 5, about 4 to about 6, about 4 to about 6, about 5 to about 7, about 6 to about 8, about 7 to about 9, about 8 to about 10, about 9 to about 11, about 10 to about 12, about 11 to about 13, or about 12 to about 14.

In some embodiments, a selective interaction has a $K_D$ of less than $10^{-8}$, $10^{-9}$, $10^{-10}$, $10^{-11}$, or $10^{-12}$ M. The equilibrium constant $K_D$ is the ratio of the kinetic rate constants—$k_d/k_a$. In some embodiments, a selective interaction has a $K_D$ of less than $1 \times 10^{-9} M$.

As used herein, the term "interaction," when referring to an interaction between two molecules, refers to the physical contact (e.g., binding) of the molecules with one another. Generally, such an interaction results in an activity (which produces a biological effect) of one or both of said molecules. To inhibit such an interaction results in the disruption of the activity of one or more molecules involved in the interaction.

As used herein, the term "inhibiting" and grammatical equivalents thereof refer to a decrease, limiting, and/or blocking of a particular action, function, or interaction. In one embodiment, the term refers to reducing the level of a given output or parameter to a quantity (e.g., the background level of the interaction between two members of a specific binding pair) which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control. A reduced level of a given output or parameter need not, although it may, mean an absolute absence of the output or parameter. The invention does not require, and is not limited to, methods that wholly eliminate the output or parameter. Substantial inhibition can be, e.g., at least 50% (e.g., 55, 60, 65, 70, 75, 80, 85, 90, or 95% or greater) inhibition of an interaction between two biomolecules (e.g., the first and second members of a binding pair).

Methods for detecting an interaction or measuring the affinity of one biomolecule for another are known in the art. For example, the binding of two biomolecules can be detected and/or quantified using a variety of techniques such as, but not limited to, BioLayer Interferometry (BLI), Western blot, dot blot, surface plasmon resonance method (SPR), enzyme-linked immunosorbent assay (ELISA), AlphaScreen® or AlphaLISA® assays, or mass spectrometry based methods.

In some embodiments, binding can be assayed using any SPR-based assays known in the art for characterizing the kinetic parameters of the interaction of two biomolecules. Any SPR instrument commercially available including, but not limited to, BIAcore Instruments (Biacore AB; Uppsala, Sweden); lAsys instruments (Affinity Sensors; Franklin, Mass.); IBIS system (Windsor Scientific Limited; Berks, UK), SPR-CELLIA systems (Nippon Laser and Electronics Lab; Hokkaido, Japan), and SPR Detector Spreeta (Texas Instruments; Dallas, Tex.) can be used in the methods described herein. (See, e.g., Mullett et al., *Methods* 22:77-91 (2000); Dong et al., *Reviews in Mol Biotech* 82:303-323 (2002); Fivash et al., *Curr Opin Biotechnol* 9:97-101 (1998); and Rich et al., *Curr Opin Biotechnol* 11:54-61 (2000)).

In some embodiments, biomolecular interactions between two biomolecules can be assayed using BLI on an Octet (ForteBio Inc.). BLI is a label-free optical analytical technique that senses binding between a ligand that is immobilized on a biosensor tip and an analyte in solution by measuring the change in the thickness of the protein layer on the biosensor tip in real-time.

In some embodiments, AlphaScreen (PerkinElmer) assays can be used to characterize binding of two biomolecules. The acronym ALPHA stands for Amplified Luminescent Proximity Homogeneous Assay. AlphaScreen is a bead-based proximity assay that senses binding between molecules attached to donor and acceptor beads by measuring the signal produced by energy transfer between the donor and acceptor beads. (See, e.g., Eglen et al., *Curr Chem Genomics* 1:2-10 (2008)).

In some embodiments, AlphaLISA® (PerkinElmer) assays can be used to characterize binding of two biomolecules. AlphaLISA is modified from the AlphaScreen assay described above to include europium-containing acceptor beads and functions as an alternative to traditional ELISA assays. (See, e.g., Eglen et al., *Curr Chem Genomics* 1:2-10 (2008)).

A variety of immunoassay techniques, including competitive and non-competitive immunoassays, can be used. The term "immunoassay" encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA), and microparticle enzyme immunoassay (META), furthermore capillary electrophoresis immunoassays (CEIA), radio-immunoassays (MA), immunoradiometric assays (IRMA), fluorescence polarization immunoassays (FPIA), and chemiluminescence assays (CL). If desired, such immunoassays can be automated. Immunoassays can also be used in conjunction with laser induced fluorescence. Liposome immunoassays, such as flow-injection liposome immunoassays and liposome immunosensors, are also suitable for use in the present invention. In addition, nephelometry assays, in which, for example, the formation of biomolecular complexes results in increased light scatter that is converted to a peak rate signal as a function of the marker concentration, are suitable for use in the methods of the present invention. In a preferred embodiment of the present invention, the incubation products are detected by ELISA, RIA, fluoro immunoassay (FIA) or soluble particle immune assay (SPIA).

In some embodiments, binding of two biomolecules can be assayed using thermodenaturation methods involving differential scanning fluorimetry (DSF) and differential static light scattering (DSLS).

In some embodiments, binding of two biomolecules can be assayed using a mass spectrometry based method such as, but not limited to, an affinity selection coupled to mass spectrometry (AS-MS) platform. This is a label-free method where the protein and test compound are incubated, unbound molecules are washed away and protein-ligand complexes are analyzed by MS for ligand identification following a decomplexation step.

In some embodiments, binding of two biomolecules can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled biomolecule, by immunoassay, or by chromatographic detection.

In some embodiments, the present invention contemplates the use of fluorescence polarization assays and fluorescence resonance energy transfer (FRET) assays in measuring, either directly or indirectly, the degree of interaction between two biomolecules.

II. Particles

As used herein, the term "particle" refers to a small mass that can comprise any material, such as alumina, metal (e.g., gold or platinum), glass, silica, latex, plastic, agarose, polyacrylamide, methacrylate or any polymeric material, and be of any size and shape. In some embodiments, the particle or particles comprise silicon. (See, e.g., International Patent Application Publication Nos. WO 2013/011764, WO 2013/029278, and WO 2014/151381, and U.S. Patent Application Publication No. 2014/0271886, the disclosures of each of which are incorporated by reference in their entirety). In some embodiments, the particles comprise or consist of starch (see, e.g., International Patent Application Publication No. WO 2010/084088). In some embodiments, the particle or particles are composed of nucleic acid (e.g., naturally-occurring or non-naturally occurring nucleic acid). Methods for making such nucleic acid-based microscopic structures are described in, e.g., Douglas et al., *Nucl Acids Res* 37(15):5001-5006 (2009); Douglas et al., *Nature* 459(7245):414-428 (2009); Voigt et al., *Nat Nanotechnol* 5(3):200-203 (2010); and Endo et al., *Curr Protoc Nucleic Acid Chem* Chapter 12(Unit 12.8) (2011).

In preferred embodiments, the particle is insoluble in aqueous solution (e.g., the particle may be insoluble in water, blood serum, blood plasma, extracellular fluid, and/or interstitial fluid). For example, a particle may be separated from aqueous solution by centrifuging a solution comprising the particle, e.g., at speeds that are sufficient to separate the cells of a cell suspension from the aqueous solution of the cell suspension. Nevertheless, a particle may readily exist as a suspension in aqueous solution, e.g., mild shaking or vortexing of a plurality of particles in aqueous solution is sufficient to suspend the particles in the solution. In some embodiments, the particle is not a hydrogel. In some embodiments, the particle does not comprise a hydrogel. In some embodiments, the particle does not comprise a polymer.

A particle is preferably large enough to bind to more than one biomolecule and inhibit the interaction of more than one bound biomolecule with a binding partner. For example, a particle may be about 50 nm to about 10 Å particle may be 1 µm to 5 µm in size, 1.2 µm to 4 µm, 1.5 µm to 4 µm, or 2 µm to 4 µm.

Particles with sizes less than 300 nm, such as less than 200 nm or less than 150 nm, are preferred for applications in which the particles are intended to enter and/or exit the vasculature of a subject, such as particles that may be administered by subcutaneous injection. Nevertheless, larger particles are similarly well-suited for subcutaneous injection for methods in which the particles are not intended to enter the vasculature. Particles with sizes of about 1 µm to about 5 µm are preferable for applications in which the particles are intended to circulate within the vasculature of a subject, e.g., following intravenous administration. Particles with sizes greater than 5 µm may be preferable for applications in which the particles are intended to reside at the site in which they are implanted, such as within or adjacent to a tumor; however, particles smaller than 5 µm may also be suitable for implantation. Particles of any size may be utilized for in vitro applications.

Also featured herein are collections of particles. In some embodiments, the plurality of particles has a narrow or broad polydispersity. As used herein, "polydispersity" refers to the range of sizes of particles within a particular particle population. That is, an extremely polydisperse population might involve particles having a mean size of, say, 1 µm with individual particles ranging from 0.1 to 4 µm. In some embodiments, a "narrow polydispersity" is preferred. That is, given a particular mean particle size, it is presently preferred that individual particles in the population differ by no more than ±20%, preferably no more than ±15%, and most preferably at present no more than ±10% from the mean particle size. More specifically, a particle population preferably has a mean particle size of about 0.5 to about 2 more preferably at present from about 0.8 to about 1.5 µm. Thus, if a mean particle size of 1 µm is selected, individual particles in the population would most preferably be within the range of from about 0.8 to about 1.2 µm. In some embodiments, the particle population has a mean particle size of about 0.3 to about 1 µm, e.g., about 0.4 to about 0.9, about 0.5 to about 0.9, about 0.4 to about 0.8, about 0.5 to about 0.7, about 0.3 to about 0.9, or about 0.3 to about 0.7 µm. In some embodiments, the particle population has a mean particle size of about 1 µm to about 10 µm, e.g., about 1.1 µm to about 4.8, about 1.2 µm to about 4.6, about 1.4 µm to about 4.4, about 1.6 µm to about 4.2, about 1.8 µm to about 4.0, or about 2.0 µm to about 3.8 µm.

In some embodiments, the disclosure features a collection or plurality of particles having a defined mean particle size. As used herein, "mean particle size" is arrived at by measuring the size of individual particles and then dividing by the total number of particles. The determination of mean particle size is well known in the art. Typically, the longest average dimension of the particles is no greater than 4 µm. In some embodiments, the longest average dimension of the particles is no greater than 3.9 (e.g., no greater than 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1) µm. In some embodiments, the longest average dimension of the particles is no greater than 2.5 µm, 2 µm, 1.5 µm, or 1.25 µm. In some embodiments, the longest average dimension of the particles is at least 1 µm, but no greater than 4 µm. In some embodiments, the longest average dimension of the particles is at least 1 µm, but no greater than 2 µm. In some embodiments, the longest average dimension of the particles is at least 1 µm, but no greater than 1.5 µm. In some embodiments, the longest average dimension of the particles is at least 0.5 µm (e.g., at least 0.6, 0.7, 0.8, 0.9, 1, 1.1, 1.2, 1.3, 1.4, or 1.5 µm), but no greater than 4 µm (e.g., no greater than 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, or 1.6 µm).

In some embodiments, the particles are nanoparticles. In some embodiments, the longest average dimension of the particles is no greater than 900 nm (e.g., 850, 800, 750, 700, 650, 600, 550, 500, 450, 400, 450, 400, 350, 300, 250, 200, or 150 nm). In some embodiments, a particle is shaped and sized to circulate in the blood or vasculature (e.g., arteries, veins, and capillaries) of a subject (e.g., a human subject). Exemplary particle designs are set forth in FIGS. 1 to 6.

In some embodiments, the longest dimension of the particle is about 50 nm to about 5 µm, such as about 100 nm to about 4.5 µm, about 200 nm to about 4 µm, about 300 nm to about 3.5 µm, about 300 nm to about µm, or about 400 nm to about 3 µm. In some embodiments, the shortest dimension of the particle is at least about 300 nm, such as about 300 nm to about 4 µm or about 400 nm to about 3 µm.

In some embodiments, a plurality of the particles are polyhedral, e.g., cubic. In some embodiments, a plurality of the particles are spherical. In some embodiments, any of the particles described herein can be porous. Such porous particles comprise an outer surface and inner surfaces of the pores of the particle. The agent can be, e.g., immobilized on the inner surfaces. In some embodiments, a plurality of pores have a cross-sectional dimension of at least 50 nm. In some embodiments, a plurality of pores have a cross-sectional dimension of at least 100 nm. Porous nanoparticles have been described in, e.g., U.S. Patent Application Publication Nos. 20140199352, 20080277346, and 20040105821, the disclosures of each of which are incorporated by reference in their entirety. Spherical particles are described in, e.g., U.S. Pat. Nos. 8,778,830 and 8,586,096, each of which is hereby incorporated by reference.

In some embodiments, spherical particles can further comprise two intersecting ridges extending from the spherical surface of the particle, wherein the longest dimension of each of the structures is no greater than 4 µm (e.g., no greater than 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1 µm), and wherein the ridges are sized and oriented: (i) to inhibit the agent immobilized on the surface of the spherical particle from binding to, or activating, a cell surface receptor protein and/or (ii) when the soluble biomolecule is bound to the agent, to inhibit the interaction of the soluble biomolecule and a second member of a specific binding pair of which the soluble biomolecule is the first member.

In some embodiments, a plurality of particles are toroidal. In such embodiments, the agent can be immobilized on an inner circumferential surface of the particle (e.g., around the hole—see FIG. 2). In some embodiments, the diameter of the particle is no greater than 4 µm (e.g., 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, or 1 µm). In some embodiments, the diameter of the particle is no greater than 900 nm (e.g., 850, 800, 750, 700, 650, 600, 550, 500, 450, 400, 350, 300, 200, or 150 nm).

In some embodiments, the particles described herein are dendritic. Such particles are described in, e.g., Du et al., *Small* 11(4):392-413 (2015); Siegwart, D. J. et al., Proceedings National Academy Sciences USA 108(32):12996 (2011); U.S. Pat. Nos. 5,814,272 and 7,932,311; and U.S. Patent Application Publication No. 20040166166, the disclosures of each of which are hereby incorporated by reference herein. As elaborated on below, in some embodiments the geometry of the dendritic particles is such that the agent immobilized on the inner surface of the particle has a reduced, or substantially reduced, ability to interact with a biomolecule on the surface of a cell and/or the soluble biomolecule bound to the particle by virtue of the agent has a reduced, or substantially reduced, ability to interact with its cognate ligand (the second member of the specific binding pair).

In some embodiments, a plurality of particles are polyhedral, e.g., octahedral or icosahedral (see, e.g., FIG. 3), whether regular or irregular. The particles may comprise at least one protrusion from at least one of their vertices (see, e.g., FIG. 3). The particles may comprise more than one (e.g., 2, 3, 4, 5, 6, 7, or 8 or more) protrusion from their vertices. Such protrusions can be, e.g., sized and/or oriented: (i) to inhibit the agent immobilized on the surface of the spherical particle from binding to, or activating, a cell surface receptor protein and/or (ii) when the soluble biomolecule is bound to the agent, to inhibit the interaction of the soluble biomolecule and a second member of a specific binding pair of which the soluble biomolecule is the first member.

A particle may comprise void space, referred to as a "void" or "voids" herein. A void is the space in a particle that is filled by a fluid (e.g., a liquid, which may comprise a biomolecule, or a gas, such as when a particle is dried) or by empty space (e.g., when a particle is in a vacuum, such as after lyophilization). The void volume of a particle may include, for example, the pore volume of a particle and/or the volume of the interior of a hollow core/shell particle, the lumen of a tube, torus, or ring.

In some embodiments, a particle is configured such that blood plasma may freely enter and/or exit the void space of the particle, e.g., when the particle is located in the vasculature of a subject. In some embodiments, a particle is configured such that blood serum may freely enter and/or exit the void space of the particle, e.g., when the particle is located in the vasculature of a subject. In preferred embodiments, a particle is configured such that blood cells cannot enter the void space of the particle. In some embodiments, a particle is configured such that platelets cannot enter the void space of the particle. Nevertheless, a particle may allow for a platelet to enter its void space, e.g., when the particle is configured for use in vitro or when the particle is configured to bind a virus, bacterium, protist, fungal or yeast cell, or other large target, such as a target sized from about 100 nm to about 2 µm.

In some embodiments, a particle is configured such that extracellular fluid may freely enter and/or exit the void space of the particle. In some embodiments, a particle is configured such that interstitial fluid may freely enter and/or exit the void space of the particle. In some embodiments, a particle is configured such that cerebrospinal fluid may freely enter and/or exit the void space of the particle.

The volume of the void space in a particle is preferentially large enough to accommodate more than one biomolecule, e.g., the total void volume of a particle is preferentially large enough to accommodate each biomolecule that is bound to the particle. Nevertheless, a void may be smaller than the total volume of each bound biomolecule so long as the particle is capable of inhibiting interactions between each bound biomolecule and the second members of the binding pairs that include each biomolecule. For example, a particle may need only sequester a binding site of a biomolecule to inhibit interactions between the biomolecule and a second member of a binding pair, and such a particle may contain a void volume that accommodates the binding site of each biomolecule but that allows for other portions of one or more biomolecules to project outward from the void space.

In some embodiments, a particle may comprise about 5% to about 95% void space. A particle comprising protrusions may comprise little or no void space, e.g., because the protrusions may inhibit interactions between bound biomolecule and a second member of a binding pair. A particle comprising a tube may comprise a large amount of void space, e.g., because a tube may comprise a large internal volume relative to the thickness of the walls of the tube. Nevertheless, the void volume of particles with similar geometries may comprise varying amounts of void volume, e.g., tubes comprising walls of the same thickness may vary substantially in void volume percentage depending on tube diameter.

A particle may comprise 0% to about 40% void space, about 20% to about 60% void space, about 40% to about 80% void space, or about 60% to 100% void space. A particle may comprise 0% to about 20% void space, about 10% to about 30% void space, about 20% to about 40% void space, about 30% to about 50% void space, about 40% to about 60% void space, about 50% to about 70% void space, about 60% to about 80% void space, about 70% to about 90% void space, or about 80% to 100% void space. A particle may comprise 0% to about 10% void space, about 5% to about 15% void space, about 10% to about 20% void space, about 15% to about 25% void space, about 10% to about 20% void space, about 15% to about 25% void space, about 10% to about 20% void space, about 15% to about 25% void space, about 10% to about 20% void space, about 15% to about 25% void space, about 20% to about 30% void space, about 25% to about 35% void space, about 30% to about 40% void space, about 35% to about 45% void space, about 40% to about 50% void space, about 45% to about 55% void space, about 50% to about 60% void space, about 55% to about 65% void space, about 60% to about 70% void space, about 65% to about 75% void space, about 70% to about 80% void space, about 75% to about 85% void space, about 80% to about 90% void space, about 85% to about 95% void space, or about 90% to 100% void space.

The particle may comprise a neutral charge at physiological pH (e.g., ~7.4). The particle may comprise a slightly negative or slightly positive charge at physiological pH. The surface of a particle (e.g., outer surface) may comprise a slightly negative or slightly positive charge at physiological pH. In preferred embodiments, the surface of a particle (e.g., outer surface) comprises a slightly negative or neutral charge at physiological pH. The isoelectric point of the particle may be about 5 to about 9, preferably about 6 to about 8. Particles comprising a nucleic acid may have an isoelectric point of about 4 to about 7. In some embodiments, the isoelectric point of the particle is less than 7.4, i.e., such that the particle has a net negative charge at physiological pH. For example, the isoelectric point of the particle may be about 6.0 to about 7.4, such as about 6.4 to about 7.4. A particle comprising a net negative charge at physiological pH is less likely to interact with eukaryotic cells (e.g., mammalian cells) because eukaryotic cells generally comprise cell membranes with a net negative charge. A particle preferably does not comprise sufficient charge (and/or charge density) to engage in non-specific interactions with other charged molecules.

III. Particles Comprising Pores

In some embodiments, the material used to make the particles (e.g., silicon) may have a porosity of about 40% to about 95%, such as about 60% to about 80%. Porosity, as used herein, is a measure of the void spaces in a material, and is a fraction of the volume of voids over the total volume of the material. In certain embodiments, the carrier material has a porosity of at least about 10%, at least about 20%, at least about 30%, at least about 40%, at least about 50%, at least about 60%, at least about 70%, at least about 80%, or even at least about 90%. In particular embodiments, the porosity is greater than about 40%, such as greater than about 50%, greater than about 60%, or even greater than about 70%.

In certain embodiments, the agent is distributed to a pore depth from the surface of the material of at least about 0.005 μm, at least 0.05 μm, at least about 0.1 μm, at least about 0.2 μm, at least about 0.3 μm, at least about 0.4 μm, at least about 0.5 μm, at least about 0.6 μm, or at least about 0.7 μm. In certain embodiments, the agent is distributed in the pores of the carrier material substantially uniformly.

The agent may be loaded into the particle to a depth which is measured as a ratio to the total width of the particle. In certain embodiments, the agent is distributed to a depth of at least about 10% into the particle, to at least about 20% into the particle, at least about 30% into the particle, at least about 40% into the particle, at least about 50% into the particle, or at least about 60% into the particle.

Methods for immobilizing an agent on a porous particle are known, including methods for both immobilizing an agent to a first surface of a particle and immobilizing a different molecule (e.g., coating) to a second surface of the particle (see, e.g., Cauda, V. et al., J. Am. Chem. Soc. 131(32):11361-11370 (2009) and Guan, B. et al., Langmuir, 27(1):328-334 (2011), each of which is hereby incorporated by reference in its entirety). Further, such methods are generally applicable for the manufacture of any of the particles described herein.

The pore size may be preselected to the dimensional characteristics of the agent and target biomolecule to control the release of the biomolecule. Typically, pore sizes that are too small preclude loading of the agent and/or binding of the biomolecule. For example, the average pore diameter for a material may be selected from larger pores, e.g., 15 nm to 40 nm, for high molecular weight molecules, e.g., 200,000-500,000 amu, and smaller pores, e.g., 2 nm to 10 nm, for molecules of a lower molecular weight, e.g., 10,000-50,0000 amu. For instance, average pore sizes of about 6 nm in diameter may be suitable for molecules of molecular weight around 14,000 to 15,000 amu such as about 14,700 amu. Average pore sizes of about 10 nm in diameter may be selected for molecules of molecular weight around 45,000 to 50,000 amu such as about 48,000 amu. Average pore sizes of about 25-30 nm in diameter may be selected for molecules of molecular weight around 150,000 nm.

The pore size may be preselected to be adapted to the molecular radii of the agent or biomolecule. For instance, average pore sizes of about 25 nm to about 40 nm in diameter may be suitable for molecules with a largest molecular radius from about 6 nm to about 8 nm. Molecular radii may be calculated by any suitable method such as by using the physical dimensions of the molecule based on the X-ray crystallography data or using the hydrodynamic radius which represents the solution state size of the molecule. As the solution state calculation is dependent upon the nature of the solution in which the calculation is made, it may be preferable for some measurements to use the physical dimensions of the molecule based on the X-ray crystallography data. As used herein the largest molecular radius reflects half of the largest dimension of the therapeutic agent.

In certain embodiments, the average pore diameter is selected to limit the aggregation of molecules, e.g., proteins, within a pore. It would be advantageous to prevent biomolecules such as proteins from aggregating in a carrier material as this is believed to impede the controlled release of molecules into a biological system. Therefore, a pore that, due to the relationship between its size and the size of a biomolecule, allows, for example, only one biomolecule to enter the pore at any one time, will be preferable to a pore that allows multiple biomolecules to enter the pore together and aggregate within the pore. In certain embodiments, multiple biomolecules may be loaded into a pore, but due to the depth of the pore, the proteins distributed throughout this depth of the pore will aggregate to a lesser extent.

IV. Particles Comprising at Least One Tube

In some embodiments, the particle comprises at least one tube. In preferred embodiments, the at least one tube comprises one open end or two open ends.

The term "tube" refers to a three-dimensional shape having a length along an axis (e.g., a one-dimensional axis in Cartesian space) and an internal cavity, lumen, void, or reservoir along the length of the shape. In some embodiments, perpendicular cross sections along the axis of the tube have a substantially identical shape and/or size. The term "cross section," as used in relation to a tube, refers to a two-dimensional cross section that is perpendicular to the axis of the tube. A larger structure may comprise a tube. For example, a syringe comprises a tube, but the tube does not comprise the syringe plunger. A particle or other article may comprise more than one tube. For example, a syringe may comprise two tubes corresponding to the syringe needle and the syringe barrel, or to parallel barrels of a double syringe (e.g., used for epoxy compositions).

A tube may have a diameter, which is the average length of the line segments that are perpendicular to the axis of the tube, wherein each line segment is bounded by two points on the outer surface of the tube. A tube may have a width and height, wherein the width of the tube is the longest line segment defined by two points on the outer surface of the tube that is perpendicular to the axis of the tube, and the height of the tube is the line segment defined by two points on the outer surface of the tube that is perpendicular to both the axis of the tube and the line segment defining the width of the tube.

A tube may have an internal diameter, which is the average length of the line segments that are perpendicular to the axis of the tube, wherein each line segment is bounded by two points on the inner surface of the tube. A tube may have an internal width and internal height, wherein the internal width of the tube is the longest line segment defined by two points on the outer surface of the tube that is perpendicular to the axis of the tube, and the internal height of the tube is the line segment defined by two points on the outer surface of the tube that is perpendicular to both the axis of the tube and the line segment defining the width of the tube.

A tube may be substantially cylindrical. The tube may have a substantially circular cross section. The cross section of the tube may be an ellipsoid, such as a circle.

The cross section of the tube may be a polygon, such as a regular polygon. The cross section of the tube may be a triangle, such as an equilateral triangle. The cross section of the tube may be a quadrilateral, such as a regular quadrilateral, a rectangle, or a square. The cross section of the tube may be a pentagon, such as a regular pentagon. The cross section of the tube may be a hexagon, such as a regular hexagon. A tube may be a triangular tube, square tube, pentagonal tube, hexagonal tube, heptagonal tube, or octahedral tube.

The length of a tube may be about 5 nm to about 5 μm, such as about 5 nm to about 4 μm, about 5 nm to about 3 μm, about 5 nm to about 2 μm, or about 5 nm to about 1 μm. The length of a tube may be about 50 nm to about 5 μm, such as about 50 nm to about 4 μm, about 50 nm to about 3 μm, about 50 nm to about 2 μm, or about 50 nm to about 1 μm. The length of a tube may be about 100 nm to about 5 μm, such as about 100 nm to about 4 μm, about 100 nm to about 3 μm, about 100 nm to about 2 μm, or about 100 nm to about 1 μm. The length of a tube may be about 300 nm to about 5 μm, such as about 300 nm to about 4 μm, about 300 nm to about 3 μm, about 300 nm to about 2 μm, or about 300 nm to about 1 μm. The length of a tube may be about 500 nm to about 5 μm, such as about 500 nm to about 4 μm, about 500 nm to about 3 μm, about 500 nm to about 2 μm, or about 500 nm to about 1 μm.

The diameter, width, and/or height of a tube may be about 5 nm to about 5 μm, such as about 5 nm to about 4 μm, about 5 nm to about 3 μm, about 5 nm to about 2 μm, about 5 nm to about 1 μm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The diameter, width, and/or height of a tube may be about 50 nm to about 5 μm, such as about 50 nm to about 4 μm, about 50 nm to about 3 μm, about 50 nm to about 2 μm, about 50 nm to about 1 μm, about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm, or about 50 nm to about 100 nm.

The internal diameter, internal width, and/or internal height of a tube are preferentially large enough to accommodate both the agent and the biomolecule. The internal diameter, internal width, and/or internal height of a tube are preferentially small enough to inhibit a cell from entering the interior of the tube (e.g., a nucleated eukaryotic cell, such as a nucleated human cell or a diploid human cell). The internal diameter, internal width, and/or internal height of a tube may be about 5 nm to about 4 μm, such as about 5 nm to about 3 μm, about 5 nm to about 2 μm, about 5 nm to about 1 μm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The internal diameter, internal width, and/or internal height of a tube may be about 20 nm to about 4 μm, such as about 20 nm to about 3 μm, about 20 nm to about 2 μm, about 20 nm to about 1 μm, about 20 nm to about 900 nm, about 20 nm to about 800 nm, about 20 nm to about 700 nm, about 20 nm to about 600 nm, about 20 nm to about 500 nm, about 20 nm to about 400 nm, about 20 nm to about 300 nm, about 20 nm to about 200 nm, or about 20 nm to about 100 nm. The internal diameter, internal width, and/or internal height of a tube may be about 40 nm to about 4 μm, such as about 40 nm to about 3 μm, about 40 nm to about 2 μm, about 40 nm to about 1 μm, about 40 nm to about 900 nm, about 40 nm to about 800 nm, about 40 nm to about 700 nm, about 40 nm to about 600 nm, about 40 nm to about 500 nm, about 40 nm to about 400 nm, about 40 nm to about 300 nm, about 40 nm to about 200 nm, or about 40 nm to about 100 nm.

In certain preferred embodiments, the particle comprises a plurality of tubes. Each tube of the plurality of tubes may be substantially parallel. In some embodiments, at least two tubes of the plurality of tubes are not parallel. In some embodiments, none of the tubes of the plurality of tubes are parallel. The tubes may be arranged in a configuration other than parallel to distribute the openings to the tubes over different faces of the particle or to allow the particle to tumble in flow (e.g., laminar flow or turbulent flow).

A plurality of tubes may be arranged in a lattice or bundle.

A plurality of tubes may be arranged in a polyhedron, such as a regular polyhedron. The plurality of tubes may be arranged in a tetrahedron, such as a regular tetrahedron. The plurality of tubes may be arranged in a hexahedron, such as a cuboid, rectangular cuboid, or cube. The plurality of tubes may be arranged in an octahedron, such as a regular octahedron. The plurality of tubes may be arranged in a dodecahedron, such as a regular dodecahedron. The plurality of tubes may be arranged in an icosahedron, such as a regular icosahedron. In some embodiments, each edge of the polyhedron is defined by a single tube. In some embodiments, less than each edge of the polyhedron is defined by a single tube (e.g., when each of the tubes are substantially parallel).

A plurality of tubes may be arranged in a pyramid, such as a triangular pyramid, rhombic pyramid, rectangular pyramid, square pyramid, pentagonal pyramid, hexagonal pyramid, heptagonal pyramid, or octagonal pyramid. The plurality of tubes may be arranged in a right pyramid or an oblique pyramid. In some embodiments, each edge of the pyramid is defined by a single tube. In some embodiments, less than each edge of the pyramid is defined by a single tube (e.g., when each of the tubes are substantially parallel).

A plurality of tubes may be arranged in a prism, such as a triangular prism, rectangular prism, square prism, pentagonal prism, hexagonal prism, heptagonal prism, or octagonal prism. The plurality of tubes may be arranged in a right prism, an oblique prism, or a truncated prism. In some embodiments, each edge of the prism is defined by a single tube. In some embodiments, less than each edge of the prism is defined by a single tube (e.g., when each of the tubes are substantially parallel).

A plurality of tubes may be arranged in a configuration that has a length, width, and height, wherein no single dimension is more than 5 times larger than any other dimension. For example, the plurality of tubes may be arranged in a configuration wherein no single dimension is more than 4 times larger than any other dimension or no single dimension is more than 3 times larger than any other dimension. Such configurations are favorable, for example, for intravenous administration of a particle because oblong particles may not flow as well in a patient's bloodstream.

A plurality of tubes may be arranged in a configuration that has a length and diameter, wherein the length of the configuration is not more than 5 times its diameter. For the plurality of tubes may be arranged in a configuration wherein the length of the configuration is not more than 4 times its diameter or the length of the configuration is not more than 3 times its diameter. Such configurations are favorable, for example, for intravenous administration of the particle because oblong particles may not flow as well in a patient's bloodstream.

A particle may comprise 1 to 500 tubes, such as 1 to 100 tubes. A particle may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 330, 31, 32, 33, 34, 35, 36, 37, 38, 39, 40, 41, 42, 43, 44, 45, 46, 47, 48, 49, 50, 51, 52, 53, 54, 55, 56, 57, 58, 59, 50, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 tubes.

A plurality of tubes may comprise 1 to 500 tubes, such as 1 to 100 tubes. A plurality of tubes may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 330, 31, 32, 33, 34, 35, 36, 37, 38, 39, 40, 41, 42, 43, 44, 45, 46, 47, 48, 49, 50, 51, 52, 53, 54, 55, 56, 57, 58, 59, 50, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 tubes.

Each tube of the plurality of tubes may have the same length, or different tubes of the plurality of tubes may have different lengths. The average length of a tube may be about 5 nm to about 5 µm, such as about 5 nm to about 4 µm, about 5 nm to about 3 µm, about 5 nm to about 2 µm, or about 5 nm to about 1 µm. The average length of a tube may be about 50 nm to about 5 µm, such as about 50 nm to about 4 µm, about 50 nm to about 3 µm, about 50 nm to about 2 µm, or about 50 nm to about 1 µm. The average length of a tube may be about 100 nm to about 5 µm, such as about 100 nm to about 4 µm, about 100 nm to about 3 µm, about 100 nm to about 2 µm, or about 100 nm to about 1 µm. The average length of a tube may be about 300 nm to about 5 µm, such as about 300 nm to about 4 µm, about 300 nm to about 3 µm, about 300 nm to about 2 µm, or about 300 nm to about 1 µm. The average length of a tube may be about 500 nm to about 5 µm, such as about 500 nm to about 4 µm, about 500 nm to about 3 µm, about 500 nm to about 2 µm, or about 500 nm to about 1 µm.

Each tube of the plurality of tubes may have the same diameter, width, and/or height, or different tubes of the plurality of tubes may have different diameters, widths, and/or heights. The average diameter, width, and/or height of a tube may be about 5 nm to about 5 µm, such as about 5 nm to about 4 µm, about 5 nm to about 3 µm, about 5 nm to about 2 µm, about 5 nm to about 1 µm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The average diameter, width, and/or height of a tube may be about 50 nm to about 5 µm, such as about 50 nm to about 4 µm, about 50 nm to about 3 µm, about 50 nm to about 2 µm, about 50 nm to about 1 µm, about 50 nm to about 900 nm, about 50 nm to about 800 nm, about 50 nm to about 700 nm, about 50 nm to about 600 nm, about 50 nm to about 500 nm, about 50 nm to about 400 nm, about 50 nm to about 300 nm, about 50 nm to about 200 nm, or about 50 nm to about 100 nm.

Each tube of the plurality of tubes may have the same internal diameter, internal width, and/or internal height, or different tubes of the plurality of tubes may have different internal diameters, widths, and/or heights. The average internal diameter, internal width, and/or internal height of a tube may be about 5 nm to about 4 µm, such as about 5 nm to about 3 µm, about 5 nm to about 2 µm, about 5 nm to about 1 µm, about 5 nm to about 900 nm, about 5 nm to about 800 nm, about 5 nm to about 700 nm, about 5 nm to about 600 nm, about 5 nm to about 500 nm, about 5 nm to about 400 nm, about 5 nm to about 300 nm, about 5 nm to about 200 nm, or about 5 nm to about 100 nm. The average internal diameter, internal width, and/or internal height of a tube may be about 20 nm to about 4 µm, such as about 20 nm to about 3 µm, about 20 nm to about 2 µm, about 20 nm to about 1 µm, about 20 nm to about 900 nm, about 20 nm to about 800 nm, about 20 nm to about 700 nm, about 20 nm to about 600 nm, about 20 nm to about 500 nm, about 20 nm to about 400 nm, about 20 nm to about 300 nm, about 20 nm to about 200 nm, or about 20 nm to about 100 nm. The average internal diameter, internal width, and/or internal height of a tube may be about 40 nm to about 4 µm, such as about 40 nm to about 3 µm, about 40 nm to about 2 µm, about 40 nm to about 1 µm, about 40 nm to about 900 nm, about 40 nm to about 800 nm, about 40 nm to about 700 nm, about 40 nm to about 600 nm, about 40 nm to about 500 nm, about 40 nm to about 400 nm, about 40 nm to about 300 nm, about 40 nm to about 200 nm, or about 40 nm to about 100 nm.

A tube may comprise, for example, a polymer. The polymer may be a naturally-occurring polymer or a synthetic polymer. The polymer may be, for example, a nucleic acid (e.g., DNA) or protein.

V. Particles Comprising a DNA Scaffold

In some embodiments, the particle comprises a DNA scaffold, e.g., the particle may comprise a DNA origami scaffold (see, e.g., U.S. Pat. Nos. 8,554,489 and 7,842,793; U.S. Patent Application Publication Nos. 2013/0224859 and 2010/0216978; and PCT Patent Application Publication No. 2014/170898, each of which is hereby incorporated by reference).

The particle may comprise a DNA scaffold, and the DNA scaffold may comprise at least one tube or a plurality of tubes as described herein. For example, the DNA scaffold may comprise at least one substantially hexagonal tube (see, e.g., U.S. Patent Application Publication No. 2013/0224859, hereby incorporated by reference).

The DNA scaffold may comprise a honeycomb or lattice, such as a hexagonal lattice or a square lattice (see, e.g., U.S. Pat. No. 8,554,489, hereby incorporated by reference). In some embodiments, the particle comprises a DNA scaffold, and the DNA scaffold does not comprise a tube. For example, the DNA scaffold may comprise a three-dimensional shape, such as a polyhedron, and the agent may be immobilized in the interior surface of the shape.

The DNA scaffold may comprise a polyhedron, such as a regular polyhedron. The DNA scaffold may comprise a tetrahedron, such as a regular tetrahedron. The DNA scaffold may comprise a hexahedron, such as a cuboid, rectangular cuboid, or cube. The DNA scaffold may comprise an octahedron, such as a regular octahedron. The DNA scaffold may comprise a dodecahedron, such as a regular dodecahedron. The DNA scaffold may comprise an icosahedron, such as a regular icosahedron.

The DNA scaffold may comprise a pyramid, such as a triangular pyramid, rhombic pyramid, rectangular pyramid, square pyramid, pentagonal pyramid, hexagonal pyramid, heptagonal pyramid, or octagonal pyramid. The DNA scaffold may comprise a right pyramid or an oblique pyramid.

The DNA scaffold may comprise a prism, such as a triangular prism, rectangular prism, square prism, pentagonal prism, hexagonal prism, heptagonal prism, or octagonal prism. The DNA scaffold may comprise a right prism, an oblique prism, or a truncated prism.

The DNA scaffold may comprise a length, width, and height, wherein no single dimension is more than 5 times larger than any other dimension. For example, no single dimension may be more than 4 times larger than any other dimension or no single dimension may be more than 3 times larger than any other dimension. Such configurations are favorable, for example, for intravenous administration of the particle because oblong particles may not flow as well in a patient's bloodstream.

In some embodiments, the agent is immobilized on the DNA scaffold. In some embodiments, the agent is bound to a nucleic acid comprising a nucleotide sequence that is complementary to a nucleotide sequence on the DNA scaffold, i.e., the nucleotide sequence has at least about 95%, 96%, 97%, 98%, 99%, or 100% sequence identity with the reverse complement of the nucleotide sequence of the DNA scaffold. Thus, the agent may be immobilized on a surface of the particle by hybridizing the nucleic acid to the DNA scaffold.

VI. Particles Comprising a Shield

A particle may comprise a core subparticle and a shield, e.g., wherein the shield inhibits biomolecules bound to the core subparticle from interacting with molecules on the surface of a cell. The shield may comprise a plurality of shield components. The core subparticle may comprise silica. For example, the core subparticle may comprise a silica surface. The core subparticle may comprise gold, silicon, or a polymer. For example, the core subparticle may comprise a gold, silicon, or polymer surface.

A particle comprising an inner core subparticle and having a shield comprising a plurality of shield components attached to the core subparticle may comprise a core subparticle comprising a silica surface, such as a solid silica subparticle, a porous silica subparticle, or a silica nanoshell having a non-silica interior. The core subparticle may comprise a non-silica core material, such as silicon or gold, coated with silica. The shield components may be in the form of shield subparticles that are smaller than the core subparticle, such as nanospheres, and may comprise silica or a different material, such as gold or a polymer. The material of the surface of the core subparticle and of the shield components may be selected to be different to allow different coupling chemistry to be used to couple further components or species to the surfaces.

An agent may be provided on the surface of the core subparticle but to a lesser extent, or preferably not at all, on the surface of the shield components. For example, an agent may be attached to the surface of a silica core subparticle by a bond (e.g., an ionic, covalent, or electrostatic interaction) that forms preferentially (or exclusively) with the silica core subparticle and not with the shield subparticles, e.g., having a gold surface instead of a silica surface.

In some embodiments, such a particle may comprise a silica core, such as a substantially spherical silica core, and a shield comprising a plurality of gold nanoparticles on the surface of the silica core, the gold nanoparticles having a cross-sectional dimension smaller than a cross-sectional dimension of the core, such as the diameter of the core. The gold nanoparticles may be substantially spherical. The core subparticle may be solid and non-porous or may have a porous surface. Formation of the silica core and of gold nanoparticles on the core may be achieved, for example, as described in in U.S. Pat. No. 6,344,272, Sadtler and Wei, Chem. Comm. 1604-5 (2002); Meuhlig et al., ACS Nano, 5(8):6586-6592 (2011) (each of which is hereby incorporated by reference herein in its entirety). For example, gold nanoparticles may be adsorbed onto an amine-coated silica core by means of electrostatic attraction, or may be linked to a silica core having thiol groups conjugated to the silica surface that then bond to the gold surface of the gold nanoparticles.

The core subparticle may have a cross-sectional dimension, such as the diameter of a spherical or cylindrical subparticle, of 50 nm to 4 μm, such as 50 nm to 200 nm, 100 nm to 500 nm, 200 nm to 1 μm, or 500 nm to 4 μm.

Particles may be assembled from a range of core subparticle diameters and shield subparticle diameters. The available surface area of the core subparticle for scavenging of a biomolecule may depend on the diameter of the shield subparticles and the effective height above the surface of the core subparticle needed for binding of the target/agent complex to the surface, including the effective extent above the surface between the surface and the capture agent.

The number of agents that may be bound to a core subparticle may be calculated based on the surface area of the subparticle. Analogously, the number of target biomolecules that may be bound to the core subparticle may be calculated in a similar fashion. Such calculations may be confirmed, for example, by in vitro studies of protein binding, and may be used to predict the dose of particles that may be needed to scavenge a selected number of target biomolecules (or, in some embodiments, the effective dose of particles or of a formulation containing them for removing a number or reducing a concentration of target biomolecules from a system such as an in vitro system or from the circulation of a patient in treatment of disease).

A particle may comprise an available surface area for the capture of a target of $0.01\ \mu m^2$ to $50\ \mu m^2$, such as $0.01\ \mu m^2$ to $0.1\ \mu m^2$, $0.05\ \mu m^2$ to $0.5\ \mu m^2$, $0.1\ \mu m^2$ to $1.0\ \mu m^2$, $0.5\ \mu m^2$ to $5\ \mu m^2$, $1.0\ \mu m^2$ to $10\ \mu m^2$, $5\ \mu m^2$ to $25\ \mu m^2$, or $10\ \mu m^2$ to $50\ \mu m^2$. For a selected loading of agent per unit area of a core subparticle surface, a maximum dose of particles may be established as suitable to scavenge a desired quantity of target biomolecules based on the core and shield subparticle diameters.

A cross-sectional dimension, such as the diameter, of the shield subparticle may be a multiple of a cross-sectional dimension, such as the diameter, of the core particle. The multiple may be, for example, 0.01 to 0.5, such as 0.02 to 0.2, such as 0.05 to 0.1.

For effective access of a target biomolecule to an agent, the target must be able to diffuse between the shield components to reach the agent on the surface of the core subparticle. For example, targets of less than 100 kDa (e.g., sTNF-R1/2) have sizes that may readily diffuse between shielding spheres that are 40 nm in diameter or greater. For smaller shielding spheres, the effective pore length between the spheres is short, and thus shielding spheres that are smaller than 40 nm are similarly unlikely to impede diffusion.

VII. Particles Comprising Subparticles

In some embodiments, a particle may comprise a core subparticle and a plurality of protecting subparticles. The particle may comprise a shield and the shield may comprise the plurality of protecting subparticles. The agent may be immobilized on a surface of a core subparticle, e.g., wherein the surface of a core subparticle is an inner surface. The plurality of protecting subparticles may be configured to inhibit an interaction of a biomolecule with a second member of a specific binding pair, e.g., when the biomolecule is bound to the particle. The plurality of protecting subparticles may be configured to inhibit an interaction between a biomolecule and a cell, such as a mammalian cell, e.g., when the biomolecule is bound to the particle.

The protecting subparticles may define an outer surface. In preferred embodiments, the agent is not immobilized on the surface of the protecting subparticles.

A core subparticle is preferably large enough to bind to more than one molecule of an agent. For example, a core subparticle may be about 20 nm to about 4 µm in size, such as about 50 nm to about 2 µm in size. A core subparticle may be about 100 nm to about 1000 nm, about 100 nm to about 800 nm, about 100 nm to about 600 nm, about 100 nm to about 400 nm, about 100 nm to about 200 nm, about 200 nm to about 1000 nm, about 200 nm to about 800 nm, about 200 nm to about 600 nm, about 200 nm to about 400 nm, about 400 nm to about 1000 nm, about 400 nm to about 800 nm, about 400 nm to about 600 nm, about 600 nm to about 1000 nm, or about 600 nm to about 800 nm in size. A core subparticle may be about 100 nm to about 4 µm, 100 nm to about 3 µm, 100 nm to about 2 µm, about 200 nm to about 4 µm, 200 nm to about 3 µm, 200 nm to about 2 µm, about 400 nm to about 4 µm, 400 nm to about 3 µm, 400 nm to about 2 µm, about 600 nm to about 4 µm, 600 nm to about 3 µm, 600 nm to about 2 µm, about 800 nm to about 4 µm, 800 nm to about 3 µm, or 800 nm to about 2 µm in size.

A core subparticle may comprise metal, gold, alumina, glass, silica, silicon, starch, agarose, latex, plastic, polyacrylamide, methacrylate, a polymer, or a nucleic acid. In some embodiments, a core subparticle comprises silicon, such as porous silicon.

A core subparticle may be any shape (e.g., cubic, pyramidal, conic, spherical, cylindrical, disk, tetrahedral, hexahedral, octahedral, dodecahedral, or icosahedral) or a core subparticle may lack a defined shape.

A particle may comprise 1 core subparticle. For example, the core subparticle may be a particle of U.S. Pat. No. 7,368,295 or 8,920,625 (each of which is hereby incorporated by reference in its entirety), which is further bound to a plurality of protecting subparticles.

Figure 4:
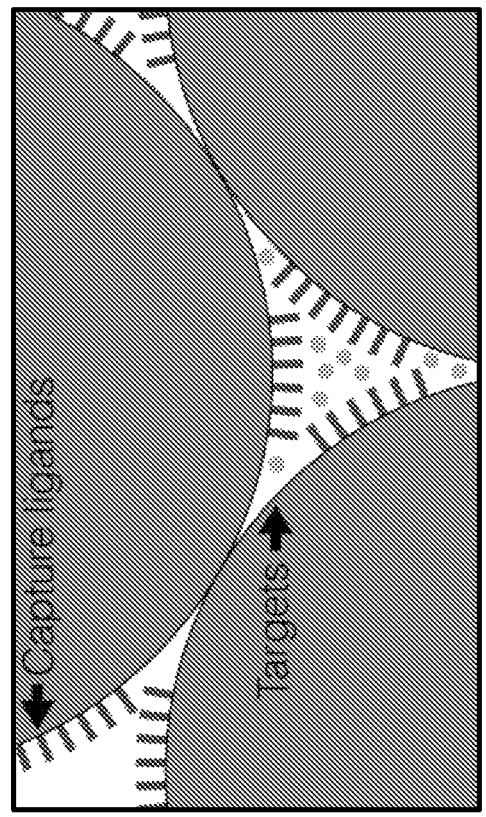
FIG. 4 consists of two panels, labeled panels (A) and (B). Panel (A) depicts the packing of subparticles within a particle comprising core subparticles and protecting subparticles, wherein each subparticle is substantially spherical and approximately the same size. Nevertheless, a particle may comprise subparticles of varying shapes and/or sizes. Additionally, the subparticles are shown as packing in a hexagonal pattern; however, subparticles may pack randomly or with other geometries. Panel (B) depicts (i) "capture ligands" (i.e., agent), which are immobilized on the surface of core subparticles, (ii) targets (e.g., biomolecules) specifically bound to the agent, and (iii) targets within the fluid-filled void space of the particle. Panel (B) does not depict protecting subparticles. The relative sizes of the subparticles, capture ligands, targets, and void space in FIG. 4 are not necessarily shown to scale.
Figure 4:
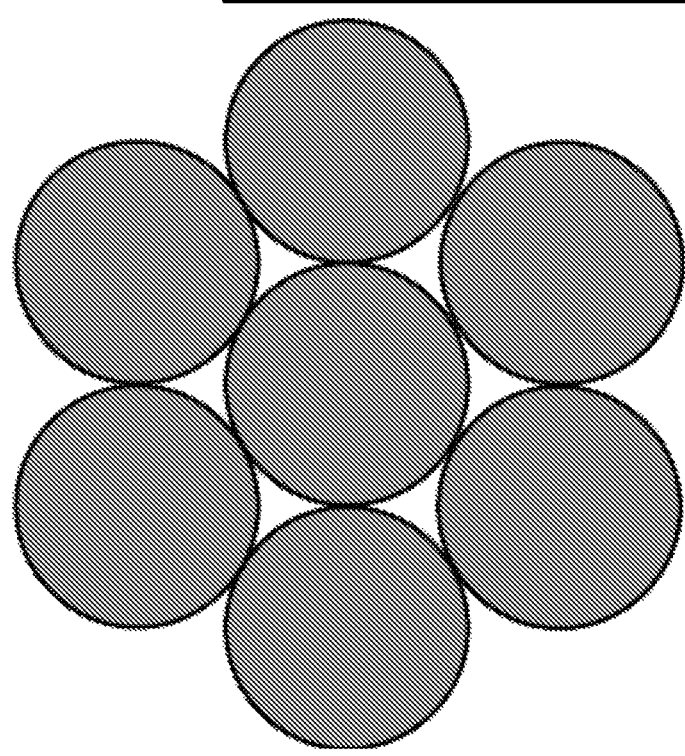
Figure 5:
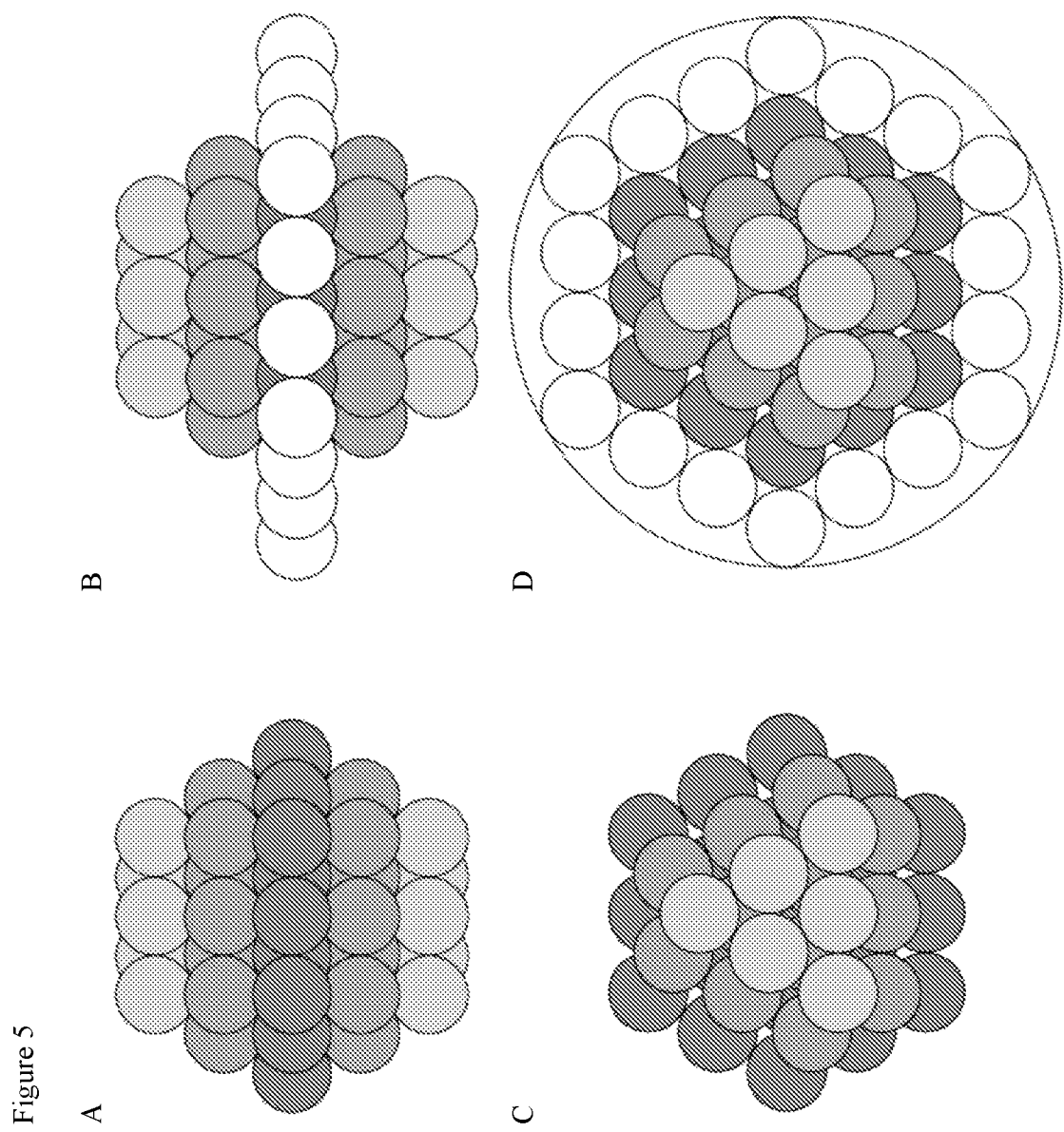
FIG. 5 consists of four panels, labeled panels (A), (B), (C), and (D). Each panel depicts subparticles of a particle, in which core subparticles are shown in gray and protecting subparticles are shown in white. Each particle comprises 55 core subparticles. Panels (A) and (B) depict views of the particle that are orthogonal to the views depicted in panels (C) and (D). Panels (A) and (C) depict the core subparticles only, and panels (B) and (D) depict the core subparticles and a number of protecting subparticles. A completed particle comprising core subparticles and protecting subparticles is preferably covered by at least one layer of protecting subparticles, which is not shown in its entirety in any panel.

A particle may comprise a plurality of core subparticles, such as 2 to 300 core subparticles, 2 to 200 core subparticles, 2 to 150 core subparticles, 2 to 100 core subparticles, 2 to 80 core subparticles, or 2 to 42 core subparticles (see, e.g., FIGS. 4 and 5). In embodiments in which a particle comprises a plurality of core subparticles, each of the core subparticles are preferentially substantially spherical. A particle comprising a plurality of spherical core subparticles allows for voids, thereby allowing the diffusion of soluble biomolecules through the interior of the particle. Nevertheless, core subparticles of various other shapes may allow for voids. A particle comprising a plurality of core subparticles may comprise core subparticles of varying shapes and sizes.

A particle may comprise 1 to about $10^6$ core subparticles, 1 to about $10^5$ core subparticles, 1 to about $10^4$ core subparticles, 1 to about 1000 core subparticles, 1 to about 100 core subparticles, or 1 to about 10 core subparticles. A particle may comprise 2 to about $10^6$ core subparticles, 2 to about $10^5$ core subparticles, 2 to about $10^4$ core subparticles, 2 to about 1000 core subparticles, 2 to about 100 core subparticles, or 2 to about 10 core subparticles. A particle may comprise about 10 to about $10^6$ core subparticles, about 10 to about $10^5$ core subparticles, about 10 to about $10^4$ core subparticles, about 10 to about 1000 core subparticles, or about 10 to about 100 core subparticles.

A core subparticle may comprise pores, i.e., a core subparticle may be porous.

A protecting subparticle may comprise metal, gold, alumina, glass, silica, silicon, starch, agarose, latex, plastic, polyacrylamide, methacrylate, a polymer, or a nucleic acid.

In some embodiments, each protecting subparticle of the plurality of protecting subparticles are tethered to a core subparticle. In some embodiments, some protecting subparticles of the plurality of protecting subparticles are tethered to a core subparticle, and each protecting subparticle of the plurality that is not directly tethered to a core subparticle is tethered to a protecting subparticle, i.e., such that each protecting subparticle of the plurality is either directly or indirectly tethered to a core subparticle. Thus, a particle may comprise a single layer of protecting subparticles (e.g., wherein substantially all of the protecting subparticles are directly tethered to one or more core subparticle(s)) or a particle may comprise more than one layer of protecting subparticles (e.g., wherein a substantial portion of the protecting subparticles are indirectly tethered to one or more core subparticle(s) through direct linkages with other protecting subparticles).

In some embodiments, a particle comprises a first layer of protecting subparticles comprising a first material and a second layer of protecting subparticles comprising a second material. For example, the first material may comprise silica or silicon and the second material may comprise gold. A particle may be assembled, for example, by linking the subparticles of the first layer of subparticles to one or more core subparticles and then linking the subparticles of the second layer of subparticles to the first layer of subparticles. The subparticles of the second layer may comprise a similar surface as the core subparticle(s), e.g., thereby allowing the subparticles of the first layer to link to both the core subparticle(s) and the subparticles of the second layer using similar chemistries.

A particle may be assembled using a layer-by-layer method. For example, a particle may be formed by first linking a plurality of core subparticles. The plurality of core subparticles may be substantially homogenous, e.g., such that a linking molecule may cross-link the core subparticles. The plurality of subparticles may comprise at least two types of subparticles, e.g., with different shapes, sizes, and/or surfaces that allow for a desired feature, such as voids, within the particle. After linking the plurality of core subparticles, a plurality of protecting subparticles may be linked to the plurality of core subparticles. After linking the plurality of protecting subparticles to the core subparticles, a second plurality of protecting subparticles may be linked to the plurality of protecting subparticles. Nevertheless, a particle may be assembled in many different ways, and many different layer-by-layer strategies may be employed depending on the desired properties of the particle and the desired chemistries utilized to link the subparticles.

Methods for crosslinking subparticles are known, including methods for crosslinking subparticles that comprise antibodies for use in vivo (see, e.g., Cheng, K. et al., ACS Appl Mater Interfaces 2(9):2489-2495 (2010), hereby incorporated by reference in its entirety). Such methods may be adapted to produce a particle as described herein, for example, by simply altering the relative sizes of the subparticles.

A protecting subparticle may be about 10 nm to about 4 µm in size, such as about 10 nm to about 1 µm in size, or about 20 nm to about 500 nm in size. A protecting subparticle may be about 10 nm to about 200 nm, 10 nm to about 100 nm, about 10 nm to about 80 nm, about 10 nm to about 60 nm, about 10 nm to about 40 nm, about 10 nm to about 20 nm, 20 nm to about 200 nm, about 20 nm to about 100 nm, about 20 nm to about 80 nm, about 20 nm to about 60 nm, about 20 nm to about 40 nm, 30 nm to about 200 nm, about 40 nm to about 100 nm, about 40 nm to about 80 nm, about 40 nm to about 60 nm, 60 nm to about 200 nm, about 60 nm to about 100 nm, or about 60 nm to about 80 nm in size. A protecting subparticle may be about 100 nm to about 1000 nm, about 100 nm to about 800 nm, about 100 nm to about 600 nm, about 100 nm to about 400 nm, about 100 nm to about 200 nm, about 200 nm to about 1000 nm, about 200 nm to about 800 nm, about 200 nm to about 600 nm, about 200 nm to about 400 nm, about 400 nm to about 1000 nm, about 400 nm to about 800 nm, about 400 nm to about 600 nm, about 600 nm to about 1000 nm, or about 600 nm to about 800 nm in size. A protecting subparticle may be about 100 nm to about 4 about 100 nm to about 3 µm, about 100 nm to about 2 µm, about 200 nm to about 4 about 200 nm to about 3 µm, about 200 nm to about 2 µm, about 400 nm to about 4 about 400 nm to about 3 µm, about 400 nm to about 2 µm, about 600 nm to about 4 about 600 nm to about 3 µm, about 600 nm to about 2 µm, about 800 nm to about 4 about 800 nm to about 3 or about 800 nm to about 2 µm in size.

A particle may comprise 1 to about $10^6$ protecting subparticles, about 4 to about $10^6$ protecting subparticles, about 10 to about $10^6$ protecting subparticles, 1 to about $10^5$ protecting subparticles, about 4 to about $10^5$ protecting subparticles, about 10 to about $10^5$ protecting subparticles, 1 to about $10^4$ protecting subparticles, about 4 to about $10^4$ protecting subparticles, about 10 to about $10^4$ protecting subparticles, 1 to about 1000 protecting subparticles, about 4 to about 1000 protecting subparticles, about 10 to about 1000 protecting subparticles, 1 to about 100 protecting subparticles, about 4 to about 100 protecting subparticles, or about 10 to about 100 protecting subparticles.

A core subparticle and a protecting subparticle may or may not have similar or identical shapes, sizes, and compositions. Nevertheless, a core subparticle varies from a protecting subparticle because (1) agent may be immobilized on a core subparticle whereas agent is preferentially not immobilized on a protecting subparticle, and (2) core subparticles are preferentially located in the interior of a particle whereas protecting subparticles may exist on the outer surface of a particle.

VIII. Substantially 2-Dimensional Particles

Figure 6:
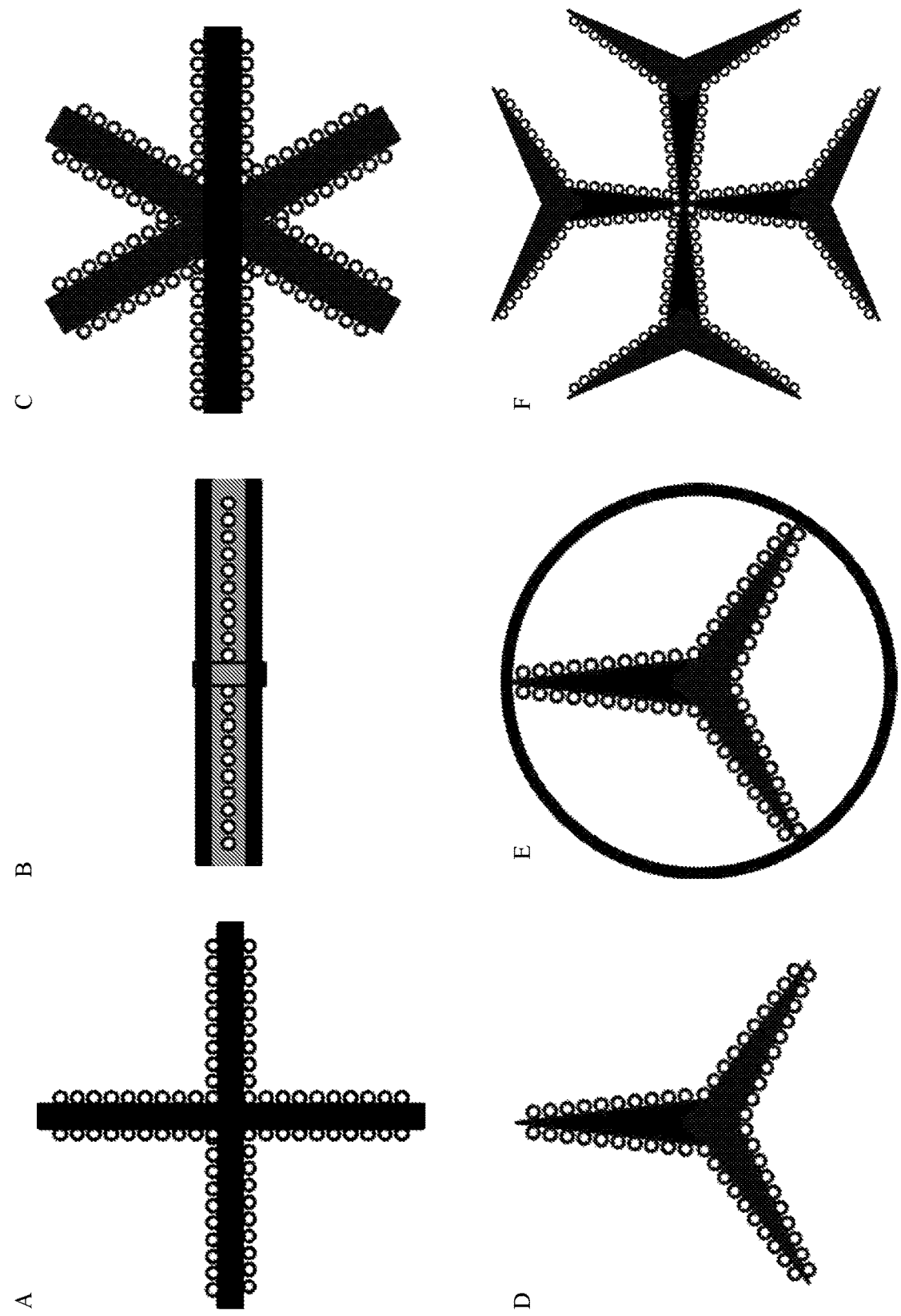
FIG. 6 consists of 6 panels, labeled panels (A), (B), (C), (D), (E), and (F). Each panel depicts a view of a substantially 2-dimensional particle. In each panel, circles depict agent that is immobilized on the surface of the particle. Substantially 2-dimensional particles may comprise "void space," e.g., between the arms of a cross or star. Panel (A) depicts a "top-view" of a particle comprising a cross shape, and panel (B) depicts an orthogonal, "side-view" of the same, cross-shaped particle. The "cross shape" of panel (A) is the "substantially 2-dimensional shape," and the orthogonal, "side-view" is the third dimension, which does not contain the 2-dimensional shape. The "side-view" shows that a substantially 2-dimensional particle may comprise different surfaces, i.e., an "interior surface," on which the agent is immobilized (black), and an "exterior surface" (i.e., "outer surface"), which is substantially free of agent (gray). The different surfaces may comprise different materials, e.g., the particle may be lamellar, or the different surfaces may be prepared, for example, by masking one surface while the other surface is crosslinked to an agent or a coating molecule. Depending on the size of the particle and the nature of the agent and target, a cross shape will inhibit interactions between a bound target (e.g., biomolecule) and other proteins or cells to varying extents. The geometry of a particle may be adjusted, for example, to further inhibit such interactions. Panel (C) depicts a particle comprising a 6-pointed star geometry, which may inhibit interactions between bound target and other proteins or cells to a greater extent than the cross-shaped particle of panel (A). Panel (D) depicts a 3-pointed star, which may only minimally inhibit interactions between bound target and other proteins or cells. Nevertheless, particles comprising a 3-p particle, and the agent is instead either free in solution or linked to an exposed surface). For example, a reactive group may be configured on a particle such that an agent linked to the reactive group (either directly or indirectly, e.g., through a linker) has about the same association constant $k_a$ for soluble forms of a target biomolecule relative to when the agent is not linked to a reactive group of the particle. The $k_a$ of an agent linked to a particle ($k_{a,\ particle}$) may be about the same as the $k_a$ of the agent either free in solution or linked to an exposed surface ($k_{a,\ free}$) for soluble forms of a target biomolecule (e.g., $k_{a,\ particle} \div k_{a,\ free}$ may be from 0.1 to 10, such as 0.2 to 5, 0.5 to 2, 0.8 to 1.2, or 0.9 to 1.1 for agent and soluble targets). Similarly, a reactive group may be configured on a particle such that an agent linked to the reactive group (either directly or indirectly, e.g., through a linker) has about the same equilibrium constant $K_D$ for soluble forms of a target biomolecule relative to when the agent is not linked to a reactive group of the particle. The $K_D$ of an agent linked to a particle ($K_{D,\ particle}$) may be about the same as the $K_D$ of the agent either free in solution or linked to an exposed surface ($K_{D,\ free}$) for soluble forms of a target biomolecule (e.g., $K_{D,\ particle} \div K_{D}$, free may be from 0.1 to 10, such as 0.2 to 5, 0.5 to 2, 0.8 to 1.2, or 0.9 to 1.1 for agent and soluble targets).

A particle may be a 2-dimensional shape. For example, a particle may be a circle, ring, cross, fishbone, ellipse, triangle, square, pentagon, hexagon, heptagon, octagon, or star. A particle may be a star and the star may be a concave hexagon, concave octagon, concave decagon, or concave dodecagon. The shape may be a regular shape or an irregular shape. Examples of substantially 2-dimensional particles are shown in FIG. 6.

In some embodiments, a particle comprises a first side, a second side, and an edge. The first side and second side may be substantially the same shape. The first side and second side may comprise a length and a width. The edge may define a height, which is the distance between the first side and the second side. The width and length may be at least 4 times larger than the height, such as 4 to 1000 times larger, 6 to 100 times larger, 8 to 75 times larger, or 10 to 50 times larger than the height. The width and/or length may be 0.2 times to about 20 times larger than the height.

An edge may comprise one or more concave or re-entrant portions. The agent may be bound to the concave or re-entrant portions of the edge. A re-entrant portion is one in which the perimeter of the particle comprises two adjacent perimeter portions at an exterior angle between them of greater than 270 degrees, such as either side of the points of a star. In this way, the capture agent may be shielded from contact with the membrane of a cell in contact with the particle.

In some embodiments, the first side and/or second side are substantially planar. In some embodiments, the first side and/or second side comprise a concave or re-entrant portion.

In some embodiments, the particle is in the form of a substantially flat star, e.g., with re-entrant portions between the points. A star may have 3, 4, 5, 6, 7, 8, 9, 10, 11, 12, 13, 14, 15, 16, or more points. The particle may comprise regular sides or irregular sides.

In some embodiments, the particle is in the form of a cross or fishbone shape, e.g., comprising a backbone with arms extending on each side outwards from the backbone to define re-entrant surface portions between the arms. The arms of a cross or fishbone may further comprise lateral projections.

The re-entrant edges between the points of the star or the arms of the cross or fishbone preferably extend a distance from the line joining the points such that a cell membrane cannot deform between the points so as to come into contact with the edges. For example, the number of points and the angle between them may determine the depth of the re-entrant edge portions between the points.

Particles suitable for use in the invention may be formed by nanofabrication, for example by nanoprinting or nanomoulding. For example, particles may be produced by the PRINT ("Particle Replication In Non-wetting Templates") process (see, e.g., International patent application WO2007/024323; Perry, J. L. et al., Acc Chem Res. 44(10):990-998 (2011), each of which is hereby incorporated by reference). Particles may be produced by photolithography using known methods.

In some embodiments, an agent may be immobilized on the edge of a particle and not immobilized, or immobilized to a lesser extent, on the first and second sides of a particle.

In some embodiments a desirable surface area per particle is in the range 0.2 to 25 µm². The areas of the shielded edge portions of particles able to be fabricated by nanomoulding are therefore in a desirable range.

IX. Agent

In some embodiments, the agent immobilized on the surface of a particle is a small molecule, a macrocycle compound, a polypeptide, a peptidomimetic compound, an aptamer, a nucleic acid, or a nucleic acid analog. "Small molecule" as used herein, is meant to refer to an agent, which has a molecular weight of less than about 6 kDa and most preferably less than about 2.5 kDa. Many pharmaceutical companies have extensive libraries of chemical and/or biological mixtures comprising arrays of small molecules, often fungal, bacterial, or algal extracts, which can be screened with any of the assays of the application. This application contemplates using, among other things, small chemical libraries, peptide libraries, or collections of natural products. Tan et al. described a library with over two million synthetic compounds that is compatible with miniaturized cell-based assays (*J Am Chem Soc* 120:8565-8566 (1998)).

Peptidomimetics can be compounds in which at least a portion of a subject polypeptide is modified, and the three dimensional structure of the peptidomimetic remains substantially the same as that of the subject polypeptide. Peptidomimetics may be analogues of a subject polypeptide of the disclosure that are, themselves, polypeptides containing one or more substitutions or other modifications within the subject polypeptide sequence. Alternatively, at least a portion of the subject polypeptide sequence may be replaced with a non-peptide structure, such that the three-dimensional structure of the subject polypeptide is substantially retained. In other words, one, two or three amino acid residues within the subject polypeptide sequence may be replaced by a non-peptide structure. In addition, other peptide portions of the subject polypeptide may, but need not, be replaced with a non-peptide structure. Peptidomimetics (both peptide and non-peptidyl analogues) may have improved properties (e.g, decreased proteolysis, increased retention or increased bioavailability). Peptidomimetics generally have improved oral availability, which makes them especially suited to treatment of humans or animals. It should be noted that peptidomimetics may or may not have similar two-dimensional chemical structures, but share common three-dimensional structural features and geometry. Each peptidomimetic may further have one or more unique additional binding elements.

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see, e.g., Ulrich (2006) *Handb Exp Pharmacol.* 173:305-326).

The agent may be an antibody, or an antigen-binding portion thereof (i.e., an antibody fragment), wherein the antibody, or antigen-binding portion thereof, specifically binds to a target (e.g., a soluble biomolecule). The agent may comprise an antibody, or an antigen-binding portion thereof, wherein the antibody, or antigen-binding portion thereof, specifically binds to a target (e.g., a soluble biomolecule). The term "antibody" refers to whole antibodies including antibodies of different isotypes, such as IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

The term "antibody fragment," "biomolecule-binding fragment," "antigen-binding portion of an antibody" and similar terms refer to a fragment of an antibody that retains the ability to bind to a target antigen. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein (see, e.g., Todorovska et al., *J Immunol Methods* 248(1):47-66 (2001); Hudson and Kortt *J Immunol Methods* 231(1):177-189 (1999); Poljak *Structure* 2(12): 1121-1123 (1994); Rondon and Marasco *Annual Review of Microbiology* 51:257-283 (1997), the disclosures of each of which are incorporated herein by reference in their entirety). Bispecific antibodies (including DVD-Ig antibodies) are also embraced by the term "antibody." Bispecific antibodies are monoclonal, preferably human or humanized, antibodies that have binding specificities for at least two different antigens.

As used in herein, the term "antibody" also includes, e.g., single domain antibodies such as camelized single domain antibodies. See, e.g., Muyldermans et al., *Trends Biochem Sci* 26:230-235 (2001); Nuttall et al., *Curr Pharm Biotech* 1:253-263 (2000); Reichmann et al., *J Immunol Meth* 231: 25-38 (1999); PCT application publication nos. WO 94/04678 and WO 94/25591; and U.S. Pat. Nos. 6,005,079, 6,015,695, and 7,794,981, all of which are incorporated herein by reference in their entireties. In some embodiments, the disclosure provides single domain antibodies comprising two VH domains with modifications such that single domain antibodies are formed.

In some embodiments, the agent is a non-antibody, scaffold protein. These proteins are, generally, obtained through combinatorial chemistry-based adaptation of pre-existing ligand- or antigen-binding proteins. For example, the binding site of human transferrin for human transferrin receptor can be modified using combinatorial chemistry to create a diverse library of transferrin variants, some of which have acquired affinity for different antigens (see Ali et al., *J Biol Chem* 274:24066-24073 (1999)). The portion of human transferrin not involved with binding the receptor remains unchanged and serves as a scaffold, like framework regions of antibodies, to present the variant binding sites. The libraries are then screened, as an antibody library is, against a target antigen of interest to identify those variants having optimal selectivity and affinity for the target antigen. Non-antibody scaffold proteins, while similar in function to antibodies, are touted as having a number of advantages as compared to antibodies, which advantages include, among other things, enhanced solubility and tissue penetration, less costly manufacture, and ease of conjugation to other molecules of interest (see Hey et al., *TRENDS Biotechnol* 23(10):514-522 (2005)).

One of skill in the art would appreciate that the scaffold portion of the non-antibody scaffold protein can include, e.g., all or part of: the Z domain of *S. aureus* protein A, human transferrin, human tenth fibronectin type III domain, kunitz domain of a human trypsin inhibitor, human CTLA-4, an ankyrin repeat protein, a human lipocalin, human crystallin, human ubiquitin, or a trypsin inhibitor from *E. elaterium* (see Hey et al., *TRENDS Biotechnol* 23(10):514-522 (2005)).

In some embodiments, the agent is a natural ligand of a target biomolecule. For example, the agent can be a cytokine. As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epidermal keratinocytes and B-lymphocytes. Lymphokines are generally referred to as being produced by lymphocyte cells. Examples of cytokines include, but are not limited to, Interleukin-1 (IL-1), Interleukin-2 (IL-2), Interleukin-6 (IL-6), Interleukin-8 (IL-8), Tumor Necrosis Factor-alpha (TNFα), and Tumor Necrosis Factor beta (TNFβ).

In some embodiments, the agent is a tumor necrosis factor (TNF) family ligand, e.g., the TNF family ligand is selected from TNFα, TNFβ, Fas ligand, lymphotoxin, lymphotoxin alpha, lymphotoxin beta, 4-1BB Ligand, CD30 Ligand, EDA-A1, LIGHT (TNFSF14), TNF-like ligand 1A (TL1A), TNF-related weak inducer of apoptosis (TWEAK), and TNF-related apoptosis-inducing ligand (TRAIL). The agent may be CD40 Ligand, CD27 Ligand, OX40 Ligand, B-cell activating factor (BAFF; TNFSF13B; BLYS), ectodysplasin A (EDA), activation-inducible TNFR family receptor ligand (AITRL), vascular endothelial growth inhibitor (VEGI), a proliferation-inducing ligand (APRIL), or receptor activator of nuclear factor kappa-B ligand (RANKL). In some embodiments, the target is TNFα, TNFβ, Fas ligand, lymphotoxin, lymphotoxin alpha, lymphotoxin beta, 4-1BB Ligand, CD30 Ligand, EDA-A1, LIGHT, TL1A, TWEAK, TRAIL, CD40 Ligand, CD27 Ligand, OX40 Ligand, B-cell activating factor (BAFF; TNFSF13B; BLYS), ectodysplasin A (EDA), activation-inducible TNFR family receptor ligand (AITRL), vascular endothelial growth inhibitor (VEGI), a proliferation-inducing ligand (APRIL), or receptor activator of nuclear factor kappa-B ligand (RANKL).

In some embodiments, the agent is a viral protein, or a portion thereof, which specifically binds to a target (e.g., a soluble form of a membrane protein). In some embodiments, the agent is vTNF, which is a protein capable of specifically-binding TNF that is not encoded by the genome of an organism comprising TNF and TNF receptors. vTNF includes TNF-binding proteins from viruses, such as poxvirus (e.g., Yatapoxvirus, such as Yaba-like disease virus, Tanapox virus, and Yaba monkey tumor virus; Cowpox virus; Myxoma virus; and Mousepox virus) and retrovirus (e.g., Simian foamy virus). For example, vTNF may be Crm B, Crm C, Crm D, or Crm E of the Cowpox virus, M-T2 of the Myxoma virus, S-T2 of the Simian foamy virus, vCD30 of the Cowpox virus, or TPV2L of the Tanapox virus. In some embodiments, the agent is the E6 or E7 of the human papilloma virus, which binds TNFR1, or TRAILR2 ortholog, CAR1 of the Avian sarcoma leukosis virus, which binds to TNFRs.

In some embodiments, the agent is a variant of a natural ligand for a target biomolecule, e.g., a variant interleukin polypeptide, such as variant IL-2 or variant TNFα. Variants, in accordance with some embodiments of the invention, can contain one or more amino acid substitutions, deletions, or insertions. The substitutions can be conservative or non-conservative. As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid or a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W); tyrosine (Y); and valine (V). Variants also include fragments of the full-length, wild-type natural ligands as well as fragments comprising one or more amino acid substitutions, insertions, or deletions relative to the wild-type, full-length natural ligand from which the fragment was derived.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, a variant polypeptide comprises at least two (e.g., at least three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type, full-length polypeptide from which it was derived. In some embodiments, a variant polypeptide comprises no more than 150 (e.g., no more than 145, 140, 135, 130, 125, 120, 115, 110, 105, 100, 95, 90, 85, 80, 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, deletions, or insertions, relative to the wild-type, full-length polypeptide from which it was derived.

In some embodiments, a variant polypeptide (e.g., a variant IL-2 or TNFα polypeptide) retains at least 10 (e.g., at least 15, 20, 25, 30, 35, 40, 45, 50, 55, 60, 65, 70, 75, 80, 85, 90, 95, or 100) % of the ability of the wild-type, full-length polypeptide from which it was derived to bind to the target biomolecule (e.g., the member of the specific binding pair of which the wild-type, full-length polypeptide is a member). In some embodiments, the variant polypeptide will have a greater affinity for the target biomolecule than the wild-type, full-length polypeptide from which the variant was derived. For example, in some embodiments, the variant polypeptide has two (three, four, five, 10, 20, 30, 40, 50, 100, 200, 500, or even 1000) times greater affinity for the target biomolecule than does the wild-type, full-length polypeptide from which the variant polypeptide was derived. Methods for detecting or measuring the interaction between two proteins are known in the art and described above.

In some embodiments, the wild-type, full-length natural ligand modulates the activity of a cell surface receptor. Accordingly, variants of the natural ligands can have enhanced or reduced ability to modulate the activity of the receptor, relative to the activity of the wild-type natural ligand. For example, in some embodiments, a variant polypeptide has less than 90 (e.g., 85, 80, 75, 70, 65, 60, 55, 50, 45, 40, 35, 30, 25, 20, 15, 10, or less than 5) % of the ability of the full-length, wild-type polypeptide from which the variant was derived to activate a cell surface receptor protein. In some embodiments, the variant polypeptide does not activate the receptor to which it binds.

Such exemplary variant polypeptides are known in the art. For example, International Patent Application Publication No. WO 2012/085891 describes TNF family ligand variants having reduced ability to trimerize, and thus a reduced ability to activate TNF family receptors (see also U.S. Patent Application Publication No. U.S. 2014/0096274, hereby incorporated by reference). Yet the variant TNF ligands retain the ability to bind to TNF family receptors. Suitable methods for comparing activity between variant and wild-type natural ligands are known in the art.

In some embodiments, the soluble biomolecule is a ligand for a cell surface receptor, e.g., a cytokine or chemokine (e.g., MCP-1/CCL2, CCL5, CCL11, CCL12, or CCL19), such as any of those known in the art or described herein. In some embodiments, the ligand is a tumor necrosis factor (TNF) family ligand or a variant thereof. In some embodiments, the TNF family ligand is TNFα or a variant thereof. In some embodiments, the TNF family ligand is Fas ligand, lymphotoxin, lymphotoxin alpha, lymphotoxin beta, 4-1BB Ligand, CD30 Ligand, EDA-A1, LIGHT, TL1A, TWEAK, TNFβ, TRAIL, or a variant of any of the foregoing. In some embodiments, the ligand is a TGFβ superfamily ligand or variant thereof, e.g., activin A, activin B, anti-mullerian hormone, growth differentiation factor (e.g., GDF1 or GDF11), a bone morphogenic protein (BMP), inhibin (e.g., inhibin alpha, inhibin beta), lefty, persephin, nodal, neurturin, TGFβ1, TGFβ2, TGFβ3, or myostatin. In some embodiments, the ligand is hormone (e.g., a peptide hormone), such as ghrelin.

In some embodiments, the soluble biomolecule is haptoglobin or beta-2 microglobulin.

In some embodiments, the soluble biomolecule is one identified in Table 2.

TABLE 2

Exemplary Soluble Biomolecules and/or Agents

| First Member of Specific Binding Pair (Soluble Biomolecule or Agent) | Gene Abbrev. | Molecule Class | Associated Disease State | Second member of Specific Binding Pair |
|---|---|---|---|---|
| Tumor Necrosis Factor alpha | TNF | Cytokine | AD, obesity, Type II Diabetes (T2D), Alzheimer's | sTNF-R |
| Soluble Interleukin-2 receptor | IL2RA | Decoy | Cancer | IL-2, daclizumab, basiliximab, inolimomab |
| Ghrelin | GHRL | Hormone | Obesity | Ghrelin receptor (GHSR1); anti-ghrelin autoantibodies |
| Soluble Tumor Necrosis Factor receptor-1 | TNFRSF1A | Decoy | Cancer | rTNF |
| Soluble Tumor Necrosis Factor receptor-2 | TNFRSF1B | Decoy | Cancer | rTNF |
| Transforming Growth Factor beta1 | LTBP1 | Growth Factor | Muscle Degeneration, dis-Differentiation | |
| C-C motif ligand 11, aka: eosinophil chemotactic protein, eotaxin-1 | CCL11 | Cytokine | Decreased Neurogenesis and Cognition | |
| Interleukin-2 | IL2 | Cytokine | AD | sIL-2R, briakinumab |
| Interleukin-6 | IL6 | Cytokine | AD | sIL-6R, olokizumab, sarilumab, siltuximab |
| Interleukin-8 | CXCL8 | Cytokine | AD | IL-8R |
| Interleukin-1A | IL1A | Cytokine | AD | sIL-1RA |
| Interleukin-1B | IL1B | Cytokine | Inflammation, diabetes | canakinumab, gevokizumab |
| C-X-C motif chemokine 10 | CXCL10 | Chemokine | Immune activation | CXCR3, eldelumab |
| Growth Differentiation Factor 8, aka: Myostatin | MSTN | Growth Factor | Sarcopenia | Activin receptor (ActRIIB) |
| Decoy receptor-3 | FAS | Decoy | Cancer | FAS-L |
| Soluble death receptor-4 | TNFRSF10A | Decoy | Cancer | TRAIL-R1 |
| Soluble death receptor-5 | TNFRSF10B | Decoy | Cancer | TRAIL-R2, drozitumab |
| Fas ligand | FASLG | Cytokine | AD | sDcR3 |
| TNF-related apoptosis inducing ligand | TNFSF10 | Cytokine | AD, T2D | sDR4/5 |
| Chemokine (C-X-C Motif) Ligand 1 (Melanoma Growth Stimulating Activity, Alpha) | CXCL1 | Chemokine | Senescence/Cancer | |
| Amyloid beta | APP | Fragment | Alzheimer's | anti-amyloid beta antibodies, e.g., aducanumab |
| β2 microglobulin | B2M | Protein | Aging | |
| TNF-related weak inducer of apoptosis | TNFSF12 | Cytokine | TBD | sDR3 |
| Matrix Metallopeptidase 1 (Interstitial Collagenase) | MMP1 | Protease | Senescence/Cancer | |

TABLE 2-continued

Exemplary Soluble Biomolecules and/or Agents

| First Member of Specific Binding Pair (Soluble Biomolecule or Agent) | Gene Abbrev. | Molecule Class | Associated Disease State | Second member of Specific Binding Pair |
|---|---|---|---|---|
| Matrix Metallopeptidase 2 (Gelatinase A, 72 kDa Gelatinase, 72 kDa Type IV Collagenase) | MMP2 | Protease | OA/Cancer | |
| Matrix Metallopeptidase 3 (Stromelysin 1, Progelatinase) | MMP3 | Protease | Senescence/ Cancer | |
| Matrix Metallopeptidase 9 (Gelatinase B, 92 kDa Gelatinase, 92 kDa Type IV Collagenase) | MMP9 | Protease | OA/Cancer | |
| Matrix Metallopeptidase 10 (Stromelysin 2) | MMP10 | Protease | Senescence/ Cancer | |
| Matrix Metallopeptidase 12 (Macrophage Elastase) | MMP12 | Protease | Senescence/ Cancer | |
| Indoleamine 2,3-dioxygenase | IDO1 | Enzyme | Cancer | |
| Neurogenic locus notch homolog protein 1 | NOTCH1 | Cytokine | Stem cell dysfunction | |
| Neurogenic locus notch homolog protein 2 | NOTCH2 | Cytokine | Stem cell dysfunction | |
| Neurogenic locus notch homolog protein 3 | NOTCH3 | Cytokine | Stem cell dysfunction | |
| Neurogenic locus notch homolog protein 4 | NOTCH4 | Cytokine | Stem cell dysfunction | |
| Interleukin-5 | IL5 | Cytokine | AD | Mepolizumab, reslizumab |
| Soluble Interleukin-5 receptor | IL5RA | Decoy | Cancer | IL-5 |
| Soluble interleukin-6 receptor | IL6R | Decoy | Cancer | IL-6, tocilizumab |
| Soluble interleukin-8 receptor | CXCR1 | Decoy | Cancer | IL-8 |
| Soluble interleukin-1A receptor | IL1R1 | Decoy | Cancer | IL-1A |
| C-Reactive Protein | CRP | Protein | Marker of inflammation | |
| Haptoglobin | HP | Protein | | |
| Fibrinogen Alpha Chain | FGA | Protein | Heart disease | |
| Soluble death receptor-3 | TNFRSF25 | Decoy | | TWEAK |
| CD47 | CD47 | Protein | Cancer | thrombospondin-1; signal-regulatory protein alpha (SIRPα) |

"AD" refers to autoimmune disorders and/or inflammatory disorders.
"OA" refers to osteoarthritis.

In some embodiments, an agent may bind (e.g., specifically bind) to a biomolecule selected from TNFα, TNFβ, a soluble TNF receptor, soluble TNFR-1, soluble TNFR-2, lymphotoxin, lymphotoxin alpha, lymphotoxin beta, 4-1BB Ligand, CD30 Ligand, EDA-A1, LIGHT, TL1A, TWEAK, TRAIL, soluble TRAIL receptor, IL-1, soluble IL-1 receptor, IL-1A, soluble IL-1A receptor, IL-1B, soluble IL-1B receptor, IL-2, soluble IL-2 receptor, IL-5, soluble IL-5 receptor, IL-6, soluble IL-6 receptor, IL-8, IL-10, soluble IL-10 receptor, CXCL1, CXCL8, CXCL9, CXCL10, CX3CL1, FAS ligand, soluble death receptor-3, soluble death receptor-4, soluble death receptor-5, TNF-related weak inducer of apoptosis, MMP1, MMP2, MMP3, MMP9, MMP10, MMP12, CD28, a soluble member of the B7 family, soluble CD80/B7-1, soluble CD86/B7-2, soluble CTLA4, soluble PD-L1, soluble PD-1, soluble Tim3, Tim3L, galectin 3, galectin 9, soluble CEACAM1, soluble LAG3, TGF-β, TGF-β1, TGF-β2, TGF-β3, anti-mullerian hormone, artemin, glial cell-derivedneurotrophic factor (GDNF), a bone morphogenic protein (e.g., BMP2, BMP3, BMP3B, BMP4, BMP5, BMP6, BMP7, BMP8A, BMP8B, BMP10, BMP 11, BMP 12, BMP13, BMP15), a growth differentiation factor (e.g., GDF1, GDF2, GDF3, GDF3A, GDF5, GDF6, GDF7, GDF8, GDF9, GDF10, GDF11, GDF15), inhibin alpha, inhibin beta (e.g., inhibin beta A, B, C, E), lefty, nodal, neurturin, persephin, myostatin, ghrelin, sLR11, CCL2, CCL5, CCL11, CCL12, CCL19, interferon alpha, interferon beta, interferon gamma, clusterin, VEGF-A, granulocyte colony-stimulating factor (G-CSF), granulocyte-macrophage colony-stimulating factor (GM-CSF), prostaglandin E2, hepatocyte growth factor, nerve growth factor, sclerostin, complement C5, angiopoietin 2, angiopoietin 3, PCSK9, amyloid beta, activin, activin A, activin B, β2 microglobulin, soluble NOTCH1, soluble NOTCH2, soluble NOTCH3, soluble NOTCH4, soluble Jagged1, soluble Jagged2, soluble DLL1, soluble DLL3, soluble DLL4, haptoglobin, fibrinogen alpha chain, corticotropin releasing factor, corticotropin releasing factor type 1, corticotropin releasing factor type 2, urocortin 1, urocortin 2, urocortin 3, CD47, an anti-interferon γ autoantibody, an anti-interleukin 6 autoantibody, an anti-interleukin 17 autoantibody, an anti-ghrelin autoantibody, wnt, indoleamine 2,3-dioxygenase, C-reactive protein, HIV-1 gp120, endotoxin, ricin toxin, epsilon toxin of *Clostridium perfringens, Staphylococcus* enterotoxin B, and botulinum toxin.

In some embodiments, the agent may comprise an antibody (or an antigen-binding portion thereof) that specifically binds to TNFα, TNFβ, a soluble TNF receptor, soluble TNFR-1, soluble TNFR-2, lymphotoxin, lymphotoxin alpha, lymphotoxin beta, 4-1BB Ligand, CD30 Ligand, EDA-A1, LIGHT, TL1A, TWEAK, TRAIL, soluble TRAIL receptor, IL-1, soluble IL-1 receptor, IL-1A, soluble IL-1A receptor, IL-1B, soluble IL-1B receptor, IL-2, soluble IL-2 receptor, IL-5, soluble IL-5 receptor, IL-6, soluble IL-6 receptor, IL-8, IL-10, soluble IL-10 receptor, CXCL1, CXCL8, CXCL9, CXCL10, CX3CL1, FAS ligand, soluble death receptor-3, soluble death receptor-4, soluble death receptor-5, TNF-related weak inducer of apoptosis, MMP1, MMP2, MMP3, MMP9, MMP10, MMP12, CD28, a soluble member of the B7 family, soluble CD80/B7-1, soluble CD86/B7-2, soluble CTLA4, soluble PD-L1, soluble PD-1, soluble Tim3, Tim3L, galectin 3, galectin 9, soluble CEACAM1, soluble LAG3, TGF-β, TGF-β1, TGF-β2, TGF-β3, anti-mullerian hormone, artemin, glial cell-derived neurotrophic factor (GDNF), a bone morphogenic protein (e.g., BMP2, BMP3, BMP3B, BMP4, BMP5, BMP6, BMP7, BMP8A, BMP8B, BMP10, BMP 11, BMP 12, BMP13, BMP15), a growth differentiation factor (e.g., GDF1, GDF2, GDF3, GDF3A, GDF5, GDF6, GDF7, GDF8, GDF9, GDF10, GDF11, GDF15), inhibin alpha, inhibin beta (e.g., inhibin beta A, B, C, E), lefty, nodal, neurturin, persephin, myostatin, ghrelin, sLR11, CCL2, CCL5, CCL11, CCL12, CCL19, interferon alpha, interferon beta, interferon gamma, clusterin, VEGF-A, granulocyte colony-stimulating factor (G-CSF), granulocyte-macrophage colony-stimulating factor (GM-CSF), prostaglandin E2, hepatocyte growth factor, nerve growth factor, sclerostin, complement C5, angiopoietin 2, angiopoietin 3, PCSK9, amyloid beta, activin, activin A, activin B, β2 microglobulin, soluble NOTCH1, soluble NOTCH2, soluble NOTCH3, soluble NOTCH4, soluble Jagged1, soluble Jagged2, soluble DLL1, soluble DLL3, soluble DLL4, haptoglobin, fibrinogen alpha chain, corticotropin releasing factor, corticotropin releasing factor type 1, corticotropin releasing factor type 2, urocortin 1, urocortin 2, urocortin 3, CD47, an anti-interferon γ autoantibody, an anti-interleukin 6 autoantibody, an anti-interleukin 17 autoantibody, an anti-ghrelin autoantibody, wnt, indoleamine 2,3-dioxygenase, C-reactive protein, HIV-1 gp120, endotoxin, ricin toxin, epsilon toxin of *Clostridium perfringens*, *Staphylococcus* enterotoxin B, or botulinum toxin.

The agent may comprise ipilimumab, pembrolizumab, nivolumab, infliximab, adalimumab, certolizumab (e.g., certolizumab pegol), golimumab, etanercept, stamulumab, fresolimumab, metelimumab, demcizumab, tarextumab, brontictuzumab, mepolizumab, urelumab, canakinumab, daclizumab, belimumab, denosumab, eculizumab, tocilizumab, atlizumab, ustekinumab, palivizumab, aducanumab, bevacizumab, brolucizumab, ranibizumab, aflibercept, actoxumab, elsilimomab, siltuximab, afelimomab, nerelimomab, ozoralizumab, pateclizumab, sirukumab, omalizumab, aducanumab, bapineuzumab, crenezumab, gantenerumab, ponezumab, solanezumab, dapirolizumab, ruplizumab, toralizumab, enoticumab, alacizumab, cetuximab, futuximab, icrucumab, imgatuzumab, matuzumab, necitumumab, nimotuzumab, panitumumab, ramucirumab, zalutumumab, duligotumab, patritumab, ertumaxomab, pertuzumab, trastuzumab, alirocumab, anrukinzumab, diridavumab, drozitumab, dupilumab, dusigitumab, eculizumab, edobacomab, efungumab, eldelumab, enoblituzumab, enokizumab, evinacumab, evolocumab, exbivirumab, exbivirumab, fasinumab, felvizumab, fezakinumab, ficlatuzumab, firivumab, fletikumab, foralumab, foravirumab, fulranumab, faliximab, ganitumab, gevokizumab, fuselkumab, idarucizumab, imalumab, inolimomab, iratumumab, ixekizumab, lampalizumab, lebrikizumab, lenzilumab, lerdelimumab, lexatumumab, libivirumab, ligelizumab, lodelcizumab, lulizumab, mapatumumab, motavizumab, namilumab, nebacumab, nesvacumab, obiltoxaximab, olokizumab, orticumab, pagibaximab, palivizumab, panobacumab, pascolizumab, perakizumab, pidilizumab, pexelizumab, pritoxaximab, quilizumab, radretumab, rafivirumab, ralpancizumab, raxibacumab, regavirumab, reslizumab, rilotumumab, romosozumab, rontalizumab, sarilumab, secukinumab, setoxaximab, sevirumab, sifalimumab, siltuximab, suvizumab, tabalumab, tacatuzumab, talizumab, tanezumab, tefibazumab, TGN1412, tildrakizumab, tigatuzumab, TNX-650, tosatoxumab, tralokinumab, tremelimumab, trevogrumab, tuvirumab, urtoxazumab, vantictumab, vanucizumab, or an antigen binding portion of any one of the foregoing.

In some embodiments, the agent comprises TNFα, TNFβ, a soluble TNF receptor, soluble TNFR-1, soluble TNFR-2, vTNF, lymphotoxin, lymphotoxin alpha, lymphotoxin beta, 4-1BB Ligand, CD30 Ligand, EDA-A1, LIGHT, TL1A, TWEAK, TRAIL, soluble TRAIL receptor, IL-1, soluble IL-1 receptor, IL-1A, soluble IL-1A receptor, IL-1B, soluble IL-1B receptor, IL-2, soluble IL-2 receptor, IL-5, soluble IL-5 receptor, IL-6, soluble IL-6 receptor, IL-8, IL-10, soluble IL-10 receptor, CXCL1, CXCL8, CXCL9, CXCL10, CX3CL1, FAS ligand, soluble death receptor-3, soluble death receptor-4, soluble death receptor-5, TNF-related weak inducer of apoptosis, MMP1, MMP2, MMP3, MMP9, MMP10, MMP12, CD28, a soluble member of the B7 family, soluble CD80/B7-1, soluble CD86/B7-2, soluble CTLA4, soluble PD-L1, soluble PD-1, soluble Tim3, Tim3L, galectin 3, galectin 9, soluble CEACAM1, soluble LAG3, TGF-β, TGF-β1, TGF-β2, TGF-β3, sLR11, CCL2, CCL5, CCL11, CCL12, CCL19, activin, activin A, activin B, soluble NOTCH1, soluble NOTCH2, soluble NOTCH3, soluble NOTCH4, soluble Jagged1, soluble Jagged2, soluble DLL1, soluble DLL3, soluble DLL4, or haptoglobin.

In some embodiments, each particle comprises a plurality of agents. The plurality of agents may comprise 10 to about $10^9$ copies of the agent, such as about $10^3$ to about $10^7$ copies of the agent or about $10^4$ to about $10^6$ copies of the agent.

X. Methods for Producing an Antibody

As noted above, in some embodiments the agents immobilized on the surface of the particle or particles is an antibody or antigen-binding fragment thereof. Antibodies may be elicited by methods known in the art. For example, a mammal, such as a mouse, a hamster or rabbit, may be immunized with an immunogenic form of a biomolecule (e.g., a soluble TNFR, a toxin, or a viral protein). Alternatively, immunization may occur by using a nucleic acid, which in vivo expresses a biomolecule (e.g., a soluble protein) giving rise to the immunogenic response observed. Techniques for conferring immunogenicity on a protein or peptide include conjugation to carriers or other techniques well known in the art. For instance, a peptidyl portion of a polypeptide of the invention may be administered in the presence of adjuvant. The progress of immunization may be monitored by the detection of antibody titers in plasma or serum. Standard ELISA or other immunoassays may be used with the immunogen as antigen to assess the concentrations of antibodies.

Following immunization, antisera reactive with a polypeptide of the invention may be obtained and, if desired, polyclonal antibodies isolated from the serum. To produce monoclonal antibodies, antibody producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256:

495-497), as the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with the polypeptides of the invention and the monoclonal antibodies isolated.

XI. Immobilizing an Agent on a Particle

An agent may be immobilized on a surface of a particle by a covalent bond or a non-covalent bond, such as by ionic bond, hydrogen bond, hydrophobic bond, coordination, adhesive, or physical absorption or interaction A particle may comprise a reactive group, e.g., for immobilizing an agent. The particle may comprise about 10 to about $10^9$ reactive groups, such as about $10^2$ to about $10^8$ reactive groups, about $10^3$ to about $10^7$ reactive groups, or about $10^4$ to about $10^6$ reactive groups. A particle may comprise a plurality of reactive groups. For example, the plurality of reactive groups may comprise about 10 to about $10^9$ reactive groups, such as about $10^2$ to about $10^8$ reactive groups, about $10^3$ to about $10^7$ reactive groups, or about $10^4$ to about $10^6$ reactive groups.

Methods for adding reactive groups to various different types of particles are known (see, e.g., Xu, Z. et al. J Nanoparticle Research 17:56 (2015); Yu, M. K. et al. Theranostics 2(1):3 (2012); Sanz, V. et al. J Nanoparticle Research 14:917 (2012); Jokerst, J. V. et al. Nanomedicine 6(4):715 (2011); Guan, B. et al. Langmuir 27(1):328 (2011); Cheng, K. et al. ACS Applied Materials & Interfaces 2(9):2489 (2010); Godin, B. et al. J Biomed Mater Res A 94(4):1236 (2010); Cauda, V. et al. J. Am. Chem. Sco. 131(32):11361 (2009); Kecht, J. et al. Chemistry of Materials 20(23):7207 (2008); Boisselier, E. et al. Chemical Communications 30(44):5788 (2008); Sun, X.-L. et al. Bioconjugate Chemistry 17(1):52 (2006), each of which is hereby incorporated by reference in its entirety).

Each reactive group may selectively react with a predetermined functional group. In some embodiments, a reactive group can form a bond with an agent, as described herein, which may comprise (e.g., by coupling via a linker) a functional group capable of reacting, preferably selectively reacting, with the reactive groups (FIG. 7). In some embodiments, an agent, as described herein, can form a bond with a reactive group. In some embodiments, each reactive group of the plurality of reactive groups can form a bond with an agent, as described herein. In some embodiments, each agent of a plurality of agents can form a bond with a reactive group. The bond may be a covalent bond or a non-covalent bond. Examples of non-covalent bonds include the base pairing of complementary nucleotides in a nucleotide sequence (e.g., when the reactive group comprises a nucleic acid) inclusion complexes (e.g., between a cyclodextrin ring and a non-polar moiety), and biotin complexes (e.g., with avidin, streptavidin, neutravidin, and monomeric forms of the foregoing). A particle may comprise a plurality of agents (which may be the same or different) coupled to the particle through the reactive groups, e.g., wherein each agent is linked, directly or indirectly, to a reactive group.

In some aspects, the invention relates to a method of making a particle as described herein, comprising incubating an unloaded particle (e.g., a particle comprising one or more reactive groups) with an agent of the invention (e.g., coupled, if necessary, to a functional group capable of reacting with the reactive groups), thereby forming a bond between the particle (e.g., a reactive group of the particle) and the agent. In some embodiments, the method comprises incubating an unloaded particle (e.g., a particle comprising a plurality of reactive groups) with a plurality of agents, which may be the same or different, thereby forming bonds between the particle (e.g., a population of reactive groups of the particle) and a population of agents.

A particle may comprise a linker, e.g., for linking an agent to a reactive group. The particle may comprise about 10 to about $10^9$ linkers, such as about $10^2$ to about $10^8$ linkers, about $10^3$ to about $10^7$ linkers, or about $10^4$ to about $10^6$ linkers. A particle may comprise a plurality of linkers. For example, the plurality of linkers may comprise about 10 to about $10^9$ linkers, such as about $10^2$ to about $10^8$ linkers, about $10^3$ to about $10^7$ linkers, or about $10^4$ to about $10^6$ linkers.

In some embodiments, a reactive group and/or agent of the invention can form a bond with a linker. In some embodiments, a linker can form a bond with a reactive group and/or agent. In some embodiments, each reactive group of the plurality of reactive groups can form a bond with a linker. In some embodiments, each agent of the plurality of agents can form a bond with a linker. In some embodiments, each linker of the plurality of linkers can form a bond with a reactive group. In some embodiments, each linker of the plurality of linkers can form a bond with an agent. The bond may be a covalent bond or a non-covalent bond. In some embodiments, the particle comprises a linker. The linker may be bound to a reactive group. In some embodiments, a particle comprises a plurality of linkers. For example, a particle may comprise a plurality of reactive groups and a plurality of linkers, e.g., wherein each linker of the plurality of linkers is bound to a reactive group of the plurality of reactive groups. A particle may comprise a plurality or reactive groups, a plurality of linkers, and a plurality of agents, e.g., wherein each agent is bound to a linker and/or each linker is bound to a reactive group.

A linker may comprise a functional group. In some embodiments, a reactive group and/or agent of the invention can form a bond with a functional group. In some embodiments, a functional group can form a bond with a reactive group, e.g., to form an amide or ester when a carboxylate and amine or alcohol react, or an amine or thioether when an amine or thiol reacts with a maleimide or other Michael acceptor. In some embodiments, each reactive group of the plurality of reactive groups can form a bond with a functional group. In some embodiments, each functional group of the plurality of functional groups can form a bond with a reactive group. The bond may be a covalent bond or a non-covalent bond. In some embodiments, the particle comprises a functional group. The functional group may be bound to a reactive group, e.g., presenting as an amide, ester, amine, thioether, or other product of the reaction of a functional group and a reactive group. In some embodiments, a particle comprises a plurality of functional groups. For example, a particle may comprise a plurality of reactive groups and a plurality of functional groups, e.g., wherein each functional group of the plurality of functional groups is bound to a reactive group of the plurality of reactive groups, e.g., presenting as an amide, ester, amine, thioether, or other product of the reaction of a functional group and a reactive group. A particle may comprise a plurality of reactive groups, a plurality of functional groups, and a plurality of agents, e.g., wherein each agent is bound to a functional group and/or each functional group is bound to a reactive group. Of course, it is not necessary that each reactive group of the particle be coupled to a functional group/agent, so long as a plurality of these reactive groups are coupled to functional groups/agents to impart the desired functionality to the particle.

A linker may comprise a first functional group and a second functional group. The first functional group may be capable of selectively reacting with an agent bearing a predetermined moiety capable of reacting with the first functional group. The second functional group may be capable of selectively reacting with the reactive groups of the particles. The first functional group and/or the second functional group may be, for example, an alkene, alkyl halide, alkyne, amine, aryl azide, aryl halides, azide, carbodiimide, carboxyl, diene, dienophile, glyoxal, haloacyl, imidoester, isocyanide, maleimide, N-hydroxysuccinimidyl (NHS) ester, phosphine, tetrazine, thiol, or nucleic acid.

A linker may be, for example, succinimidyl 4-(N-maleimidomethyl)cyclohexane-1-carboxylate (SMCC), sulfosuccinimidyl 4-(N-maleimidomethyl)cyclohexane-1-carboxylate (sulfo-SMCC), poly(ethylene glycol) (N-hydroxysuccinimide 5-pentanoate) ether N'-(3-maleimidopropionyl)aminoethane (NHS-PEG-MAL), succinimidyl 3-(2-pyridyldithio)propionate) (SPDP), or succinimidyl iodoacetate (SIA) (see, e.g., Yu, M. K. et al. Theranostics 2(1):3 (2012)).

A linker may comprise a first functional group and a second functional group, wherein either the first functional group is an amine and the second functional group is a carboxylic acid, or the first functional group is a carboxylic acid and the second functional group is an amine. A particle may comprise a plurality of functional groups, wherein the functional groups are primary amine groups.

The particle may be a silica particle, or a particle comprising a silica surface (e.g., a silicon particle having an oxidized surface or a particle having a non-silica core and a silica outer layer). The particle may comprise a gold surface (e.g., the particle may be a gold particle or have a gold surface coating a core comprising a different material). The particle may comprise a polymer surface (e.g., the particle may be a polymer particle or have a polymer surface coating a core comprising a different material). A surface of a coated particle may be a continuous surface (e.g., covering substantially all of a surface of a particle), or a discontinuous surface (e.g., covering a portion or portions of a surface of a particle).

Each reactive group of the particle may be the gold, which may bind, for example, a thiol functional group. A linker or agent may therefore comprise a thiol. In some embodiments, a linker comprises a thiol (e.g., wherein the thiol is a functional group) and a carboxylic acid. A particle may comprise an amine reactive group (e.g., a plurality of amine reactive groups). For example, a particle may be a silica particle or comprise a silica surface, and the particle may comprise a plurality of reactive groups, wherein each reactive group of the plurality of reactive groups is an amine. A particle may be a polymer particle or comprise a polymer surface, and the particle may comprise a plurality of reactive groups, wherein each reactive group of the plurality of reactive groups is an amine.

A reactive group may comprise an aromatic hydrazine (e.g., 6-hydrazino-nicotinic acid) and a functional group may comprise an aromatic aldehyde (e.g., 4-formylbenzoate), or a reactive group may comprise an aromatic aldehyde (e.g., 4-formylbenzoate) and a functional group may comprise an aromatic hydrazine (e.g., 6-hydrazino-nicotinic acid), for example, thereby allowing the reactive group to bind the functional group in the presence of aniline (see, e.g., U.S. 2014/0302001, hereby incorporated by reference in its entirety, and http://www.solulink.com/solulink-technology).

A particle may comprise a plurality of reactive groups, wherein each reactive group comprises a carboxylic acid. A functional group may comprise an amine. A reactive group may be cross-linked to a functional group, for example, using a carbodiimide (e.g., 1-ethyl-3-(3-dimethylaminopropyl)carbodiimide, dicyclohexylcarbodiimide, diisopropylcarbodiimide), optionally using a triazole (e.g., 1-hydroxy-benzotriazole, 1-hydroxy-7-aza-benzotriazole) or an N-hydroxysuccinimidyl ester (e.g., N-hydroxysuccinimide).

A particle may comprise a gold or a gold surface (e.g., overlaying silica). The reactive group or plurality of reactive groups may be gold and the functional group or plurality of functional groups may be thiols (e.g., the functional group of a linker or agent may be a thiol). For example, the agent may comprise a cysteine, e.g., wherein the functional group is a thiol of a cysteine.

A particle may comprise a plurality of reactive groups, wherein each reactive group comprises a maleimide. A functional group may comprise a thiol (e.g., a functional group of a linker or an agent), thereby allowing the functional group to bind a maleimide of the particle. For example, the agent may comprise a cysteine, e.g., wherein the functional group is a thiol of a cysteine.

A particle may comprise a plurality of reactive groups, wherein each reactive group comprises a thiol. A functional group may comprise a maleimide (e.g., a functional group of a linker or an agent), thereby allowing the functional group to bind a thiol of the particle.

A particle may comprise a first linker and a second linker, e.g., wherein the first linker is for linking a first agent to a reactive group and the second linker is for linking a second agent to a reactive group. A particle may comprise a first plurality of linkers and a second plurality of linkers. The first plurality of linkers and/or second plurality of linkers may comprise about 10 to about $10^9$ linkers, such as about $10^2$ to about $10^8$ linkers, about $10^3$ to about $10^7$ linkers, or about $10^4$ to about $10^6$ linkers.

A particle may comprise a first reactive group and a second reactive group, e.g., wherein the first reactive group is for binding a first functional group and the second reactive group is for binding a second functional group. A particle may comprise a first plurality of reactive groups and a second plurality of reactive groups. The first plurality of reactive groups and/or second plurality of reactive groups may comprise about 10 to about $10^9$ reactive groups, such as about $10^2$ to about $10^8$ reactive groups, about $10^3$ to about $10^7$ reactive groups, or about $10^4$ to about $10^6$ reactive groups. A first reactive group (or plurality of reactive groups) may be for linking an agent to the particle, for example, by binding a functional group of either the agent or a linker to the reactive group. A second reactive group (or plurality of reactive groups) may be for linking a second agent to the particle, for example, by binding either the second agent or a functional group of a linker (e.g., second linker) that may be used to link the second agent to the particle.

The first reactive group may be different from the second reactive group, e.g., such that the first reactive group may bind a first functional group and the second reactive group may bind a second functional group that is different from the first functional group. In some embodiments, the first reactive group is related to the second reactive group, e.g., such that the first reactive group and second reactive group bind the same functional group. When the first reactive group and second reactive group bind the same functional group, at least one of the first reactive group and second reactive group may be bound to a protecting group. In this embodiment, the first reactive group may be coupled to a functional group of a first agent or linker for binding the agent, for example, the second reactive group may be deprotected, and then the second reactive group may be coupled to a second agent.

Protecting groups are well known (Greene, T. W. and P. G. M. Wuts, PROTECTIVE GROUPS IN ORGANIC SYNTHESIS, 3rd edition, John Wiley & Sons, New York (1999), hereby incorporated by reference in its entirety) and exemplary groups are summarized below.

Amino-protecting groups include methyl carbamate, ethyl carbamate, 9-fluorenylmethyl carbamate (Fmoc), 9-(2-sulfo)fluorenylmethyl carbamate, dibromo)fluoroenylmethyl carbamate, 2,7-di-t-butyl-[9-10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl 1-2,2-dibromoethyl carbamate (DB-BOC), 1,1-dimethyl-2,2,2-trichloroethyl carbamate (TCBOC), 1-methyl-1-(4-biphenyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N1N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, hydroxypiperidinyl carbamate, alkyldithio carbamate, benzyl carbamate (Cbz), methoxybenzyl carbamate (Moz), p-nitobenzyl carbamate, bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonoisopropyl carbamate (Ppoc), 1,1-dimethyl-2-cyanoethyl carbamate, m-chloro-p-acyloxybenzyl carbamate, (dihydroxyboryl)benzyl carbamate, 5-benzi soxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N-phenylaminothiocarbonyl derivative, t-amyl carbamate, S-benzyl thiocarbamate, cyanobenzyl carbamate, cyclobutyl carbamate, cyclohexyl carbamate, cyclopentyl carbamate, cyclopropylmethyl carbamate, decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, (phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N-oxide, N-1,1-dimethylthiomethyleneamine, N-benzylideneamine, N-methoxybenzylideneamine, N-diphenylmethyleneamine, N-[(2-pyridyl)mesityl]methyleneamine, N—(N',N-dimethylaminomethylene) amine, N,N-isopropylidenediamine, nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonami de (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzyl sulfonamide, trifluoromethylsulfonamide, and phenacylsulfonamide.

Carboxylic acid protecting groups include silyl-, alkyl-, alkenyl-, aryl-, and arylalkyl-protected carboxylic acids.

Silyl protecting groups include trimethylsilyl, triethylsilyl, t-butyldimethylsilyl, t-butyldiphenylsilyl, triisopropylsilyl, and the like.

Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, benzyl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, chlorophenyl, p-methoxyphenyl, 2,4-dinitrophenyl, benzyl, methoxybenzyl, 3,4-dimethoxybenzyl, o-nitrobenzyl, nitrobenzyl, p-halobenzyl, 2,6-dichlorobenzyl, cyanobenzyl, phenylbenzyl, 2-picolyl, 4-picolyl, 3-methyl-2-picolylN-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (DMIPS), diethylisopropylsilyl (DEIPS), dimethylthexylsilyl, t-butyldimethylsilyl (TB S), t-butyldimethylsilyl (TBDMS), t-butyldiphenylsilyl (TBDPS), tribenzylsilyl, tri-xylylsilyl, triphenylsilyl, diphenylmethylsilyl (DPMS), t-butylmethoxyphenylsilyl (TBMPS), formate, benzoylformate, proprionate, acetate, chloroacetate, dichloroacetate, trichloroacetate, trifluoroacetate, methoxyacetate, triphenylmethoxyacetate, phenoxyacetate, chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphinio) ethyl carbonate (Peoc), alkyl isobutyl carbonate, alkyl vinyl carbonate, alkyl allyl carbonate, alkylnitrophenyl carbonate, alkyl benzyl carbonate, alkyl methoxybenzyl carbonate, alkyl 3,4-dimethoxy benzyl carbonate, alkyl o-nitrobenzyl carbonate, alkyl nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl) benzoate, 2-formylbenzene sulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

1,2- or 1,3-diol protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxy benzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(M,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Thiol protecting groups include thioesters, carbonates, sulfonates, allyl thioethers, thioethers, silyl thioethers, alkyl thioethers, arylalkyl thioethers, and alkyloxyalkyl thioethers.

Ester protecting groups include formates, acetates, propionates, pentanoates, crotonates, benzoates, formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxycrotonate, benzoate, p-benylbenzoate, 2,4,6-trimethylbenzoate. Carbonate ester protecting groups include 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl carbonate. Silyl ester protecting groups include trimethylsilyl, triethylsilyl, t-butyldimethylsilyl, t-butyldiphenylsilyl, triisopropylsilyl ether, and other trialkylsilyl ethers. Alkyl ester protecting groups include methyl, benzyl, p-methoxybenzyl, 3,4-dimethoxybenzyl, trityl, t-butyl, and allyl ether, and derivatives thereof. Arylalkyl ester protecting groups include benzyl, p-methoxybenzyl (PMB), 3,4-dimethoxybenzyl, o-nitrobenzyl, p-nitrobenzyl, p-halobenzyl, 2,6-dichlorobenzyl, p-cyanobenzyl, 2- and 4-picolyl ethers.

In some aspects, the invention relates to a method of making a particle as described herein, comprising incubating an unloaded particle (e.g., a particle comprising a reactive group) with a linker (e.g., a linker comprising a functional group), thereby forming a bond between the particle (e.g., a reactive group of the particle) and the linker (e.g., the functional group). See FIG. 8. In some embodiments, the method comprises incubating an unloaded particle (e.g., a particle comprising a plurality of reactive groups) with a plurality of linkers (e.g., wherein each linker comprises a functional group), thereby forming bonds between the particle (e.g., a population of reactive groups of the particle) and a population of linkers (e.g., the functional groups of the population of linkers). The method may comprise incubating a linker with an agent of the invention, thereby forming a bond between the linker and agent. In some embodiments, the method comprises incubating a plurality of linkers with a plurality of agents, thereby forming bonds between a population of linkers and a population of agents. In some embodiments, the reactive group, linker, functional group, and/or agent can form a bond with a carboxyl, primary amine, or thiol. In certain preferred embodiments, the reactive group and/or functional group can form a bond with a carboxyl, primary amine, or thiol.

A reactive group and/or functional group may comprise a biotin-binding protein (e.g., avidin, monomeric avidin, streptavidin, monomeric streptavidin, neutravidin, monomeric neutravidin) or biotin. For example, a reactive group may comprise biotin and a functional group may comprise a biotin-binding protein or a reactive group may comprise a biotin-binding protein and a functional group may comprise biotin. A linker may comprise a biotin-binding protein or biotin, e.g., wherein either a reactive group of the particle comprises biotin or a biotin-binding protein, respectively, or an agent comprises biotin or a biotin-binding protein, respectively. An agent may comprise a biotin-binding protein or biotin, e.g., wherein either a reactive group of the particle comprises biotin or a biotin-binding protein, respectively, or a linker comprises biotin or a biotin-binding protein, respectively.

A linker may comprise biotin and a thiol, biotin and an amine, or biotin and a carboxylic acid. For example, the linker may bind to an agent comprising a biotin-binding protein, and the functional group of the linker may be the thiol, amine, or carboxylic acid, i.e., for linking the agent to a particle. Similarly, the linker may bind to a particle comprising a biotin-binding protein (e.g., wherein the functional group of the linker is biotin), and the thiol, amine, or carboxylic acid of the linker may be used to crosslink an agent to the particle.

The reactive group, linker, functional group, and/or agent may comprise an α-haloacyl, alkene, alkyl halide, alkyne, amine, aryl azide, aryl halides, azide, carbodiimide, carboxyl, diene, dienophile, glyoxal, imidoester, isocyanide, maleimide, N-hydroxysuccinimidyl (NETS) ester, phosphine, tetrazine, or thiol, e.g., for bonding the agent to the particle. For example, the particle may comprise an amine-functionalized silica surface wherein the plurality of reactive groups are the amines. The reactive group, linker, functional group, and/or agent may comprise an antibody (or antigen-binding portion thereof), peptide, protein, nucleic acid, or aptamer.

The reactive group, linker, functional group, and/or agent may comprise an azide or alkyne, e.g., for immobilizing an agent via the azide-alkyne Huisgen cycloaddition. Huisgen cycloaddition is the reaction of a dipolarophile with a 1,3-dipolar compound that leads to 5-membered (hetero) cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitrile oxides, azides, and diazoalkanes. Metal catalyzed click chemistry is an extremely efficient variant of the Huisgen 1,3-dipolar cycloaddition reaction between alkyl-aryl)-sulfonyl azides, C—N triple bonds and C—C triple bonds, which is well-suited to the methods disclosed herein. The results of these reactions are 1,2-oxazoles, 1,2,3-triazoles or tetrazoles. For example, 1,2,3-triazoles are formed by a copper catalyzed Huisgen reaction between alkynes and alkyl/aryl azides. Metal-catalyzed Huisgen reactions proceed at ambient temperature, are not sensitive to solvents, i.e., nonpolar, polar, semipolar, and are highly tolerant of functional groups. Non-metal Huisgen reactions (also referred to as strain-promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity of the reaction components as compared to the metal-catalyzed reactions. Examples include DIFO and DIMAC. Reaction of the alkynes and azides is very specific and essentially inert against the chemical environment of biological tissues.

The reactive group, linker, functional group, and/or agent may comprise a thiol or an alkene, e.g., for immobilizing an agent via a thiol-ene reaction alkene (hydrothiolation, i.e., addition of RS—H across a C=C bond). The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene.

The reactive group, linker, functional group, and/or agent may comprise a diene or a dienophile, e.g., for immobilizing an agent via the Diels-Alder reaction. The Diels-Alder reaction combines a diene (a molecule with two alternating double bonds) and a dienophile (an alkene) to make rings and bicyclic compounds.

The reactive group, linker, functional group, and/or agent may comprise an isocyanide or a tetrazine, e.g., for immobilizing an agent via a 4+1 cycloaddition.

The reactive group, linker, functional group, and/or agent may comprise a maleimide or a thiol, e.g., for immobilizing an agent via a maleimide-thiol reaction (see, e.g., U.S. Patent Application Publication No. 2010/0036136, hereby incorporated by reference).

The reactive group, linker, functional group, and/or agent may comprise a phosphine or an azide, e.g., for immobilizing an agent via the Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on a triarylphosphine (usually in ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

Functional groups can be joined to agents through varying lengths of spacer arms or bridges, which may be alkyl chains, PEG chains, amino-acid chains, or any other suitable spacers. For example, a linker may comprise a polyethylene glycol (PEG) chain, e.g., which serves as a spacer between the functional group and the agent. A linker may comprise, for example, diethylene glycol, triethylene glycol, tetraethylene glycol, pentaethylene glycol, or hexaethylene glycol. A linker may comprise, for example a first functional group (e.g., R'), a polyethylene glycol spacer (e.g., —[OCH$_2$CH$_2$]$_n$O—, wherein n is an integer from 2 to 100, such as 2 to 50, or 2 to 20), and a second functional group (e.g., R$^2$).

For example, the linker may be a molecule of formula $R^1[OCH_2CH_2]_nOR^2$ or $R^2[OCH_2CH_2]_nOR^1$. $R^1$ and $R^2$ may each independently be selected from a moiety comprising an α-haloacyl, alkene, alkyl halide, alkyne, amine, aryl azide, aryl halides, azide, carbodiimide, carboxyl, diene, dienophile, glyoxal, imidoester, isocyanide, maleimide, N-hydroxysuccinimidyl (NHS) ester, phosphine, tetrazine, or thiol. $R^1$ may be thiol and $R^2$ may be carboxyl, or $R^2$ may be thiol and $R^1$ may be carboxyl. $R^1$ may be thiol and $R^2$ may be amine, or $R^2$ may be thiol and $R^1$ may be amine. $R^1$ may be carboxyl and $R^2$ may be amine, or $R^2$ may be carboxyl and $R^1$ may be amine.

Reactive groups and functional groups suitable for reacting with primary amines include imidoesters and N-hydroxysuccinimidyl (NHS) esters. Examples of imidoester functional groups include dimethyladipimidate, dimethylpimelimidate, and dimethylsuberimidate. Examples of NHS-ester functional groups include disuccinimidyl glutamate, disuccinimidyl suberate, and bis(sulfosuccinimidyl) suberate. Accessible amine groups present on the N-termini of peptides, polypeptides, and proteins react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines may be conducted at a pH of between about 7 and about 9 and a temperature between about 4° C. and 30° C. for about 30 minutes to about 2 hours. The concentration of NHS-ester functional group may vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl-reactive functional groups and reactive groups include maleimides, alkyl halides, aryl halides, and a-haloacyls which react with sulfhydryls to form thiol ether bonds and pyridyl disulfides which react with sulfhydryls to produce mixed disulfides. Sulfhydryl groups on peptides, polypeptides, and proteins can be generated by techniques known to those with skill in the art, e.g., by reduction of disulfide bonds or addition by reaction with primary amines using 2-iminothiolane. Examples of maleimide functional groups include succinimidyl 4-{N-maleimido-methyl)cyclohexane-1-carboxylate and m-maleimidobenzoyl-N-hydroxysuccinimide ester. Examples of haloacetal functional groups include N-succinimidyl (4-iodoacetal) aminobenzoate and sulfosuccinimidyl (4-iodoacetal) aminobenzoate. Examples of pyridyl disulfide functional groups include 1,4-di-[3'-2'-pyridyldithio(propionamido)butane] and N-succinimidyl-3-(2-pyridyldithio)-propionate.

Reactive groups and/or functional groups may comprise carboxyl groups for binding to primary amines or hydrazides by using carbodiimides, which result in formation of amide or hydrazone bonds. In this manner, carboxy-termini of peptides, polypeptides, and proteins can be immobilized on a particle. Examples of carbodiimide functional groups and reactive groups include 1-ethyl-3-(3-dimethylaminopropyl)-carbodiimide hydrochloride and N,N$^1$-dicyclohexylcarbodiimide. Arylazide becomes reactive when exposed to ultraviolet radiation to form aryl nitrene. Examples of arylazide functional groups include azidobenzoyl hydrazide and N-5-azido-2 nitrobenzoyloxysuccinimide. Glyoxal functional groups target the guanidyl portion of arginine. An example of a glyoxal functional group is p-azidophenyl glyoxal monohydrate.

Heterobifunctional linkers which possess two or more different functional groups (e.g., a first functional group, a second functional group, and optionally additional functional groups) are suitable for use herein. Examples include linkers that are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide linkers discussed above. Such linkers can be used to indirectly join a reactive group of the particle with a functional group of the agent.

An agent may be immobilized on a particle by binding to a reactive group. For example, a peptide, polypeptide, or protein may be immobilized by forming a bond between a carboxyl, primary amine, or thiol of the peptide, polypeptide, or protein and a reactive group. Alternatively, an agent may be modified, e.g., with a linker, to form a bond with a reactive group. Various methods for modifying an agent, such as a protein, carbohydrate, or lipid, are known in the art (see, e.g., U.S. Patent Application Publication Nos. 2014/0212425, 2014/0377837, and 2015/0005447, and U.S. Pat. Nos. 4,711,955, 5,047,519, 7,332,355, 9,040716, hereby incorporated by reference).

1,3-Dipolar compounds can be incorporated into proteins, lipids, oligosaccharides, oligonucleotides, and glycans using metabolic machinery, covalent inhibitors, and enzymatic transfers. For example, an azido group, $N_3$, can be applied at the N-terminus of proteins or peptides using azidoacetyl chloride (see, e.g., Haridas, et al., Tetrahedron Letters 48 (2007) 4719-4722). The azido group is a nucleophilic group that will exchange with other nucleophilic groups, e.g., OH, $NH_2$ and halogens (Br, Cl, or I). $NaN_3$ is an azidizing agent which is capable of aziding proteins by simply contacting the proteins with a 10 times molar excess of $NaN_3$. A process for C-terminal azidization is described in Cazalis, et al., Bioconjugate Chem., 15 (2004) 1005-1009. The incubation of cells with peracetylated N-azidoacetylmannosamine provides cell surface glycans with azido sialic acid (see, e.g., Codelli et al., J. Amer. Chem. Soc., 130 (34) 11486-11493 (2008)). Azido-tagged lipids are described in Smith, et al., Bioconjugate Chem., 19 (9), 1855-1863 (2008). PEGylation is a commonly used technique for adding groups to peptides and proteins and is suitable for use herein. For example, PEG may be covalently bound to amino acid residues via a reactive moiety. Reactive moieties (as opposed to reactive groups herein) are those to which an activated PEG molecule may be bound (e.g., a free amino or carboxyl group). For example, N-terminal amino acid residues and lysine residues have a free amino group and C-terminal amino acid residues have a free carboxyl group. Sulfhydryl groups (e.g., as found on cysteine residues) may also be used as a reactive moiety for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein. Those skilled in the art can utilize any known process for coupling a 1,3-dipolar compound into proteins, lipids, oligosaccharides, oligonucleotides and glycans.

A particle may comprise a reactive group comprising an azido group or an alkynyl group and a linker or agent (e.g., a functional group of a linker or agent) may comprise an alkynyl group or azido group, respectively. An alkynyl group may form a covalent bond with an azido group, for example, using a copper-catalyzed alkyne-azide cycloaddition. Methods for preparing particles comprising an azido group or an alkynyl group are known (see, e.g., Xu, Z. et al. J Nanoparticle Research 17:56 (2015)).

Dipolarophile-functionalized proteins, polypeptides, and peptides can be synthesized by linking at the N-terminus with, for example, an alkyne (e.g., 3-butynyl chloroformate). In some embodiments, thiols on cysteines are functionalized with alkyne bearing maleimide. Providing a C-terminal dipolarophile can be accomplished, e.g., by coupling with propargylamine using a linking agent such as N-hydroxysuccinimide/DCC. Terminal alkynes can be installed using metabolic building blocks such as alkynoic acids. Lipids may be functionalized with alkynes. For example, alkyne-modified fatty acids can be generated by reaction of terminal alkynyl-alkyl bromide with trimethyl phosphine to yield a 16 carbon alkynyl-dimethylphosphonate (see, e.g., Raghavan et al., Bioorg. Med. Chem. Lett., 18 (2008) 5982-5986). As above, PEGylation may be used for adding dipolarophile groups to peptides and proteins and is suitable for use herein. Diels-Alder functionalities and thiol-ene functionalities may likewise be attached to proteins, lipids, oligosaccharides, oligonucleotides and glycans.

In certain preferred embodiments, the reactive group comprises a nucleic acid, e.g., for hybridizing with an agent or functional group (e.g., an agent or functional group that comprises a complementary nucleic acid). The term "nucleic acid" refers to DNA or RNA. A nucleic acid may be single stranded or double stranded. A nucleic acid may comprise single stranded regions and/or double stranded regions. A nucleic acid comprises a nucleotide sequence, which is the order of consecutive nucleotides in the nucleic acid, read from 5' to 3'. A nucleic acid may comprise multiple nucleotide sequences. For example, a double stranded nucleic acid comprises two nucleotide sequences that each span the length of the nucleic acid, wherein one nucleotide sequence may be the reverse complement of the other nucleotide sequence. A nucleic acid also comprises nucleotide sequences that are shorter than the length of the nucleic acid. For example, a single stranded nucleic acid that is ten nucleotides long has two nucleotide sequences that are nine nucleotides long. Similarly, a single stranded nucleic acid that is ten nucleotides long has three nucleotide sequences that are eight nucleotides long. The nucleotides of a nucleic acid may be, for example, cytosine (C), guanine (G), adenine (A), thymine (T), and/or uracil (U). The nucleotides may be modified or unmodified. For example, one or more nucleotides may be methylated. A nucleic acid may comprise a nucleotide analog and/or an unnatural base pair. The nucleotides of a nucleic acid may comprise 5-methylcytosine, pseudouridine, dihydrouridine, inosine, xanthosine, and/or 7-methylguanosine.

A particle may comprise a reactive group, wherein the reactive group comprises a nucleic acid; and an agent, wherein the agent is linked to a complementary nucleic acid that can hybridize with the nucleic acid of the reactive group, thereby forming a non-covalent association between the agent and the particle. Similarly, a particle may comprise a reactive group, wherein the reactive group comprises a nucleic acid; and a functional group, wherein the functional group comprises a complementary nucleic acid that can hybridize with the nucleic acid of the reactive group, thereby forming a non-covalent association between the agent and the particle. The nucleic acid may comprise a nucleotide sequence and the complementary nucleic acid may comprise a complementary nucleotide sequence, e.g., wherein the nucleotide sequence has at least 95%, 96%, 97%, 98%, or 99% sequence identity with the reverse complement of the complementary nucleotide sequence. The nucleotide sequence may have 100% sequence identity with the reverse complement of the complementary nucleotide sequence.

Preferably, the melting temperature of the nucleic acid and complementary nucleic acid in physiological fluid (e.g., blood) is greater than body temperature (e.g., the body temperature of a subject, such as a human or mouse). For example, the melting temperature of the nucleic acid and complementary nucleic acid in physiological fluid is preferably greater than 37° C., such as greater than about 38° C., greater than about 39° C., greater than about 40° C., greater than about 41° C., greater than about 42° C., greater than about 43° C., greater than about 44° C., or greater than about 45° C. The melting temperature of the nucleic acid and complementary nucleic acid may be about 37° C. to about 120° C., such as about 38° C. to about 120° C., about 39° C. to about 120° C., about 40° C. to about 120° C., about 41° C. to about 120° C., about 42° C. to about 120° C., about 43° C. to about 120° C., about 44° C. to about 120° C., about 45° C. to about 120° C., about 46° C. to about 120° C., about 47° C. to about 120° C., about 48° C. to about 120° C., about 49° C. to about 120° C., about 50° C. to about 120° C., about 38° C. to about 100° C., about 39° C. to about 100° C., about 40° C. to about 100° C., about 41° C. to about 100° C., about 42° C. to about 100° C., about 43° C. to about 100° C., about 44° C. to about 100° C., about 45° C. to about 100° C., about 46° C. to about 100° C., about 47° C. to about 100° C., about 48° C. to about 100° C., about 49° C. to about 100° C., or about 50° C. to about 100° C.

The length of the nucleic acid of the reactive group, nucleotide sequence of the reactive group, complementary nucleic acid, and complementary nucleotide sequence is preferably greater than 9 nucleotides. The length of the nucleic acid of the reactive group, nucleotide sequence of the reactive group, complementary nucleic acid, and complementary nucleotide sequence may be greater than 10, 11, 12, 13, 14, 15, 16, 17, 18, 19, or 20 nucleotides. The length of the nucleic acid of the reactive group, nucleotide sequence of the reactive group, complementary nucleic acid, and complementary nucleotide sequence may be about 10 nucleotides to about 100 nucleotides, such as about 11 nucleotides to about 80 nucleotides, about 12 nucleotides to about 60 nucleotides, about 13 nucleotides to about 50 nucleotides, about 14 nucleotides to about 40 nucleotides, about 15 nucleotides to about 30 nucleotides, or about 16 nucleotides to about 25 nucleotides. The GC content of the nucleic acid, nucleotide sequence, complementary nucleic acid, and complementary nucleotide sequence may be about 10% to about 100%, such as about 40% to about 100%, about 45% to about 100%, about 50% to about 100%, about 55% to about 100%, about 40% to about 95%, about 45% to about 90%, about 50% to about 85%, or about 55% to about 80%.

XII. Positioning of an Agent on a Particle

In some embodiments, the geometry of the particle is such that the immobilized agent has a reduced, or substantially reduced, ability to interact with a biomolecule on the surface of a cell, such as an immune cell, blood cell, or lymphocyte. An immobilized agent may have less than 50% (e.g., 45, 40, 35, 30, 25, 20, 15, 10, 9, 8, 7, 6, 5, 4, 3, 2, or 1%) of the ability to bind to a biomolecule on a surface of a cell relative to a free, soluble form of the agent. For example, in some embodiments, TNFα or IL-2 immobilized on the surface of a particle described herein has less than 50 (e.g., 45, 40, 35, 30, 25, 20, 15, 10, 9, 8, 7, 6, 5, 4, 3, 2, or 1) % of the ability of free TNFα or IL-2 to bind to a TNFα receptor or IL-2 receptor on the surface of a cell.

In some embodiments, the soluble biomolecule bound to the particle has a reduced, or substantially reduced, ability to interact with its cognate ligand (the second member of the specific binding pair). The biomolecule may be bound to the particle by virtue of the agent. A biomolecule bound to a particle may have less than 50% (e.g., 45, 40, 35, 30, 25, 20, 15, 10, 9, 8, 7, 6, 5, 4, 3, 2, or 1%) of the ability to interact with its cognate ligand relative to the ability of an unbound, biomolecule. For example, a soluble TNFR bound to a particle described herein has less than 50 (e.g., 45, 40, 35, 30, 25, 20, 15, 10, 9, 8, 7, 6, 5, 4, 3, 2, or 1) % of the ability of free, soluble TNFR to interact with free TNFα. In another example, a soluble virion bound to a particle described herein has less than 50 (e.g., 45, 40, 35, 30, 25, 20, 15, 10, 9, 8, 7, 6, 5, 4, 3, 2, or 1) % of the ability of free virion to interact with its cognate cell surface receptor(s) and infect a cell.

In some embodiments, the agent may be immobilized on an inner surface of a particle (e.g., the pores of a porous particle or the inner surface of a tube). In some embodiment, the agent can be immobilized on the outer surface of a particle, but is sterically precluded from interacting with a cell surface by way of one or more protrusions from the particle. In some embodiments, e.g., toroidal particles, the agent is immobilized on the inner surface of the particle such that the agent has a reduced, or substantially reduced, ability to interact with a biomolecule on the surface of a cell and/or the soluble biomolecule bound to the particle by virtue of the agent has a reduced, or substantially reduced, ability to interact with its cognate ligand (the second member of the specific binding pair).

Exemplary particle geometries capable of reducing or substantially reducing the interaction of an agent with a biomolecule on a cell surface, or the interaction between a biomolecule bound to the particle, and its cognate ligand, are set forth in FIGS. 1 to 6 and described herein.

XIII. Clearance Agents and Coatings

In some embodiments, a particle comprises a clearance agent. The clearance agent may facilitate clearance of the particle through a biological pathway, such as by excretion in the urine, degradation, excretion by a hepatobiliary pathway, and/or phagocytosis.

For example, the particle may comprise a reservoir, wherein the reservoir comprises a clearance agent. The reservoir may be a hole or void in the body of a particle, e.g., a void in the body of a porous silicon particle.

For particles comprising pores, the reservoir may be a pore or the reservoir may be larger or smaller than the average pore size. A reservoir may consist of a recess in the body of a particle (e.g., a shallow recess), wherein the width or diameter of the recess is larger than the width or diameter of the average pore size. The width or diameter of a reservoir may be at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 175, 200, 250, 300, 400, or even about 500 times as large as the width or diameter of the average pore size. The width or diameter of the reservoir may be about 2 times to about 10 times the width or diameter of the average pore size, such as about 2 times to about 8 times or about 2 times to about 6 times. The width or diameter of a reservoir may be about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 90, 100, 110, 120, 130, 140, 150, 175, 200, 250, 300, 400, or even about 500 times as large as the width or diameter of the average pore size.

For particles comprising a DNA scaffold, a reservoir may be an interior region of the DNA scaffold. The reservoir (e.g., interior region) may be inaccessible to cells, e.g., the DNA scaffold may be constructed such that the scaffold sterically hinders cells from entering the interior region. In some embodiments, the reservoir (e.g., interior region) is inaccessible to extracellular proteins, e.g., the DNA scaffold may be constructed such that the scaffold sterically hinders extracellular proteins from entering the reservoir. The reservoir (e.g., interior region) may be inaccessible to antibodies. Nevertheless, the DNA scaffold may allow for the reservoir (e.g., interior region) to become accessible to cells and/or extracellular proteins after a predetermined period of time. For example, the DNA scaffold may comprise a biodegradable wall that may degrade after a predetermined period of time (e.g., by hydrolysis), thereby exposing the clearance agent to cells and/or extracellular proteins. The DNA scaffold may comprise a biodegradable latch that may degrade after a predetermined period of time (e.g., by hydrolysis), allowing the DNA scaffold to undergo a conformational change, thereby exposing the clearance agent to cells and/or extracellular proteins (see, e.g., PCT Patent Application Publication No. WO2014/170899, hereby incorporated by reference). Similarly, the DNA scaffold may comprise a reservoir that comprises and opening, as described below.

The reservoir may comprise an opening. The opening may be covered by a cap or member, thereby inhibiting interactions between the clearance agent and cells and/or extracellular proteins (e.g., antibodies). The cap or member may comprise a polymer, such as a biodegradable polymer. The cap or member may degrade after a predetermined period of time (e.g., by hydrolysis), thereby exposing the clearance agent to cells and/or extracellular proteins. The cap or member may degrade (e.g., biodegrade) after exposure to a biological fluid (e.g., blood plasma or extracellular fluid) for about 1 day to about 5 years, such as about 1 day to about 4 years, about 1 day to about 3 years, or about 1 day to about 1 year.

A predetermined period of time may be a period of time that the particle is in a liquid (e.g., an aqueous liquid). The predetermined period of time may be a period of in vivo residence of a particle (e.g., exposure to biological fluids, pH, enzymes, and/or temperatures). The predetermined period of time may be determined, at least in part, by the binding of the particle to a biomolecule. For example, the particle may be configured such that the binding of a biomolecule exposes the clearance agent to cells and/or extracellular proteins (see, e.g., PCT Patent Application Publication No. WO2014/170899, hereby incorporated by reference). The predetermined period of time may be about 1 day to about 5 years, such as about 1 day to about 3 years, or about 1 day to about 1 year.

Exemplary materials suitable for use as caps or membranes, are described in U.S. Pat. No. 7,918,842, which is hereby incorporated by reference. In general, these materials degrade or dissolve either by enzymatic hydrolysis or exposure to water in vivo or in vitro, or by surface or bulk erosion. Representative synthetic, biodegradable polymers include: poly(amides) such as poly(amino acids) and poly (peptides); poly(esters) such as poly(lactic acid), poly(glycolic acid), poly(lactic-co-glycolic acid), and poly(caprolactone); poly(anhydrides); poly(orthoesters); poly (carbonates); and chemical derivatives thereof (substitutions, additions of chemical groups, for example, alkyl, alkylene, hydroxylations, oxidations, and other modifications routinely made by those skilled in the art), copolymers and mixtures thereof. Other polymers that may be used in caps or membranes include: poly(ethers) such as poly(ethylene oxide), poly(ethylene glycol), and poly(tetramethylene oxide); vinyl polymers-poly(acrylates) and poly(methacrylates) such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; poly (siloxanes); and any chemical derivatives thereof (substitutions, additions of chemical groups, for example, alkyl, alkylene, hydroxylations, oxidations, and other modifications routinely made by those skilled in the art), copolymers and mixtures thereof. In certain embodiments, the reservoir cap is formed from one or more cross-linked polymers, such as cross-linked polyvinyl alcohol.

In some embodiments, a particle comprises a coating. In some embodiments, the coating comprises a clearance agent. The coating may mask a clearance agent.

The particle may comprise a first surface and a second surface; the agent may be immobilized on the first surface; and the coating may cover at least a portion of the second surface. The first surface may be an interior surface or an inner surface, e.g., the first surface may be oriented such that the agent has a reduced ability to bind to a molecule on a cell surface. Examples of an interior surface or inner surface include the inner walls of a pore, reservoir, or tube, the inner circumferential surface of a toroid, or the hollow of a concave surface. Other examples of an interior surface or inner surface include the outer surface of a particle, wherein the outer surface is protected from interactions with cells by one or more protrusions. The second surface may be an exterior surface or outer surface, e.g., the second surface may be oriented such that the coating can interact with a cell. In some embodiments, a particle may comprise one or more core subparticles and a plurality of protecting subparticles. The particle may comprise a shield and the shield may comprise the plurality of protecting subparticles. The first surface may be the surface of the one or more core particles and the second surface may be the surface of the protecting subparticles.

A coating may inhibit interactions between particles, e.g., the coating may reduce the propensity of particles to form aggregates. The coating may inhibit interactions between a particle and cells, e.g., by presenting a biologically-inert surface. The coating may inhibit non-specific interactions with extracellular molecules, e.g., non-specific adsorption of biomolecules. A coating may inhibit specific interactions with cells or extracellular molecules, e.g., a coating may disfavor or delay the excretion or phagocytosis of a particle. A coating may target a particle for excretion or phagocytosis. A coating or other feature (e.g., an "excretion-inducing compound") that targets a particle for excretion or phagocytosis may be masked by a coating (e.g., a second coating) that delays the excretion or phagocytosis of the particle, e.g., to promote maintenance of the particles in the bloodstream for a predetermined amount of time.

A coating may comprise a plurality of elongated coating molecules bound at one end to the surface of the particle. A coating may inhibit interactions between a biomolecule bound to a particle and a second member of the specific binding pair that includes the biomolecule. A coating may inhibit interactions between a biomolecule bound to a particle and a cell. An agent may be oriented on a particle relative to a coating such that the agent has a reduced ability to bind to a molecule on the surface of a cell. An agent may be oriented on a particle relative to a coating such that the agent has a reduced ability to bind to a target on the surface of a cell. An agent may be oriented on a particle relative to a coating such that the coating sterically inhibits the agent from binding to a molecule on the surface of a cell. An agent may be oriented on a particle such that the coating sterically inhibits the agent from binding to a target on the surface of a cell. A coating may be oriented on a particle such that the agent of the particle has a reduced ability to bind to a molecule on the surface of a cell. A coating may reduce the ability of the agent of a particle to activate a cell surface receptor protein, relative to the ability of a natural ligand of the cell surface receptor protein.

A particle may comprise a second coating, e.g., wherein the second coating consists of a second plurality of coating molecules. A particle may comprise a second plurality of coating molecules. The second coating and/or second plurality of coating molecules may decrease the clearance of the particle in vivo, e.g., by masking the coating and/or plurality of coating molecules. The second coating and/or second plurality of coating molecules may be biodegradable, e.g., to expose the coating and/or plurality of coating molecules to cells and/or extracellular proteins after a predetermined period of time. The second coating and/or second plurality of coating molecules may comprise a biodegradable polymer, e.g., each molecule of the second plurality of coating molecules may comprise a biodegradable polymer. The second coating and/or second plurality of coating molecules may comprise CD47, which inhibits phagocytosis.

In some embodiments, the particle comprises a first surface (e.g., an interior surface) and a second surface (e.g., an exterior surface or outer surface); the agent is immobilized on the first surface; and the coating covers at least a portion of the second surface. The orientation of the first surface may reduce the ability of the agent to interact with molecules on a cell surface. The orientation of the second surface may permit interactions between the coating and cells, extracellular molecules, and/or different particles. An "interaction" between the coating and cells, extracellular molecules, and/or different particles may be a weak, neutral, or unfavorable interaction, e.g., to disfavor stable binding of the particle to a cell, extracellular molecule, or other particle. Alternatively, an interaction between the coating and either cells and/or extracellular molecules may be a specific or designed interaction, e.g., to favor clearance of the particle through a biological pathway, such as phagocytosis. In certain preferred embodiments, the second surface is substantially free of agent. In certain preferred embodiments, the first surface is substantially free of coating. In certain preferred embodiments, the coating covers substantially all of the second surface.

In some embodiments, the particle comprises a first surface (e.g., an interior surface) and a second surface (e.g., an exterior surface or outer surface); the agent is immobilized on the first surface and the second surface; and the coating covers at least a portion of the second surface. In such embodiments, the coating (and/or a second coating) may inhibit interactions between the agent and molecules on a cell surface. In certain preferred embodiments, the coating covers substantially all of the second surface.

In some embodiments, the particle comprises a first surface (e.g., an interior surface) and a second surface (e.g., an exterior surface or outer surface); the agent is immobilized on the first surface; and the coating covers at least a portion of the first surface and at least a portion of the second surface. In such embodiments, the coating preferably does not affect the ability of the agent to specifically bind to a biomolecule. In certain preferred embodiments, the coating covers substantially all of the second surface.

In some embodiments, the particle comprises a surface; the agent is immobilized on the surface; and the coating covers at least a portion of the surface. In such embodiments, the coating may not affect the ability of the agent to specifically bind to a biomolecule. The coating may allow for some of the agent to specifically bind to a biomolecule and inhibit interactions between some of the agent and biomolecule. The coating may inhibit interactions between the agent and molecules on a cell surface. In certain preferred embodiments, the coating covers substantially all of the surface.

In some embodiments, the particle comprises a coating that covers at least a portion of the second surface and a second coating that covers at least a portion, such as substantially all, of the coating on the second surface. In such embodiments the coating may comprise a clearance agent, such as an "excretion-inducing compound" to target a particle for excretion or phagocytosis. Such a coating may comprise beta-cyclodextrin. The second coating may comprise a material, e.g., a second plurality of coating molecules, to inhibit interaction with cells and/or inhibit non-specific interactions with extracellular molecules, e.g., non-specific adsorption of biomolecules. The second coating may be biodegradable, e.g., to expose the coating on the second surface to cells and/or extracellular proteins after a predetermined period of time. For example, in a particle comprising one or more core subparticles and a plurality of protecting sub-particles, wherein a capture agent is immobilized on the surface on the core subparticle(s) (i.e., the first surface), at least a portion of the surface of the protecting subparticles (i.e., the second surface) comprises a coating, for example a coating comprising either a clearance agent or a coating comprising a material to inhibit interaction with cells and/or to inhibit non-specific interaction with extracellular molecules.

A coating may comprise coating molecules, e.g., a coating may consist of a plurality of coating molecules or a coating may consist of a population of coating molecules. As used herein, the terms "plurality of coating molecules" and "population of coating molecules" each refer to a coating. The term "coating," however, may refer to additional compositions, such as a hydrogel. A coating molecule may be a clearance agent (and thus, a clearance agent may be a coating molecule).

A particle may comprise a plurality of coating molecules. The particle may comprise a surface and a plurality of agents immobilized on the surface, and at least one molecule of the plurality of coating molecules may be bound to the surface. For example, all or substantially all of the molecules of the plurality of coating molecules may be bound to the surface.

The particle may comprise a surface and a second surface, wherein a plurality of agents immobilized on the surface, and at least one molecule of the plurality of coating molecules may be bound to the second surface. For example, all or substantially all of the molecules of the plurality of coating molecules may be bound to the second surface. In some embodiments, some of the molecules of the plurality of coating molecules are bound to the surface and some of the molecules of the plurality of coating molecules are bound to the second surface.

In some embodiments, the coating molecules increase the clearance of the particle in vivo. For example, the coating molecules may comprise a pathogen-associated molecular pattern.

In some embodiments, the particles described herein have a coating comprising an excretion-inducing compound, which facilitates the removal of the particles from the circulation, e.g., via the kidneys, liver/intestines (e.g., via bile), or phagocytosis (e.g., by antigen-presenting cells). A plurality of coating molecules may be a plurality of excretion-inducing compounds. For example, in embodiments in which the particles are toroidal, the inner circumferential surface (e.g., a first surface) may comprise an immobilized agent and the outer surface (e.g., a second surface) may comprise a compound that induces the clearance of the particles, e.g., by the kidneys, liver, or macrophages. In some embodiments, the excretion-inducing compound is programmed. That is, the compound can be covered with a coating that degrades (e.g., through the action of enzymes, hydrolysis, or gradual dissolution) over time (e.g., a predetermined amount of time) eventually exposing the excretion-inducing compound or other feature that increases the rate of clearance. The coating may degrade after exposure to a biological fluid (e.g., blood plasma or extracellular fluid) for about 1 day to about 5 years, such as about 1 day to about 3 years, or about 1 day to about 1 year. Thus, the in vivo residence of a particle may be modified and/or controlled.

A coating may comprise an organic polymer, such as polyethylene glycol (PEG). An organic polymer may be attached to a particle, e.g., attached to a surface of the particle. The organic polymer may include PEG, polylactate, polylactic acids, sugars, lipids, polyglutamic acid, polyglycolic acid (PGA), polylactic acid (PLA), poly(lactic-co-glycolic acid) (PLGA), polyvinyl acetate (PVA), and combinations thereof. In certain embodiments, the particle is covalently conjugated with PEG, which discourages adsorption of serum proteins, facilitates efficient urinary excretion and decreases aggregation of the particle (see, e.g., Burns et al., Nano Letters, 9(1):442-448 (2009) and U.S. Patent Application Publication Nos. 2013/0039848 and 2014/0248210, each of which is hereby incorporated by reference).

In one embodiment, the coating comprises at least one hydrophilic moiety, for example, Pluronic® type polymers (a nonionic polyoxyethylene-polyoxypropylene block co-polymer with the general formula $HO(C_2H_4O)_a(-C_3H_6O)_b(C_2H_4O)_aH)$, a triblock copolymer poly(ethylene glycol-b-(DL-lactic acid-co-glycolic acid)-b-ethylene glycol) (PEG-PLGA-PEG), a diblock copolymer polycaprolactone-PEG (PCL-PEG), poly(vinylidene fluoride)-PEG (PVDF-PEG), poly(lactic acid-co-PEG) (PLA-PEG), poly (methyl methacrylate)-PEG (PMMA-PEG) and so forth. In an embodiment with such a moiety, the hydrophilic moiety is a PEG moiety such as: a [Methoxy(Polyethyleneoxy)Propyl]-Trimethoxysilane (e.g., $CH_3(OC_2H_4)_{6-9}(CH_2)OSi(OCH_3)_3$), a [Methoxy(Polyethyleneoxy)Propyl]-Dimethoxysilane (e.g., $CH_3(OC_2H_4)_{6-9}(CH_2)OSi(OCH_3)_2$), or a [Methoxy(Polyethyleneoxy)Propyl]-Monomethoxysilane (e.g., $CH_3(OC_2H_4)_{6-9}(CH_2)OSi(OCH_3)$). Suitable coatings are described, for example, in U.S. Patent Application Publication No. 2011/0028662 (hereby incorporated by reference).

The coating may include a polyhydroxylated polymer, such as natural polymers or hydroxyl-containing polymers including multiply-hydroxylated polymers, polysaccharides, carbohydrates, polyols, polyvinyl alcohol, poly amino acids such as polyserine, or other polymers such as 2-(hydroxyethyl)methacrylate, or combinations thereof. In some embodiments, the polyhydroxylated polymers are polysaccharides. Polysaccharides include, mannan, pullulan, maltodextrin, starches, cellulose, and cellulose derivatives, gums, xanthan gum, locust bean gum, or pectin, combinations thereof (see, e.g., U.S. Patent Application Publication No. 2013/0337070, hereby incorporated by reference).

In some embodiments, the coating comprises a zwitterionic polymer (see, e.g., U.S. Patent Application Publication Nos. 2014/0235803, 2014/0147387, 2013/0196450, and 2012/0141797; and U.S. Pat. No. 8,574,549, each of which is hereby incorporated by reference).

Other suitable coatings include poly-alpha hydroxy acids (including polyactic acid or polylactide, polyglycolic acid, or polyglycolide), poly-beta hydroxy acids (such as polyhydroxybutyrate or polyhydroxyvalerate), epoxy polymers (including polyethylene oxide (PEO)), polyvinyl alcohols, polyesters, polyorthoesters, polyamidoesters, polyesteramides, polyphosphoesters, and polyphosphoester-urethanes. Examples of degradable polyesters include: poly (hydroxyalkanoates), including poly(lactic acid) or (polylactide, PLA), poly(glycolic acid) or polyglycolide (PGA), poly(3-hydroxybutyrate), poly(4-hydroxybutyrate), poly(3-hydroxyvalerate), and poly(caprolactone), or poly (valerolactone). Examples of polyoxaesters include poly (alkylene oxalates) such as poly(ethylene oxalate)) and polyoxaesters containing amido groups. Other suitable coating materials include polyethers including polyglycols, ether-ester copolymers (copoly(ether-esters)) and polycarbonates. Examples of biodegradable polycarbonates include polyorthocarbonates, polyiminocarbonates, polyalkylcarbonates such as poly(trimethylene carbonate), poly(1,3-dioxan-2-one), poly(p-dioxanone), poly(6,6-dimethyl-1,4-dioxan-2-one), poly(1,4-dioxepan-2-one), and poly(1,5-dioxepan-2-one). Suitable biodegradable coatings can also include polyanhydrides, polyimines (such as poly(ethylene imine) (PEI)), polyamides (including poly-N-(2-hydroxypropyl)-methacrylamide), poly(amino acids) (including a polylysine such as poly-L-lysine, or a polyglutamic acid such as poly-L-glutamic acid), polyphosphazenes (such as poly(phenoxy-co-carboxylatophenoxy phosphazene), polyorganophosphazenes, polycyanoacrylates and polyalkylcyanoacrylates (including polybutylcyanoacrylate), polyisocyanates, and polyvinylpyrrolidones.

The chain length of a polymeric coating molecule may be about 1 to about 100 monomer units, such as about 4 to about 25 units.

A particle may be coated with a naturally occurring polymer, including fibrin, fibrinogen, elastin, casein, collagens, chitosan, extracellular matrix (ECM), carrageenan, chondroitin, pectin, alginate, alginic acid, albumin, dextrin, dextrans, gelatins, mannitol, n-halamine, polysaccharides, poly-1,4-glucans, starch, hydroxyethyl starch (HES), dialdehyde starch, glycogen, amylase, hydroxyethyl amylase, amylopectin, glucoso-glycans, fatty acids (and esters thereof), hyaluronic acid, protamine, polyaspartic acid, polyglutamic acid, D-mannuronic acid, L-guluronic acid, zein and other prolamines, alginic acid, guar gum, and phosphorylcholine, as well as co-polymers and derivatives thereof. The coating may also comprise a modified polysaccharide, such as cellulose, chitin, dextran, starch, hydroxyethyl starch, polygluconate, hyaluronic acid, and elatin, as well as co-polymers and derivative thereof.

A particle may be coated with a hydrogel. The hydrogel can be formed, for example, using a base polymer selected from any suitable polymer, such as poly(hydroxyalkyl (meth)acrylates), polyesters, poly(meth)acrylamides, poly (vinyl pyrrolidone), or polyvinyl alcohol. A cross-linking agent can be one or more of peroxides, sulfur, sulfur dichloride, metal oxides, selenium, tellurium, diamines, diisocyanates, alkyl phenyl disulfides, tetraalkyl thiuram disulfides, 4,4'-dithiomorpholine, p-quinine dioxime and tetrachloro-p-benzoquinone. Also, boronic acid-containing polymers can be incorporated in hydrogels, with optional photopolymerizable groups.

In certain preferred embodiments, the coating comprises a material that is approved for use by the U.S. Food and Drug Administration (FDA). These FDA-approved materials include polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS).

The attachment of a coating to a particle may be accomplished by a covalent bond or a non-covalent bond, such as by ionic bond, hydrogen bond, hydrophobic bond, coordination, adhesive, or physical absorption or interaction.

Conventional nanoparticle coating methods include dry and wet approaches. Dry methods include: (a) physical vapor deposition (Zhang, Y. et al., Solid State Commun. 115:51 (2000)), (b) plasma treatment (Shi, D. et al., Appl. Phys. Lett. 78:1243 (2001); Vollath, D. et al., J. Nanoparticle Res. 1:235 (1999)), (c) chemical vapor deposition (Takeo, O. et al., J. Mater. Chem. 8:1323 (1998)), and (d) pyrolysis of polymeric or non-polymeric organic materials for in situ precipitation of nanoparticles within a matrix (Sglavo, V. M. et al., J. Mater Sci. 28:6437 (1993)). Wet methods for coating particles include: (a) sol-gel processes and (b) emulsification and solvent evaporation techniques (Cohen, H. et al., Gene Ther. 7:1896 (2000); Hrkach, J. S. et al., Biomaterials 18:27 (1997); Wang, D. et al., J. Control. Rel. 57:9 (1999)). A coating may be applied by electroplating, spray coating, dip coating, sputtering, chemical vapor deposition, or physical vapor deposition. Additionally, methods for coating various nanoparticles with polysaccharides are known in the art (see, e.g., U.S. Pat. No. 8,685,538 and U.S. Patent Application Publication No. 2013/0323182, each of which is hereby incorporated by reference).

In some embodiments, the particles may be adapted to facilitate clearance by renal excretion. Renal clearance for subjects with normal renal function generally requires particles with at least one dimension that is less than 15 nm (see, e.g., Choi, H. S., et al., Nat Biotechnol 25(1):1165 (2007); Longmire, M. et al., Nanomedicine 3(5):703 (2008)). Nevertheless, larger particles may be excreted in the urine. For embodiments in which a particle is too large for renal clearance, the particle may nevertheless be cleared following in vivo degradation to a smaller size.

In some embodiments, the particles may be adapted to facilitate clearance by hepatobiliary excretion. The mononuclear phagocytic system (MPS), which includes the Kupffer cells in the liver, is involved in the liver uptake and subsequent biliary excretion of nanoparticles. Certain size and surface properties of nanoparticles are known to increase uptake by the MPS in the liver (see Choi et al., J. Dispersion Sci. Tech. 24(3/4):475-487 (2003); and Brannon-Peppas et al., J. Drug Delivery Sci. Tech. 14(4):257-264 (2004), each of which is incorporated by reference). For example, increasing the hydrophobicity of a particle is known to increase uptake by the MPS. Thus, one of ordinary skill in the art can select for particles having certain characteristics to modulate biliary excretion. The hepatobiliary system allows for the excretion of particles that are somewhat larger than those that may be excreted through the renal system (e.g., 10 to 20 nm). For embodiments in which a particle is too large for hepatobiliary excretion, the particle may nevertheless be cleared following in vivo degradation to a smaller size. In such embodiments, a coating that facilitates clearance by hepatobiliary excretion may cover a portion of an inner surface of a particle such that the coating becomes exposed following degradation of the particle. The particle may comprise a plurality of coating molecules, e.g., hydrophobic molecules, that cover a portion of a surface. The surface may be exposed following degradation of the particle, allowing for clearance of the degraded particle.

In some embodiments, the particle is adapted to facilitate clearance by phagocytosis. For example, the particle may comprise a clearance agent, wherein the clearance agent comprises a pathogen-associated molecular pattern, e.g., for recognition by macrophages. Pathogen-associated molecular patterns (PAMPs) include unmethylated CpG DNA (bacterial), double-stranded RNA (viral), lipopolysacharride (bacterial), peptidoglycan (bacterial), lipoarabinomannan (bacterial), zymosan (yeast), mycoplasmal lipoproteins such as MALP-2 (bacterial), flagellin (bacterial), poly(inosinic-cytidylic) acid (bacterial), lipoteichoic acid (bacterial), and imidazoquinolines (synthetic). In preferred embodiments, the PAMP clearance agent is masked such that macrophages do not engulf the particle prior to the binding of the particle to one or more targets. For example, a PAMP clearance agent may be masked by any one of the aforementioned coatings (e.g., a polymeric coating, such as a biodegradable polymeric coating). Macrophages can engulf particles as large as 20 µm (see, e.g., Cannon, G. J. and Swanson, J. A., J. Cell Science 101:907-913 (1992); Champion, J. A., et al., Pharm Res 25(8):1815-1821 (2008)). In some embodiments, a clearance agent that facilitates clearance by phagocytosis may cover a portion of an inner surface of a particle such that the clearance agent becomes exposed following degradation of the particle. The particle may comprise a plurality of clearance agents, e.g., PAMPs, that cover a portion of a surface. The surface may be exposed following degradation of the particle, allowing for clearance of the degraded particle. The clearance agent may cover a portion of a surface that overlaps a surface comprising an agent. The clearance agent (e.g., PAMPs) may elicit an immune response against the particle, e.g., following the degradation of a second coating or following the degradation of the particle.

In some embodiments, an immune response directed against a clearance agent (e.g., PAMPs) may outcompete an immune response directed against the agent and/or agent/biomolecule complex, thereby inhibiting or delaying the onset of an immune response directed against the agent and/or agent/biomolecule complex. For example, degradation of a particle may expose both a clearance agent and an agent (and/or agent/biomolecule complex) to leukocytes. A PAMP clearance agent may allow for rapid clearance of the degraded particle by macrophages, thereby delaying an immune response (e.g., B-cell mediated immune response) against the agent and/or agent/biomolecule complex.

A clearance agent may be calreticulin, which induces phagocytosis.

In certain preferred embodiments, the coating molecule comprises a nucleic acid, e.g., for hybridizing with a coating molecule to a particle comprising a DNA scaffold. For example, a particle may comprise a nucleic acid and a coating molecule, wherein the coating molecule comprises a complementary nucleic acid that can hybridize with the nucleic acid, thereby forming a bond between the coating molecule and the particle (i.e., hydrogen bonds). The nucleic acid may comprise a nucleotide sequence and the complementary nucleic acid may comprise a complementary nucleotide sequence, e.g., wherein the nucleotide sequence has at least 95%, 96%, 97%, 98%, or 99% sequence identity with the reverse complement of the complementary nucleotide sequence. The nucleotide sequence may have 100% sequence identity with the reverse complement of the complementary nucleotide sequence.

Preferably, the melting temperature of the nucleic acid and complementary nucleic acid in physiological fluid (e.g., blood) is greater than body temperature (e.g., the body temperature of a subject, such as a human or mouse). For example, the melting temperature of the nucleic acid and complementary nucleic acid in physiological fluid is preferably greater than 37° C., such as greater than about 38° C., greater than about 39° C., greater than about 40° C., greater than about 41° C., greater than about 42° C., greater than about 43° C., greater than about 44° C., or greater than about 45° C. The melting temperature of the nucleic acid and complementary nucleic acid may be about 37° C. to about 120° C., such as about 38° C. to about 120° C., about 39° C. to about 120° C., about 40° C. to about 120° C., about 41° C. to about 120° C., about 42° C. to about 120° C., about 43° C. to about 120° C., about 44° C. to about 120° C., about 45° C. to about 120° C., about 46° C. to about 120° C., about 47° C. to about 120° C., about 48° C. to about 120° C., about 49° C. to about 120° C., about 50° C. to about 120° C., about 38° C. to about 100° C., about 39° C. to about 100° C., about 40° C. to about 100° C., about 41° C. to about 100° C., about 42° C. to about 100° C., about 43° C. to about 100° C., about 44° C. to about 100° C., about 45° C. to about 100° C., about 46° C. to about 100° C., about 47° C. to about 100° C., about 48° C. to about 100° C., about 49° C. to about 100° C., or about 50° C. to about 100° C.

The length of the nucleic acid of the reactive group, nucleotide sequence of the reactive group, complementary nucleic acid, and complementary nucleotide sequence is preferably greater than 9 nucleotides. The length of the nucleic acid of the reactive group, nucleotide sequence of the reactive group, complementary nucleic acid, and complementary nucleotide sequence may be greater than 10, 11, 12, 13, 14, 15, 16, 17, 18, 19, or 20 nucleotides. The length of the nucleic acid of the reactive group, nucleotide sequence of the reactive group, complementary nucleic acid, and complementary nucleotide sequence may be about 10 nucleotides to about 100 nucleotides, such as about 11 nucleotides to about 80 nucleotides, about 12 nucleotides to about 60 nucleotides, about 13 nucleotides to about 50 nucleotides, about 14 nucleotides to about 40 nucleotides, about 15 nucleotides to about 30 nucleotides, or about 16 nucleotides to about 25 nucleotides. The GC content of the nucleic acid, nucleotide sequence, complementary nucleic acid, and complementary nucleotide sequence may be about 10% to about 100%, such as about 40% to about 100%, about 45% to about 100%, about 50% to about 100%, about 55% to about 100%, about 40% to about 95%, about 45% to about 90%, about 50% to about 85%, or about 55% to about 80%.

In some embodiments, a particle may be cleared by an organism in about 1 day to about 5 years, such as about 1 day to about 3 years, or about 1 day to about 1 year.

XIV. Applications

The compositions (e.g., particles and pharmaceutical compositions thereof) described herein are useful in a variety of diagnostic and therapeutic applications. For example, the particles described herein can be used to treat cancer, detoxify a subject, or treat viral or bacterial infections.

Therapeutic applications include administering one or more of the compositions described herein to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

In some aspects, the invention relates to a method for removing a biomolecule from a composition, comprising contacting the composition with a particle as described herein. Such methods are particularly useful for scientific research. For example, it is relatively easy to add a biomolecule to a solution, however it is somewhat more challenging to remove a specific biomolecule from a solution.

Current techniques for removing a biomolecule from solution include, for example, binding the biomolecule to a particle, such as a sepharose bead, and then physically separating the bead from the solution. The particles described herein may sequester a biomolecule in a composition, thereby inhibiting interactions with other components of the composition (e.g., cells), without the need to physically separate the particles from the composition.

A particle may comprise a fluorophore. A particle may be magnetic or paramagnetic or a particle may comprise a magnetic or paramagnetic subparticle or component that allows the particle to be attracted to a magnetic field.

A method may comprise contacting a composition with a particle as described herein, wherein the composition is a cell culture. For example, the cell culture may be a bacterial cell culture or a tissue culture. Such methods may be useful, for example, to remove a secreted protein from the cell culture or to remove a contaminant from the cell culture.

A method may comprise contacting a composition with a particle as described herein, wherein the composition is a cell lysate. The cell lysate may be a prokaryotic or eukaryotic cell lysate. Such methods may be useful, for example, to inhibit the activity of a target biomolecule.

The above methods may be particularly useful for assessing the function of a biomolecule of interest in a particular system. For example, the biomolecule may be introduced to a system (e.g., tissue culture) to assess the effect of the biomolecule on the system (e.g., cell proliferation or cell death), and the biomolecule may be depleted from a similar system using a particle as described herein to assess the effect of the absence of the biomolecule on the system.

XV. Kits for Coupling an Agent to a Particle

In some aspects, the invention relates to a kit for making a scavenging particle. The kit may comprise a plurality of particles. The kit may comprise instructions for coupling the reactive groups of a particle to a plurality of agents to prepare the scavenging particle. The kit may comprise instructions for functionalizing the reactive groups of a particle to prepare the scavenging particle. The kit may further comprise a plurality of linkers. Each linker of the plurality of linkers may comprise a first functional group capable of selectively reacting with an agent bearing a predetermined moiety capable of reacting with the first functional group. Each linker of the plurality of linkers may comprise a second functional group capable of selectively reacting with the reactive groups of the particles. In some embodiments, the kit does not comprise linkers, e.g., when the reactive groups of the particle can selectively react with the agent, thereby coupling the agent to the particle. The kit may further comprise a plurality of agents, each agent bearing the predetermined moiety. A predetermined moiety may be a primary amine, guanidinium, thiol, or carboxyl group, e.g., for an agent that comprises a peptide or protein. In some embodiments, the kit does not comprise an agent, e.g., for creating a custom scavenging particle.

In some embodiments, the kit comprises a second plurality of linkers, e.g., wherein each linker of the second plurality of linkers comprises a third functional group capable of selectively reacting with an agent bearing a second predetermined moiety capable of reacting with the third functional group. For example, the first functional group may be capable of reacting with a predetermined moiety of a protein, and the third functional group may be capable of reacting with a predetermined moiety of a nucleic acid, such that the particle may be loaded with a protein and/or nucleic acid by utilizing different linkers.

XVI. Methods for Making a Scavenging Particle

In some aspects, the invention relates to a method for making a scavenging particle. The method may comprise reacting a particle with a plurality of agents. Each agent of the plurality of agents may comprise a functional group or predetermined moiety capable of selectively reacting with a reactive group of the plurality of reactive groups. Each reactive group may be oriented on the particle such that, after the agent is coupled to the particle, the agent has a reduced ability to bind to a molecule on the surface of a cell (e.g., a eukaryotic cell, such as a diploid cell, such as a human diploid cell, such as an immune cell or a cancer cell).

The method may further comprise reacting the plurality of agents with a plurality of linkers, e.g., prior to reacting the particle with the plurality of agents. For example, each linker of the plurality of linkers may comprise a first functional group capable of selectively reacting with an agent bearing a predetermined moiety capable of reacting with the first functional group. Each linker of the plurality of linkers may comprise a second functional group capable of selectively reacting with the reactive groups of the particles. Thus, the agent may be functionalized to add a functional group that can selectively react with a reactive group of the particle. Each linker may comprise a protecting group, e.g., which protects the second functional group. The method may further comprise deprotecting the linker, e.g., after reacting the plurality of agents with the plurality of linkers.

The method may further comprise reacting the particle with a plurality of linkers, e.g., prior to reacting the particle with the plurality of agents. For example, each linker of the plurality of linkers may comprise a second functional group capable of selectively reacting with a reactive group. Each linker of the plurality of linkers may comprise a first functional group capable of selectively reacting with an agent bearing a predetermined moiety capable of reacting with the first functional group. Thus, the particle may be functionalized to selectively react with a predetermined moiety of the agent. Each linker may comprise a protecting group, e.g., which protects the first functional group. The method may further comprise deprotecting the linker, e.g., after reacting the particle with the plurality of linkers.

Methods of preparing a scavenging particle may result in particles comprising agent that cannot bind to a biomolecule, e.g., if the binding region of the agent couples to a reactive group and/or a linker. A population of agents may nevertheless be accessible to specifically bind to the biomolecule. In some embodiments, each agent of the plurality of agents can specifically bind to the biomolecule. In some embodiments, each agent of the particle can specifically bind to the biomolecule.

Methods of preparing a scavenging particle may result in particles comprising agent that can interact with cells, such as cancer cells or immune cells. A population of agents may nevertheless display a reduced ability to bind to a molecule on the surface of a cell (e.g., a diploid human cell, cancer cell, and/or immune cell). In some embodiments, each agent of a plurality of agents displays a reduced ability to bind to a molecule on the surface of a cell (e.g., a diploid human cell, cancer cell, and/or immune cell), e.g., relative to agent immobilized on the outside surface of a particle. In some embodiments, each agent of a particle displays a reduced ability to bind to a molecule on the surface of a cell (e.g., a diploid human cell, cancer cell, and/or immune cell), e.g., relative to agent immobilized on the outside surface of a particle.

The foregoing applies to any of the compositions and methods described herein.

The disclosure specifically contemplates any combination of the features of such compositions and methods (alone or in combination) with the features described for the various kits described in this section.

Unless otherwise defined, all technical and scientific terms used herein have the same meaning as commonly understood by one of ordinary skill in the art to which this disclosure pertains. Preferred methods and materials are described herein, although methods and materials similar or equivalent to those described herein can also be used in the practice or testing of the presently disclosed methods and compositions. All publications, patent applications, patents, and other references mentioned herein are incorporated by reference in their entirety.

The disclosure contemplates all combinations of any of the foregoing aspects and embodiments, as well as combinations with any of the embodiments set forth in the detailed description and examples. These and other aspects of the present disclosure will be further appreciated upon consideration of the following Examples, which are intended to illustrate certain particular embodiments of the disclosure but are not intended to limit its scope, as defined by the claims.

EXEMPLIFICATION

Example 1—Method for Manufacturing Silicon Particles

Porous silicon disks are manufactured with sizes of 1000 nm by 400 nm and 1000 nm by 800 nm with variable pore sizes. The size and morphology of the disks, as well as pore diameters, are characterized by scanning electron microscopy. Gold nanoparticles (Au) are deposited in the pores of the porous silicon disks. Tumor necrosis factors (TNFs) are conjugated to the surfaces of the gold nanoparticles through dative covalent bonds. The ligand density and TNF-Au binding stabilities are assessed.

Example 2—Method for Manufacturing Polymer Particles

Poly(lactide-co-glycolide) (PLGA) particles are fabricated by emulsion. The size and morphology of the PLGA particles are characterized by scanning electron microscopy, atomic force microscopy, and transmission electron microscopy. The particles are coated with quaternary ammonium beta-cyclodextrin, for macrophage recruitment (i.e., phagocytosis). The coating is verified by atomic force microscopy and transmission electron microscopy. Coating density and uniformity is characterized by transmission electron microscopy and dynamic light scattering.

The beta-cyclodextrin-coated PLGA particles are incubated with macrophages, and phagocytosis is monitored by fluorescence microscopy and by flow cytometry.

The beta-cyclodextrin-coated PLGA particles are coated with a blend of polyethylene glycol (PEG) and thiol moieties to allow for prevention of opsonization and evasion of macrophage uptake, as well as binding to other particles. The uniformity and density of the PEG and thiol coatings are characterized by atomic force microscopy. Coating stabilities are characterized by incubating the particles in media for various periods of time. Evasion and uptake of the particles are monitored at various time points by incubating the particles with macrophages, as described above.

The PLGA particles are coated with tumor necrosis factor (TNF), and the particles are combined by disulfide bonds to form a “sponge,” comprising TNF on the interior surface of the sponge. The exterior surface (i.e., outer surface) of the sponge is optionally blocked with particles that do not comprise TNF to prevent interactions between the TNF of the sponge and cells.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 3—Method for Manufacturing DNA Particles

A DNA nanotube will be assembled using protocols similar to those described in Douglas et al. (Nature 459 (7245):414-8 (2009), hereby incorporated by reference in its entirety). The nanotubes will include five internal biotins. DNA strands that are not incorporated into nanotubes will be removed using a 300 kDa MWCO filter unit. The nanotubes will be characterized by atomic force microscopy.

Biotin-labeled TNFα will be mixed with streptavidin tetramer in a 3:1 ratio to produce TNFα modules with three human TNFα bound to one streptavidin molecule, at a concentration of about 300 nM. The TNFα modules will then be incubated with the DNA nanotubes to produce nanotubes comprising the TNFα modules. The nanotubes will be purified using a 300 kDa MWCO filter unit and characterized by atomic force microscopy.

A TNFα assay will be used to confirm the TNFα modules are attached to the nanotubes and to generate solutions of nanotubes comprising TNFα at 5 nM, 10 nM, 15 nM, 25 nM, 35 nM, and 50 nM concentrations (Abcam Catalogue # ab181421).

The ability of the TNFα nanotubes to bind soluble TNF-receptor will be assessed using an ELISA assay (Abcam Catalogue # ab100642). Briefly, the nanotubes will be added at various concentrations to different wells of a 96-well plate coated with an anti-soluble TNF receptor antibody. Soluble TNF receptor will be added to the wells, the plate will be incubated for a period of time, and then the nanotubes will be washed from the wells along with soluble TNF that is bound to the nanotubes. A biotinylated anti-soluble TNF receptor antibody will be added to the wells, the wells will be washed to remove unbound antibody, horseradish peroxidase-conjugated streptavidin will be added to the wells, the wells will be washed to remove unbound horseradish peroxidase, and 3,3',5,5'-tetramethylbenzidine (TMB) will be added to the wells. The amount of TNF-receptor bound to the anti-TNF receptor antibodies of the wells will be quantified by monitoring TMB at 450 nm and/or production of 3,3',5,5'-tetramethylbenzidine diimine from TMB at 650 nm. Wells that receive higher concentrations of nanotubes will display higher absorbance at 450 nm and lower absorbance at 650, corresponding to less soluble TNF-receptor bound to the wells, and thus, less peroxidase activity.

What is claimed is:

1. A particle comprising a first plurality of reactive groups, wherein:
   each reactive group of the first plurality of reactive groups can selectively react with a first agent comprising a first predetermined functional group;
   each reactive group of the first plurality of reactive groups is disposed on the particle such that after the first agent is linked to that reactive group through the first predetermined functional group, the first agent has a reduced ability to bind to a molecule on the surface of a cell;
   the particle comprises a plurality of coating molecules, wherein the plurality of coating molecules comprises a polymer; and
   the longest dimension of the particle is about 50 nm to about 5 μm.

2. The particle of claim 1, wherein each reactive group of the first plurality of reactive groups comprises an alkene, alkyl halide, alkyne, amine, aryl azide, aryl halides, azide, carbodiimide, carboxyl, diene, dienophile, glyoxal, haloacyl, imidoester, isocyanide, maleimide, N-hydroxysuccinimidyl ester, phosphine, tetrazine, thiol, nucleic acid, biotin, or biotin-binding protein.

3. The particle of claim 1, further comprising a second plurality of reactive groups, wherein:
   each reactive group of the second plurality of reactive groups can selectively react with a second agent comprising a second predetermined functional group;
   each reactive group of the second plurality of reactive groups is disposed on the particle such that after the second agent is linked to that reactive group through the second predetermined functional group, the second agent has a reduced ability to bind to a molecule on the surface of a cell; and
   the longest dimension of the particle is about 50 nm to about 5 μm.

4. The particle of claim 3, wherein the first predetermined functional group is different from the second predetermined functional group.

5. The particle of claim 3, wherein:

the first predetermined functional group is the same as the second predetermined functional group; and at least one reactive group of the first plurality of reactive groups and the second plurality of reactive groups is protected by a protecting group.

6. The particle of claim 1, wherein the particle is shaped and sized to circulate in the vasculature of a subject.

7. The particle of claim 1, wherein:

the particle comprises an interior surface and an exterior surface;

the plurality of coating molecules is bound to the exterior surface;

each reactive group of the first plurality of reactive groups is located on the interior surface or the exterior surface; and after the first agent is linked to a member of the first plurality of reactive groups through the first predetermined functional group, the coating molecules inhibit the first agent linked to a member of the first plurality of reactive groups located on the exterior surface from binding to a molecule on the surface of a cell.

8. The particle of claim 1, wherein:

the particle is porous;

the particle comprises outer surfaces and inner surfaces;

the inner surfaces consist of the inner walls of the pores of the particle; and the reactive groups of the first plurality of the reactive groups are located on the inner surfaces of the particle.

9. The particle of claim 1, wherein:

the particle comprises a core subparticle and a plurality of protecting subparticles;

the reactive groups of the first plurality of the reactive groups are located on the core subparticle.

10. The particle of claim 9, wherein the particle comprises 4 to $10^6$ protecting subparticles.

11. The particle of claim 9, wherein the particle comprises more than one core subparticle.

12. The particle of claim 1, wherein the reactive groups of the first plurality of the reactive groups are disposed on the particle such that after the first agent is linked to a member of the first plurality of reactive groups through the first predetermined functional group, the first agent has a reduced ability to bind to a target on the surface of a cell, or to bind or activate a cell surface receptor protein on the surface of a cell.

13. The particle of claim 1, wherein each reactive group of the first plurality of reactive groups is configured such that after the first agent is linked to a member of the first plurality of reactive groups through the first predetermined functional group, the first agent has a lower binding affinity for membrane-associated forms of a target biomolecule than the binding affinity of the first agent that is free in solution for the same target biomolecule.

14. The particle of claim 13, wherein the association constant of the first agent linked to a member of the first plurality of reactive groups and a membrane-associated form of a target biomolecule ($k_{a,\ particle}$) is less than 0.1 times the association constant of the first agent and the membrane-associated form of a target biomolecule when the first agent is free in solution ($k_{a,\ free}$; $k_{a,\ particle} \div k_{a,\ free} \leq 0.1$); or wherein the equilibrium constant of the first agent linked to a member of the first plurality of reactive groups and a membrane-associated form of a target biomolecule ($K_{D,\ particle}$) is greater than 5 times the equilibrium constant of the first agent and the membrane-associated form of a target biomolecule when the first agent is free in solution ($K_{D,\ free}$; $K_{D,\ particle} \div K_{D,\ free} > 5$).

15. The particle of claim 1, wherein each reactive group of the first plurality of reactive groups is configured such that after the first agent is linked to a member of the first plurality of reactive groups through the first predetermined functional group, the first agent has about the same binding affinity for soluble forms of a target biomolecule relative to the binding affinity of the first agent that is free in solution for the same target biomolecule.

16. The particle of claim 15, wherein:

the association constant of the first agent linked to a member of the first plurality of reactive groups and a soluble form of a target biomolecule ($k_{a,\ particle}$) is from 0.1 to 10 times the association constant of the first agent and the soluble form of a target biomolecule when the first agent is free in solution ($k_{a,\ free}$; $0.1 \leq k_{a,\ particle} \div k_{a,\ free} \leq 10$); or wherein:

the equilibrium constant of the first agent linked to a member of the first plurality of reactive groups and a soluble form of a target biomolecule ($K_{D,\ particle}$) is from 0.1 to 10 times the equilibrium constant of the first agent and the soluble form of a target biomolecule when the first agent is free in solution ($K_{D,\ free}$; $0.1 \leq K_{D,\ particle} \div K_{D,\ free} \leq 10$).

17. A method for making a scavenging particle, comprising reacting the particle of claim 1 with a plurality of first agents, wherein:
- each first agent of the plurality of first agents is coupled to a member of the first plurality of reactive groups through the first predetermined functional group.

18. The particle of claim 1, wherein:
- the particle comprises an interior surface and an exterior surface; and
- the reactive groups of the first plurality of reactive groups are located on the interior surface.

19. The particle of claim 1, wherein:
- the particle comprises an interior surface and an exterior surface;
- the particle comprises a first plurality of reactive groups and a second plurality of reactive groups;
- the reactive groups of the first plurality of reactive groups are located on the interior surface; and
- the reactive groups of the second plurality of reactive groups are located on the exterior surface.

20. The particle of claim 1, wherein at least one of the reactive groups of the first plurality of reactive groups is oriented on the particle relative to the plurality of coating molecules such that after the first agent is linked to that reactive group through the first predetermined functional group, the plurality of coating molecules sterically inhibits the first agent from binding to a molecule on the surface of a cell.

* * * * *